US008790906B2

(12) United States Patent
Ochiai

(10) Patent No.: US 8,790,906 B2
(45) Date of Patent: Jul. 29, 2014

(54) LYSOPHOSPHOLIPID ACYLTRANSFERASE

(75) Inventor: Misa Ochiai, Osaka (JP)

(73) Assignee: Suntory Holdings Limited, Osaka (JP)

( * ) Notice: Subject to any disclaimer, the term of this patent is extended or adjusted under 35 U.S.C. 154(b) by 181 days.

(21) Appl. No.: 13/255,390

(22) PCT Filed: Mar. 25, 2010

(86) PCT No.: PCT/JP2010/055244
§ 371 (c)(1),
(2), (4) Date: Sep. 8, 2011

(87) PCT Pub. No.: WO2010/110375
PCT Pub. Date: Sep. 30, 2010

(65) Prior Publication Data
US 2012/0115231 A1 May 10, 2012

(30) Foreign Application Priority Data
Mar. 26, 2009 (JP) ................. 2009-076809

(51) Int. Cl.
C12N 9/10 (2006.01)
C12N 1/20 (2006.01)
C12N 1/00 (2006.01)
C12N 15/00 (2006.01)
C12P 21/06 (2006.01)
C12P 19/34 (2006.01)
C07H 21/04 (2006.01)
C07C 51/43 (2006.01)
C07C 53/00 (2006.01)
C07K 1/00 (2006.01)

(52) U.S. Cl.
USPC ............... 435/193; 435/252.3; 435/254.11; 435/320.1; 435/69.1; 435/91.1; 435/440; 536/23.1; 536/23.2; 554/175; 554/224; 530/350

(58) Field of Classification Search
USPC ............. 435/193, 252.3, 254.11, 320.1, 69.1, 435/91.1, 440; 536/23.1, 23.2; 554/175, 554/224; 530/350
See application file for complete search history.

(56) References Cited

U.S. PATENT DOCUMENTS

2006/0094092 A1 5/2006 Damude et al.
2006/0168687 A1 7/2006 Renz et al.
2006/0174376 A1 8/2006 Renz et al.
2007/0072275 A1 3/2007 Ochiai et al.
2008/0145867 A1 6/2008 Zou et al.
2009/0209774 A1 8/2009 Renz et al.
2010/0016431 A1 1/2010 Chen et al.
2010/0203218 A1 8/2010 Ochiai et al.
2011/0023185 A1 1/2011 Renz et al.

FOREIGN PATENT DOCUMENTS

| CN | 1839199 | 9/2006 |
| EP | 2 169 055 A1 | 3/2010 |
| WO | 2004/076617 A2 | 9/2004 |
| WO | 2004/087902 A2 | 10/2004 |
| WO | 2008/076377 A2 | 6/2008 |
| WO | 2008/146745 | 12/2008 |
| WO | 2009/001315 A2 | 12/2008 |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Chinese Office Action issued with respect to Chinese Patent App. No. 201080015945.0, dated Jul. 12, 2013.
International Search Report for PCT/JP2010/055244, mailed May 18, 2010.
Chatrattanakunchai et al., "Oil biosynthesis in microsomal membrane preparations from *Mortierella alpina*," *Biochemical Society Transactions*, vol. 28, No. 6, pp. 707-709, 2000.
Stahl et al., "A family of eukaryotic lysophospholipid acyltransferases with broad specificity," *FEBS Letters*, vol. 582, No. 2, pp. 305-309, available online Dec. 26, 2007.
Extended European Search Report for patent family member EP Application No. 10756171.4, dated Aug. 16, 2012.

* cited by examiner

*Primary Examiner* — Ganapathirama Raghu
(74) *Attorney, Agent, or Firm* — Greenblum & Bernstein, P.L.C.

(57) ABSTRACT

The present invention provides novel lysophospholipid acyltransferases. The object of the present invention is attained by the nucleotide sequences of SEQ ID NOs: 1 and 6 and the amino acid sequences of SEQ ID NOs: 2 and 7 of the present invention.

15 Claims, 10 Drawing Sheets

Figure 2

```
   1 CCTCCCTCCTCCTCGTAGACGAACTCCTTCCCGCTGACGGAGAAGTCTTGAGCTGAGTTCATCCTCAAAGAGATCAAATTTTTTCCCCTCCCTCTCCTCG

101 TCGTCTTCACGTCTCTTCTTCTTTCTATACCACAGCACACTCGCCATAGCACAACTCACCATGCTAAACTCATTCTTCGGGACGCTCTCGGAGGCTGTCT
                                                        M  L  N  S  F  F  G  T  L  S  E  A  V  S  ·

201 CCTTCCCAGAGGATCAGCTTCGTTGCCTCTCGGCTCTGTTACTCTCCTACCCTCTGGCACTTGCTTTTCGCCTACTGCCCAACAACCCCAACCTTAAACA
      · F  P  E  D  Q  L  R  C  L  S  A  L  L  L  S  Y  P  L  A  L  A  F  R  L  L  P  N  N  P  N  L  K  H  ·

301 TACTGTCTCTGTCCTGACTTCCTTCTTCCTGATCGTGGTTATTGTGGATGATCTCGTCGGATTGATGCATCTTCTGGGATCCAGCATCGCTGTCTGGAGG
      · T  V  S  V  L  T  S  F  F  L  I  V  V  I  V  D  D  L  V  G  L  M  H  L  L  G  S  S  I  A  V  W  R

401 ATAATGGGTGCCGTTCAAGGCAAATGGGGGCCACGGCTAGTTTTTATTGGCGTTATGCTCCATATGAGCGTCAGTCATCTGCTTCGTCAGTTCCACGACT
        I  M  G  A  V  Q  G  K  W  G  P  R  L  V  F  I  G  V  M  L  H  M  S  V  S  H  L  L  R  Q  F  H  D  Y  ·

501 ATAGAGGATACAAGCTGGATCACACCGGTCCTCAAATGATTCTCACCATGAAACTCACCTCTTGGGCCTTCAATGTCTATGATGGCCGCCGTAACCCAAA
      · R  G  Y  K  L  D  H  T  G  P  Q  M  I  L  T  M  K  L  T  S  W  A  F  N  V  Y  D  G  R  R  N  P  K  ·

601 GGAACTCAGCAGATATCAGCAAGACCACGCCGTCCTATCGTTCCCTTCCCTTCTTCACTACCTCAGCTATGTCTTCTTCTTCCCCTCCGTTCTCGTTGGT
      · E  L  S  R  Y  Q  Q  D  H  A  V  L  S  F  P  S  L  L  H  Y  L  S  Y  V  F  F  F  P  S  V  L  V  G

701 CCCTCATTCGAATATATGGATTATATCCGCTTCATTGAGCTCACTCAGTTCCGGGACCCCAAGACTGGAAAGATCCACTGGCCCGCAGGTCGTGTCCGAT
        P  S  F  E  Y  M  D  Y  I  R  F  I  E  L  T  Q  F  R  D  P  K  T  G  K  I  H  W  P  A  G  R  V  R  S  ·

801 CTTCCATGAGGACTTTCTTTTTTGCTATGATTGCCTTGGCCTGTCTGGCGGTTGTCGGGCCCAAACTCGATGTTCTTTGGACGATGGAGCCGGCTTGGAA
      · S  M  R  T  F  F  F  A  M  I  A  L  A  C  L  A  V  V  G  P  K  L  D  V  L  W  T  M  E  P  A  W  K  ·

901 AGCTCTGCCATGGATCTTGCGCTTTGGTTATGTGCAACTGGCCGCCTTTGCGGCTCGTTTCAAGTACTATGCGGTGTGGAAGCTGGCCGAGGGCGCCTGT
      · A  L  P  W  I  L  R  F  G  Y  V  Q  L  A  A  F  A  A  R  F  K  Y  Y  A  V  W  K  L  A  E  G  A  C

1001 GTTATGGCTGGATTCGGATACAACGGACAGGATCCCAAGACGGGCGAAGCTCGGTGGGATGCGACCTCCAACATTAACGTTTGGGCCTACGAGACTGGCC
        V  M  A  G  F  G  Y  N  G  Q  D  P  K  T  G  E  A  R  W  D  A  T  S  N  I  N  V  W  A  Y  E  T  G  Q  ·

1101 AGAGCATCAAAACTTTGGCTGATAACTGGAATATGGGCACCAACAAGTGGTTAAAGCACTCCGTGTACTTTAGAGTCGTTGCTCCCGGGGCGAAGCCTGG
      · S  I  K  T  L  A  D  N  W  N  M  G  T  N  K  W  L  K  H  S  V  Y  F  R  V  V  A  P  G  A  K  P  G  ·

1201 TTTCTTGGAGACGTTTGCGACGTTTGGTGTGAGCGCGCTGTGGCACGGATTCTACCCCGGATATTACCTGATGTTTGCTTCTGCGGCCATGGCTCTTACA
      · F  L  E  T  F  A  T  F  G  V  S  A  L  W  H  G  F  Y  P  G  Y  Y  L  M  F  A  S  A  A  M  A  L  T

1301 GCGGGCAAATTGTTGAGGACTCATTTGCGGCCGAGGTTTGTGTCAGCCTCGACAGGAAAGACGCCTCTTCTGTACAATATGCTGGGCATGGTCTTGACCC
        A  G  K  L  L  R  T  H  L  R  P  R  F  V  S  A  S  T  G  K  T  P  L  L  Y  N  M  L  G  M  V  L  T  Q  ·

1401 AGGCGACGATCAACACACTGTCCATGTCGTTCTTGCTGCTAACATTCAAGGACAGCATTGAGGTTTGGAAGAACCTCTACTTTGTCGTCCACTTGGGTAT
      · A  T  I  N  T  L  S  M  S  F  L  L  L  T  F  K  D  S  I  E  V  W  K  N  L  Y  F  V  V  H  L  G  I  ·

1501 CATCGCCATCACGGTTCTGGTTCCCGTCTTATTCCCAGTGAAGCGAAAGCCCAAGAAAGAGCAGCAGCAGCCCGAGGTCGAGAAGGTCAAGGAACTCATG
      · I  A  I  T  V  L  V  P  V  L  F  P  V  K  R  K  P  K  K  E  Q  Q  Q  P  E  V  E  K  V  K  E  L  M

1601 CATGATGTTGCAGAGGAGGTTGCCACCGTCTCTGTGAGTGCTGCCAGCGAGCTCCTTGACACCTCTGCTGCAGTTAAAATCAAGACGCTGTAAATGGATG
        H  D  V  A  E  E  V  A  T  V  S  V  S  A  A  S  E  L  L  D  T  S  A  A  V  K  I  K  T  L

1701 CTTTGCGACGTTCCCTCTTGACCATAGCGAGCACGCTATCATTACCACATCTGTACACATACCTCTCCACACTCCACGCACAACTTATGTGCATAAAGAA
1801 CAGCTTTCCACTGTAAAAAAAAAAAAAAAAAAAAA
```

Figure 3

```
   1 CCCTCCCCTGGCAAAAACAGACAGCGCACGAGTAAAGATGGAGGCACTCTTGCACCAGGTTCATGACACCTACCTGCCCGCTTGGTTCGGACCCAAACCC
                                       M  E  A  L  L  H  Q  V  H  D  T  Y  L  P  A  W  F  G  P  K  P

101 CCGGCGGCTTTTCTCGACTATGGTCTGACCCAGTCCCTAAGCGAGGCCTCGGGCATTCCCGAACCCTCGCTGCGTCTACTCATGACGATCCTGGCGGGTT
      P  A  A  F  L  D  Y  G  L  T  Q  S  L  S  E  A  S  G  I  P  E  P  S  L  R  L  L  M  T  I  L  A  G  Y ·

201 ACCCAGTCTCGTTCATTTACCGACTCATCTTTCTGAACAAGACGTCGAGCATTGTGGGCGAATCGGCACGGAACGCGTTCTTCTTGTCCACGGGCTTGCT
      · P  V  S  F  I  Y  R  L  I  F  L  N  K  T  S  S  I  V  G  E  S  A  R  N  A  F  F  L  S  T  G  L  L ·

301 CCTCTCTTACTACTTCAACTCGTTTGATATCATCCACCCTCTGACCACCTGTATCGGCACCTGGCTCATCTGCAAGGTCGTAGGTGCGATCGCTCCCAAG
      · L  S  Y  Y  F  N  S  F  D  I  I  H  P  L  T  T  C  I  G  T  W  L  I  C  K  V  V  G  A  I  A  P  K

401 AATCGGTCGCTGGCCTCGACGGTCGCGTTCCTCTTCAACTTTGGATATCTGCTCACGTCCTACAAGTACGCGGCCACGGAGGATTACGACATCTGCTACA
      N  R  S  L  A  S  T  V  A  F  L  F  N  F  G  Y  L  L  T  S  Y  K  Y  A  A  T  E  D  Y  D  I  C  Y  T ·

501 CGATGCAGCAATGTGTCCAGTGTCTTCGCATGATCGGATATGGTATGGACTTTATGGACGGACAGCCCAAACCCGCAAGCAAGAAACATCTGGCCGCTGC
      · M  Q  Q  C  V  Q  C  L  R  M  I  G  Y  G  M  D  F  M  D  G  Q  P  K  P  A  S  K  K  H  L  A  A  A ·

601 CGCGAGTGCCGAGACTTTGGCCACATTGGTCGAGGAGGTCAAGGCCAACCCCAACAAGGCCGATCAGGGCATCGACCACGTCGTGGTCGCTCCCAGCCCC
      · A  S  A  E  T  L  A  T  L  V  E  E  V  K  A  N  P  N  K  A  D  Q  G  I  D  H  V  V  A  P  S  P

701 GCTGCCGTCACCCCTGTCAGGGAAAAGACTCCAATTTCGTTCGGACGGGACATTGCTCTCCCTCAGTTGCCCACGTTGGCCGAGACGATCGGCTATGCCT
      A  A  V  T  P  V  R  E  K  T  P  I  S  F  G  R  D  I  A  L  P  Q  L  P  T  L  A  E  T  I  G  Y  A  F ·

801 TCTTCCCGTTCGCGTTCTTGGTCGGCCCCCAGTTTTCGTTCTCGCTCTACAAAAAGTTCATTTCGATGGAGCTCTTCAATGTGCCGGTGCCTGCCTCGGC
      · F  P  F  A  F  L  V  G  P  Q  F  S  F  S  L  Y  K  K  F  I  S  M  E  L  F  N  V  P  V  P  A  S  A ·

901 CGGACGCGATGAGGCCAAGGCCGCTGCTGCTGCGACCGCGAACGGAATCCCCCAGGGTTCTCTGCGCTACGCGTTGCGCTGTTTCTCCCTTGGTGTGTTC
      · G  R  D  E  A  K  A  A  A  A  A  T  A  N  G  I  P  Q  G  S  L  R  Y  A  L  R  C  F  S  L  G  V  F

1001 TATCTGGGACTGGGTCAGGTTTTGGGAGGATACTTCCCCACGGCCGCATTGTTGGGTAAAGCCTTCCTGGAACGCTCGTACCTGGAGAAGGTCTTTATCT
      Y  L  G  L  G  Q  V  L  G  G  Y  F  P  T  A  A  L  L  G  K  A  F  L  E  R  S  Y  L  E  K  V  F  I  F ·

1101 TTTGGTGGACTGGAAAGACTGTCTTGAACAAGTACCTTGGCATTTGGACCATCGCCGAGGGACCCTGCGTCCTCTCGGGCATCACCTTCAACGGTTATGA
      · W  W  T  G  K  T  V  L  N  K  Y  L  G  I  W  T  I  A  E  G  P  C  V  L  S  G  I  T  F  N  G  Y  D ·

1201 CGCCCAGGGACGGCCCGAGTGGGACGGACTCCGGAACGTGAACCCTCTCAACTATGAGTTTGCGACGTCCCTGACCCAGATCGTGACCTCGTTCAACATG
      · A  Q  G  R  P  E  W  D  G  L  R  N  V  N  P  L  N  Y  E  F  A  T  S  L  T  Q  I  V  T  S  F  N  M

1301 AACACAAACTTCTGGGCCAAGCTTTACATCTTCAAGCGTCTGCGTTTCCTCGGTAACAAGAACCTGTCAGCCCTCGGCGTCTTGCTCTTCTTGGCGATCT
      N  T  N  F  W  A  K  L  Y  I  F  K  R  L  R  F  L  G  N  K  N  L  S  A  L  G  V  L  L  F  L  A  I  W ·

1401 GGCACGGAACCCATATCGGTTACTTTTTCTGCTTTGGCCTCGAGTTCATGGACATGGAGACCGAGCGTCGGTTGTCGGTTAGGTTTGGTCGTCCCATTAA
      · H  G  T  H  I  G  Y  F  F  C  F  G  L  E  F  M  D  M  E  T  E  R  R  L  S  V  R  F  G  R  P  I  N ·

1501 TGCGTTCATTGCTCGCCAGCAAGGTGTGAGCCATGCGATCCTCAAGGCCGTTTGGGGTGTCATCACCTGGCTCTTGACGACGAGTGCCCTGTACTTTGCG
      · A  F  I  A  R  Q  Q  G  V  S  H  A  I  L  K  A  V  W  G  V  I  T  W  L  L  T  T  S  A  L  Y  F  A

1601 GCCGTGCCTTTTGATCTGTTGCAGATGGACAAGTCGTTGGCGGCGATCCGGGCGATCAACTACCTCGGCATCTATGTCATGGCGGGACTTTTGTTCCTGG
      A  V  P  F  D  L  L  Q  M  D  K  S  L  A  A  I  R  A  I  N  Y  L  G  I  Y  V  M  A  G  L  L  F  L  D ·

1701 ACATTGCTCTGTCGGTGGTCATGCCCAAGAAGCGATCCAAGTCTGTCAAGACTGAGTAAAAATGGACAAAAAAAAGCAGGTTCTTTTAACTTAGATACCA
      · I  A  L  S  V  V  M  P  K  K  R  S  K  S  V  K  T  E

1801 GGAGAAATGAATGAATGAAGATGAACGAGAATCAAGGAGACGAAGGAACTAGTTTCTGAATGAGAAACTGTGTTCGAAGATAATAAAAAAAAAAAAAAAA
1901 A
```

Figure 4A

```
              1                                                                                                  100
LPLAT5-ORF    ATGCTAAAACTCATTCTTCGGGACGGCTCTCGGGAGGCTGTGTCCTTGCCCAGGATGAGGCTTGGTTGGGAGTCGGTAGTCCGTACCGTCTGGCAC
LPLAT5-g      ATGGTAAAACTCATTCTTCGGGACGGCTCTCGGGAGGCTGTGTCCTTGCCCAGGATGAGGCTTGGTTGGGAGTCGGTAGTCCGTACCGTCTGGCAC
              101                                                                                                200
LPLAT5-ORF    TTGCCTTTTGCCCTAGTGGCCAACAAGCCCAACCTTAAAGATACTGCTTCCTGAGTCTTCGTGATGGTTATGTTGGATGATGTCGTGG
LPLAT5-g      TTGCCTTTTGCCCTAGTGGCCAACAAGCCCAACCTTAAAGATACTGCTTCCTGAGTCTTCGTGATGGTTATGTTGGATGATGTCGTGG
              201                                                                                                300
LPLAT5-ORF    ATTGATGCATCTTCTGTGGATCGAAGGATGGCTGTGTGGAGGATAATGGGTGCGGTCAAGGGGCAGGGTCAAATGGGCTAGTTTTATTGGGCTTATGCTC
LPLAT5-g      ATTGATGCATCTTCTGTGGATCGAAGGATGGCTGTGTGGAGGATAATGGGTGCGGTCAAGGGGCAGGGTCAAATGGGCTAGTTTTATTGGGCTTATGCTC
              301                                                                                                400
LPLAT5-ORF    CATATGAGGGTCAAG----------------------------------------------------------------------------------
LPLAT5-g      CATATGAGGGTCAAGGTAACGTTTGCCTTGCAGGCCCTTGAACCCTTGCTGTGTAGCTAGCCAAAGTCCTTCTGTCGCCCCCACACCCATGCCCTAACTG
              401                                                                                                500
LPLAT5-ORF    ----------------------------------AGATCCTGCACCTCGCTCTATCATTCCTTCACTCCTATATCATCGTGATGCAATTACAG
LPLAT5-g      TCATCTCCTTCGTGACTTCGACGACTATAGAGGATATAGAAGAGATCCTGCACCTCGCTCTATCATTCCTTCACTCCTATATCATCGTGATGCAATTACAG
              501                                                                                                600
LPLAT5-ORF    CTGGATCACACCGGTCCTGAAATGATTGTCAGCATGAAAGTCACCTCTTCGGGCTTGAATGTCTATCATGGCCGGGCTAACCGCAAAGC----------
LPLAT5-g      CTGGATCACACCGGTCCTGAAATGATTGTCAGCATGAAAGTCACCTCTTCGGGCTTGAATGTCTATCATGGCCGGGCTAACCGCAAAGGTAATAATGACAC
              601                                                                                                700
LPLAT5-ORF    ----------CCATCACGCTAGGAAAACGTTTATTATACATTTGAACGTCAAACTCACCCTCTCTTCTCGGTCGGAGGAACTCAGCAGAAGTCAGCAGAT
LPLAT5-g      CCATCACGCTAGGAAAACGTTTATTATACATTTGAACGTCAAACTCACCCTCTCTTCTCGGTCGGAGGAACTCAGCAGAAGTCAGCAGAT
              701                                                                                                800
LPLAT5-ORF    CTATCGTTCGGTTCGTTCCGTTCGTTCGACGTACGTCAGCAGTATCAGCAGGCAACGAAGACGAGGGGTCAGAATATATATCGATTATATCGGCTTCA
LPLAT5-g      CTATCGTTCGGTTCGTTCCGTTCGTTCGACGTACGTCAGCAGTATCAGCAGGCAACGAAGACGAGGGGTCAGAATATATATCGATTATATCGGCTTCA
```

```
           1601                                                                                    1700
LPLAT5-ORF CCAGTGAAGCGAAAGCCCAACAAAGAGCAGCAGCCCGAGCCTCCAGAGGTCAAAGGAAGTCAATGGATGATGATGTTGCCACAGGAGGTTGCCACCCGTCTCTG
LPLAT5-g   CCAGTGAAGCGAAAGCCCAACAAAGAGAAGCAGCCCGAGCCTCCAGAGGTCAAAGGAAGTCAATGGATGATGATGTTGCCAGGAGGTTGCCGACCCGTCTCTG
           1701                         1759
LPLAT5-ORF TGAGTGCTGCCAGCGAGCTGCTTGACACCTGTGGTCCAGTTAAAATCAAGACGGTG---
LPLAT5-g   TGAGTGGTGCCAGGGAGCTGCTTGCACACCTGTGGTTGCCAGTTAAAATCAAGACGGCCTGTAA
```

LYSOPHOSPHOLIPID ACYLTRANSFERASE

SEQUENCE LISTING

The instant application contains a Sequence Listing which has been submitted in ASCII format via EFS-Web and is hereby incorporated by reference in its entirety. Said ASCII copy, created on Nov. 16, 2011, is named P40741.txt and is 64,982 bytes in size.

TECHNICAL FIELD

The present invention relates to novel lysophospholipid acyltransferases.

BACKGROUND ART

Biosynthesis of Polyunsaturated Fatty Acids

Fatty acids are major components of lipids such as phospholipids and triacylglycerols. Fatty acids containing two or more unsaturated bonds are collectively referred to as polyunsaturated fatty acids (PUFAs), and are known to include arachidonic acid, dihomo-γ-linolenic acid, eicosapentaenoic acid, docosahexaenoic acid, etc. Various physiological activities have been reported for these fatty acids (non-patent document 1).

These polyunsaturated fatty acids are expected to find applications in various fields, but some of them cannot be synthesized in vivo in animals. This has led to development of methods for obtaining polyunsaturated fatty acids by culturing various microorganisms. Attempts to produce polyunsaturated fatty acids in plants have also been made. In such cases, polyunsaturated fatty acids are known to be accumulated as components of reserve lipids such as triacylglycerols, for example, in microbial cells or plant seeds.

Among the polyunsaturated fatty acids, arachidonic acid has attracted attention as an intermediate metabolite in the synthesis of prostaglandins, leukotrienes and the like, and many attempts have been made to apply it as a material for functional foods and medicaments. Furthermore, arachidonic acid is contained in breast milk so that it is important for the growth of infants, especially for the growth of fetal length and brain, and therefore, it also attracts attention in a nutritional aspect as a necessary component for the growth of infants as well as DHA (docosahexaenoic acid).

Arachidonic acid is biosynthesized by the pathway shown in FIG. 1. Specifically, arachidonic acid is produced through several chain elongation and desaturation steps from palmitic acid generated by de novo fatty acid synthesis. In this pathway, an elongase and Δ9 desaturase act on acyl-CoA. On the other hand, Δ12 desaturase, Δ6 desaturase and Δ5 desaturase are known to act on the acyl groups of phospholipids such as phosphatidylcholine (non-patent document 2). Thus, acyl transfer between acyl-CoA and phospholipids is required in the biosynthesis of PUFAs such as arachidonic acid. Without being limited to the biosynthesis of PUFAs, replacement of only fatty acids after biosynthesis of phospholipids is known as "remodeling" of phospholipids, and lysophospholipid acyltransferases (hereinafter referred to as "LPLATs") are known to be involved in this reaction (non-patent document 3).

Biosynthesis of Triacylglycerols

Among reserve lipids, triacylglycerols are synthesized in vivo as follows. Glycerol-3-phosphate is acylated with glycerol-3-phosphate acyltransferase (hereinafter sometimes referred to as "GPAT") at the hydroxyl group in the 1-position (Δ-position) to form lysophosphatidic acid (hereinafter sometimes referred to as "LPA"). LPA is a lysophospholipid containing only one acyl group, and is acylated with lysophosphatidic acid acyltransferase (hereinafter sometimes referred to as "LPAAT") to form phosphatidic acid (hereinafter sometimes referred to as "PA"). This PA is dephosphorylated by phosphatidic acid phosphatase to form diacylglycerol, which is in turn acylated with diacylglycerol acyltransferase (hereinafter sometimes referred to as "DGAT") to form triacylglycerol. Acyl-CoA: cholesterol acyltransferase (hereinafter sometimes referred to as "ACAT") and lysophosphatidylcholine acyltransferase (hereinafter sometimes referred to as "LPCAT") and the like are known to be indirectly involved in the biosynthesis of triacylglycerols.

Biosynthesis of Phospholipids

PA produced from LPA by the action of LPAAT as described above serves as a precursor in the biosynthesis of various phospholipids. For example, important phospholipids such as phosphatidylethanolamine (PE), phosphatidylcholine (PC), phosphatidylserine (PS), phosphatidylinositol (PI), and phosphatidylglycerol (PG) are biosynthesized from PA. Thus, PA is not only an intermediate in lipid synthesis, but also an intracellular and intercellular lipid mediator having a very wide range of biological and pharmacological effects such as cell proliferation, platelet aggregation, smooth muscle contraction, promotion of cancer invasion, etc.

Lysophospholipid Acyltransferases

As described above, LPLATs are believed to be involved in PUFA biosynthesis. The LPLATs collectively refer to enzymes having the activity of introducing an acyl group into lysophospholipids, and include those having various names based on the specificity for the substrate, i.e., the molecular species of the lysophospholipid used as a substrate. One example is LPAAT that is involved in the synthesis of triacylglycerols and phospholipids using LPA as a substrate. Other lysophospholipids on which LPLATs act include lysophosphatidylcholine (LPC), lysophosphatidylserine (LPS), lysophosphatidylethanolamine (LPE), lysophosphatidylinositol (LPI), etc. Thus, the enzymes are called LPAAT, LPCAT, lysophosphatidylserine acyltransferase (LPSAT), lysophosphatidylinositol acyltransferase (LPLAT) and the like based on the molecular species on which they act. Each enzyme may specifically act on one lysophospholipid or multiple specific lysophospholipids. For example, LPLATs called as LPAAT include those acting on not only LPA but also LPC, LPE, etc.

Sequence Profile-Based Classification of Lysophospholipid Acyltransferases

LPLATs are classified as glycerophospholipid acyltransferases. The glycerophospholipid acyltransferases are thought to fall into three groups from amino acid sequence comparison, i.e., LPAAT family, MBOAT (membrane-bound O-acyltransferase) family and DGAT2 family (non-patent document 5). Enzymes belonging to the LPAAT family are commonly characterized by a membrane-bound domain and a sequentially conserved motif (LPAAT motif). The enzymes belonging to the LPAAT family members include LPAAT, GPAT, etc. Enzymes included in the MBOAT family are commonly characterized by a membrane-bound domain. The MBOAT family is known to include DGAT, ACAT and the like in addition to LPLAT. In animals or the like, some enzymes belonging to the MBOAT family are thought to be responsible for the remodeling reaction critical for membrane phospholipid synthesis.

LPLATs have been reported in a broad spectrum of organisms from unicellular organisms such as bacteria and yeast to higher organisms such as mammals. In yeast (*Saccharomyces cerevisiae*) belonging to fungi, SLC1 (YDL052C) and SLC4

(YOR175C) (herein sometimes referred to as "ALE1" or "LPT1") are known as membrane-bound LPLAT genes (non-patent document 5). In animals, multiple LPLAT homologs are known to exist, including those responsible for the reaction of acting on LPA in the de novo triglyceride synthesis system to yield PA and those responsible for phospholipid remodeling (non-patent document 6).

In the lipid-producing fungus *Mortierella alpina* (hereinafter sometimes referred to as "*M. alpina*"), four LPLATs have been Obtained, all of which belong to the LPAAT family (patent documents 1-3). However, no report shows that any LPLAT belonging to the MBOAT family has been obtained from *M. alpina*.

REFERENCES

Patent Documents

Patent document 1: International Publication No. WO2004/087902
Patent document 2: U.S. Patent Application Publication No. US2006/0094090
Patent document 3: International Publication No. WO2008/146745

Non-Patent Documents

Non-patent document 1: Lipids, 39, 1147 (2004)
Non-patent document 2: J.B.C., 278(37), 35115-35126, (2003)
Non-patent document 3: J.B.C., 276(29), 26745-26752, (2001)
Non-patent document 4: Proc. Natl. Acad. Sci., 105(8), 2830-2835, (2008)
Non-patent document 5: J.B.C., 282(42), 30845-30855, (2007)
Non-patent document 6: J.B.C., 284(1), 1-5, (2009)
Non-patent document 7: Trends Biochem. Sci., 25, 111-112, (2000)
Non-patent document 8: Journal of lipid research 2009 R80035 JLR200v1

SUMMARY OF INVENTION

Technical Problems

As described above, phospholipid remodeling is essential in the biosynthesis of PUFAs such as arachidonic acid, and LPLATs may be involved in this reaction. However, the LPAAT homologs hitherto known had the disadvantage that the proportion of PUFAs in total fatty acids could not be sufficiently increased even if they were transferred and expressed in host organisms. Therefore, there is a need to identify novel nucleic acid and protein that would sufficiently increase the proportion of PUFAs in total fatty acids in a host when they are transferred and expressed in the host. There is also a need to identify a nucleic acid and protein capable of producing fats with a high content of industrially valuable fatty acids and to develop a method by which valuable fatty acids can be produced or the content of valuable fatty acids can be increased by using them.

Solution to Problems

An object of the present invention is to provide proteins and nucleic acids capable of producing valuable fats by expressing them in a host cell to influence lipid metabolism of the host or to increase the content of a desired fatty acid.

In the biosynthesis of PUFAs such as arachidonic acid, phospholipid remodeling is essential. The lipid-producing fungus *M. alpina* can accumulate large quantities of valuable PUFAs such as arachidonic acid, but any acyltransferase belonging to the MBOAT family involved in lipid remodeling as reported in animals or the like has not been obtained from *M. alpina*. The inventor recognized this point and carefully studied to attain the above object, with the result that the inventor obtained cDNA encoding an enzyme belonging to the MBOAT family from *M. alpina*. Further, the inventor attempted to produce a fatty acid composition by transforming the resulting cDNA into a highly proliferative host cell such as yeast to find that the host cell can produce a different fatty acid composition, especially a fatty acid composition having a high proportion of arachidonic acid as compared with fatty acid compositions produced by hosts transformed with vectors containing nucleic acids encoding known LPAATs obtained from *M. alpina*. Thus, the inventor succeeded in cloning genes for novel LPLATs different from known LPAATs and finally accomplished the present invention.

Accordingly, the present invention provides the following aspects.
(1) A nucleic acid of any one of (a)-(e) below:
(a) a nucleic acid that comprises a nucleotide sequence encoding a protein consisting of an amino acid sequence with deletion, substitution or addition of one or more amino acids in the amino acid sequence shown in SEQ ID NO: 2 or 7, and having lysophospholipid acyltransferase activity;
(b) a nucleic acid that hybridizes under stringent conditions to a nucleic acid consisting of a nucleotide sequence complementary to the nucleotide sequence consisting of SEQ ID NO: 1 or 6 and that comprises a nucleotide sequence encoding a protein having lysophospholipid acyltransferase activity;
(c) a nucleic acid that comprises a nucleotide sequence sharing an identity of 80% or more with the nucleotide sequence consisting of SEQ ID NO: 1 or 6 and encoding a protein having lysophospholipid acyltransferase activity;
(d) a nucleic acid that comprises a nucleotide sequence encoding a protein consisting of an amino acid sequence sharing an identity of 80% or more with the amino acid sequence consisting of SEQ ID NO: 2 or 7 and having lysophospholipid acyltransferase activity; and
(e) a nucleic acid that hybridizes under stringent conditions to a nucleic acid consisting of a nucleotide sequence complementary to a nucleotide sequence encoding a protein consisting of the amino acid sequence shown in SEQ ID NO: 2 or 7 and that comprises a nucleotide sequence encoding a protein having lysophospholipid acyltransferase activity.
(2) The nucleic acid of (1), which is any one of (a)-(e) below:
(a) a nucleic acid that comprises a nucleotide sequence encoding a protein consisting of a variant of the amino acid sequence shown in SEQ ID NO: 2 or 7 in which 1-50 amino acids are deleted, substituted or added, and having lysophospholipid acyltransferase activity;
(b) a nucleic acid that hybridizes under conditions of 2×SSC, 50° C. to a nucleic acid consisting of a nucleotide sequence complementary to the nucleotide sequence consisting of SEQ ID NO: 1 or 6 and that comprises a nucleotide sequence encoding a protein having lysophospholipid acyltransferase activity;
(c) a nucleic acid that comprises a nucleotide sequence sharing an identity of 90% or more with the nucleotide sequence consisting of SEQ ID NO: 1 or 6 and encoding a protein having lysophospholipid acyltransferase activity;

(d) a nucleic acid that comprises a nucleotide sequence encoding a protein consisting of an amino acid sequence sharing an identity of 90% or more with the amino acid sequence consisting of SEQ ID NO: 2 or 7 and having lysophospholipid acyltransferase activity; and (e) a nucleic acid that hybridizes under conditions of 2×SSC, 50° C. to a nucleic acid consisting of a nucleotide sequence complementary to a nucleotide sequence encoding a protein consisting of the amino acid sequence shown in SEQ ID NO: 2 or 7 and that comprises a nucleotide sequence encoding a protein having lysophospholipid acyltransferase activity.

(3) A nucleic acid of any one of (a)-(e) below:

(a) a nucleic acid that comprises a nucleotide sequence encoding a protein consisting of an amino acid sequence with deletion, substitution or addition of one or more amino acids in the amino acid sequence shown in SEQ ID NO: 2 or 7, and having the activity of increasing the proportion of arachidonic acid in the compositional ratio of fatty acids in a host transformed with a recombinant vector containing the nucleic acid as compared with the proportion in the compositional ratio of fatty acids in a host that has not been transformed with the vector;

(b) a nucleic acid that hybridizes under stringent conditions to a nucleic acid consisting of a nucleotide sequence complementary to the nucleotide sequence consisting of SEQ ID NO: 1 or 6 and that comprises a nucleotide sequence encoding a protein having the activity of increasing the proportion of arachidonic acid in the compositional ratio of fatty acids in a host transformed with a recombinant vector containing the nucleic acid as compared with the proportion in the compositional ratio of fatty acids in a host that has not been transformed with the vector;

(c) a nucleic acid that comprises a nucleotide sequence sharing an identity of 80% or more with the nucleotide sequence consisting of SEQ ID NO: 1 or 6 and encoding a protein having the activity of increasing the proportion of arachidonic acid in the compositional ratio of fatty acids in a host transformed with a recombinant vector containing the nucleic acid as compared with the proportion in the compositional ratio of fatty acids in a host that has not been transformed with the vector;

(d) a nucleic acid that comprises a nucleotide sequence encoding a protein consisting of an amino acid sequence sharing an identity of 80% or more with the amino acid sequence consisting of SEQ ID NO: 2 or 7 and having the activity of increasing the proportion of arachidonic acid in the compositional ratio of fatty acids in a host transformed with a recombinant vector containing the nucleic acid as compared with the proportion in the compositional ratio of fatty acids in a host that has not been transformed with the vector; and (e) a nucleic acid that hybridizes under stringent conditions to a nucleic acid consisting of a nucleotide sequence complementary to a nucleotide sequence encoding a protein consisting of the amino acid sequence shown in SEQ ID NO: 2 or 7 and that comprises a nucleotide sequence encoding a protein having the activity of increasing the proportion of arachidonic acid in the compositional ratio of fatty acids in a host that has not been transformed with the vector.

(4) The nucleic acid of (3), which is any one of (a)-(e) below:

(a) a nucleic acid that comprises a nucleotide sequence encoding a protein consisting of an amino acid sequence with deletion, substitution or addition of 1-50 amino acids in the amino acid sequence shown in SEQ ID NO: 2 or 7, and having the activity of increasing the proportion of arachidonic acid in the compositional ratio of fatty acids in a host transformed with a recombinant vector containing the nucleic acid as compared with the proportion in the compositional ratio of fatty acids in a host that has not been transformed with the vector;

(b) a nucleic acid that hybridizes under conditions of 2×SSC, 50° C. to a nucleic acid consisting of a nucleotide sequence complementary to the nucleotide sequence consisting of SEQ ID NO: 1 or 6 and that comprises a nucleotide sequence encoding a protein having the activity of increasing the proportion of arachidonic acid in the compositional ratio of fatty acids in a host transformed with a recombinant vector containing the nucleic acid as compared with the proportion in the compositional ratio of fatty acids in a host that has not been transformed with the vector;

(c) a nucleic acid that comprises a nucleotide sequence sharing an identity of 90% or more with the nucleotide sequence consisting of SEQ ID NO: 1 or 6 and encoding a protein having the activity of increasing the proportion of arachidonic acid in the compositional ratio of fatty acids in a host transformed with a recombinant vector containing the nucleic acid as compared with the proportion in the compositional ratio of fatty acids in a host that has not been transformed with the vector;

(d) a nucleic acid that comprises a nucleotide sequence encoding a protein consisting of an amino acid sequence sharing an identity of 90% or more with the amino acid sequence consisting of SEQ ID NO: 2 or 7 and having the activity of increasing the proportion of arachidonic acid in the compositional ratio of fatty acids in a host transformed with a recombinant vector containing the nucleic acid as compared with the proportion in the compositional ratio of fatty acids in a host that has not been transformed with the vector; and (e) a nucleic acid that hybridizes under conditions of 2×SSC, 50° C. to a nucleic acid consisting of a nucleotide sequence complementary to a nucleotide sequence encoding a protein consisting of the amino acid sequence shown in SEQ ID NO: 2 or 7 and that comprises a nucleotide sequence encoding a protein having the activity of increasing the proportion of arachidonic acid in the compositional ratio of fatty acids in a host transformed with a recombinant vector containing the nucleic acid as compared with the proportion in the compositional ratio of fatty acids in a host that has not been transformed with the vector.

(5) The nucleic acid of any one of (1)-(4) wherein the encoded protein belongs to the membrane-bound O-acyltransferase family.

(6) A nucleic acid of any one of (a)-(d) below:

(a) a nucleic acid that comprises the nucleotide sequence shown in SEQ ID NO: 1 or 6 or a partial sequence thereof;

(b) a nucleic acid that comprises a nucleotide sequence encoding a protein consisting of the amino acid sequence shown in SEQ ID NO: 2 or 7 or a partial sequence thereof;

(c) a nucleic acid that comprises the nucleotide sequence shown in SEQ ID NO: 4 or 9 or a partial sequence thereof; and (d) a nucleic acid that comprises the nucleotide sequence shown in SEQ ID NO: 5 or 10 or a partial sequence thereof.

(7) A protein of (a) or (b) below:

(a) a protein consisting of an amino acid sequence with deletion, substitution or addition of one or more amino acids in a variant of the amino acid sequence of SEQ ID NO: 2 or 7, and having lysophospholipid acyltransferase activity; or (b) a protein consisting of an amino acid sequence sharing an identity of 80% or more with the amino acid sequence consisting of SEQ ID NO: 2 or 7 and having lysophospholipid acyltransferase activity.

(8) The protein of (7), which is (a) or (b) below:
(a) a protein consisting of an amino acid sequence with deletion, substitution or addition of 1-50 amino acids in the amino acid sequence of SEQ ID NO: 2 or 7, and having lysophospholipid acyltransferase activity; or
(b) a protein consisting of an amino acid sequence sharing an identity of having 90% or more with the amino acid sequence consisting of SEQ ID NO: 2 or 7 and having lysophospholipid acyltransferase activity.
(9) A protein of (a) or (b) below:
(a) a protein consisting of an amino acid sequence with deletion, substitution or addition of one or more amino acids in the amino acid sequence of SEQ ID NO: 2 or 7, and having the activity of increasing the proportion of arachidonic acid in the compositional ratio of fatty acids in a host transformed with a recombinant vector containing a nucleic acid encoding the amino acid sequence as compared with the proportion in the compositional ratio of fatty acids in a host that has not been transformed with the vector; or
(b) a protein consisting of an amino acid sequence sharing an identity of 80% or more with the amino acid sequence consisting of SEQ ID NO: 2 or 7 and having the activity of increasing the proportion of arachidonic acid in the compositional ratio of fatty acids in a host transformed with a recombinant vector containing a nucleic acid encoding the amino acid sequence as compared with the proportion in the compositional ratio of fatty acids in a host that has not been transformed with the vector.
(10) The protein of (9), which is (a) or (b) below:
(a) a protein consisting of an amino acid sequence with deletion, substitution or addition of 1-50 amino acids in the amino acid sequence of SEQ ID NO: 2 or 7, and having the activity of increasing the proportion of arachidonic acid in the compositional ratio of fatty acids in a host transformed with a recombinant vector containing a nucleic acid encoding the amino acid sequence as compared with the proportion in the compositional ratio of fatty acids in a host that has not been transformed with the vector; or
(b) a protein consisting of an amino acid sequence sharing an identity of 90% or more with the amino acid sequence consisting of SEQ ID NO: 2 or 7 and having the activity of increasing the proportion of arachidonic acid in the compositional ratio of fatty acids in a host transformed with a recombinant vector containing a nucleic acid encoding the amino acid sequence as compared with the proportion in the compositional ratio of fatty acids in a host that has not been transformed with the vector.
(11) The protein of any one of (7)-(10), which belongs to the membrane-bound O-acyltransferase family.
(12) A protein consisting of the amino acid sequence shown in SEQ ID NO: 2 or 7.
(13) A recombinant vector containing the nucleic acid of any one of (1)-(6).
(14) A cell transformed with the recombinant vector of (13).
(15) A fatty acid composition obtained by culturing the transformed cell of (14) wherein the proportion of arachidonic acid in the compositional ratio of fatty acids in said fatty acid composition is higher than the proportion of arachidonic acid in the fatty acid composition obtained by culturing a non-transformed host.
(16) A method for preparing a fatty acid composition, comprising collecting the fatty acid composition of (15) from cultures of the transformed cell of (14).
(17) A food product comprising the fatty acid composition of (15).
(18) A method for using the recombinant vector of (13) to increase the proportion of arachidonic acid in the compositional ratio of fatty acids in a host transformed with the vector as compared with the proportion in compositional ratio of fatty acids in a host that has not been transformed with the vector.
(19) A nucleic acid of any one of (a)-(e) below:
(a) a nucleic acid that comprises a nucleotide sequence encoding a protein consisting of an amino acid sequence with deletion, substitution or addition of one or more amino acids in the amino acid sequence shown in SEQ ID NO: 2 or 7, and involved in the conversion from 18:3(n-6)-PL to 18:3(n-6)-CoA and/or conversion from DGLA-CoA to DGLA-PL;
(b) a nucleic acid that hybridizes under stringent conditions to a nucleic acid consisting of a nucleotide sequence complementary to the nucleotide sequence consisting of SEQ ID NO: 1 or 6 and that comprises a nucleotide sequence encoding a protein involved in the conversion from 18:3(n-6)-PL to 18:3(n-6)-CoA and/or conversion from DGLA-CoA to DGLA-PL;
(c) a nucleic acid that comprises a nucleotide sequence sharing an identity of 80% or more with the nucleotide sequence consisting of SEQ ID NO: 1 or 6 and encoding a protein involved in the conversion from 18:3(n-6)-PL to 18:3(n-6)-CoA and/or conversion from DGLA-CoA to DGLA-PL;
(d) a nucleic acid that comprises a nucleotide sequence encoding a protein consisting of an amino acid sequence sharing an identity of 80% or more with the amino acid sequence consisting of SEQ ID NO: 2 or 7 and involved in the conversion from 18:3(n-6)-PL to 18:3(n-6)-CoA and/or conversion from DGLA-CoA to DGLA-PL; and
(e) a nucleic acid that hybridizes under stringent conditions to a nucleic acid consisting of a nucleotide sequence complementary to a nucleotide sequence encoding a protein consisting of the amino acid sequence shown in SEQ ID NO: 2 or 7 and that comprises a nucleotide sequence encoding a protein involved in the conversion from 18:3(n-6)-PL to 18:3(n-6)-CoA and/or conversion from DGLA-CoA to DGLA-PL.
(20) A protein of (a) or (b) below:
(a) a protein consisting of an amino acid sequence with deletion, substitution or addition of one or more amino acids in the amino acid sequence of SEQ ID NO: 2 or 7, and involved in the conversion from 18:3(n-6)-PL to 18:3(n-6)-CoA and/or conversion from DGLA-CoA to DGLA-PL; or
(b) a protein consisting of an amino acid sequence sharing an identity of 80% or more with the amino acid sequence consisting of SEQ ID NO: 2 or 7 and involved in the conversion from 18:3(n-6)-PL to 18:3(n-6)-CoA and/or conversion from DGLA-CoA to DGLA-PL.

Advantageous Effects of Invention

The LPLATs of the present invention allows an improvement in the ability to produce fatty acids, such as arachidonic acid, and/or reserve lipids, and hence is preferred as means for improving the productivity of polyunsaturated fatty acids in microorganisms and plants. Thus, they can provide lipids having desired characteristics or effects so that they can be usefully applied for use in foods, cosmetics, pharmaceuticals, soaps, etc.

BRIEF DESCRIPTION OF DRAWINGS

In FIG. 1, the abbreviations have the following meanings: PL, phospholipid; CoA, coenzyme A; DS, desaturase (fatty acid desaturase enzyme); GLELO, fatty acid elongase; 18:0, stearoyl group; 18:1, oleoyl group; 18:2, lilnoyl group; 18:3(n-6), γ-lilnoleyl group; DGLA, dihomo-γ-lilnoleyl group; ARA, arachidoyl group.

FIG. 2 shows the full-length cDNA sequence (SEQ ID NO: 4) of LPLAT5 from *M. alpina* strain 1S-4 and the amino acid sequence (SEQ ID NO: 2) deduced therefrom.

FIG. 3 shows the full-length cDNA sequence (SEQ ID NO: 9) of LPLAT6 from *M. alpina* strain 1S-4 and the amino acid sequence (SEQ ID NO: 7) deduced therefrom.

FIG. 4A shows a comparison between the genomic sequence (SEQ ID NO: 5) and the ORF sequence (SEQ ID NO: 1) of LPLAT5 from *M. alpina* strain 1S-4.

FIG. 4B shows a comparison between the genomic sequence (SEQ ID NO: 5_continued) and the ORF sequence (SEQ ID NO: 1 continued) of LPLAT5 from *M. alpina* strain 1S-4.

FIG. 4C shows a comparison between the genomic sequence (SEQ ID NO: 5_continued) and the ORF sequence (SEQ ID NO: 1 continued) of LPLAT5 from *M. alpina* strain 1S-4.

FIG. 5A shows a comparison between the genomic sequence (SEQ ID NO: 10) and the ORF sequence (SEQ ID NO: 6) of LPLAT6 from *M. alpina* strain 1S-4.

FIG. 5B shows a comparison between the genomic sequence (SEQ ID NO: 10_continued) and the ORF sequence (SEQ ID NO: 6 continued) of LPLAT6 from *M. alpina* strain 1S-4.

FIG. 5C shows a comparison between the genomic sequence (SEQ ID NO: 10_continued) and the ORF sequence (SEQ ID NO: 6 continued) of LPLAT6 from *M. alpina* strain 1S-4.

In FIG. 6, the abbreviations have the following meanings: GLA, γ-linolenic acid; DGLA, dihomo-γ-linolenic acid; ARA, arachidonic acid.

In FIG. 7, the abbreviations have the following meanings: GLA, γ-linolenic acid; DGLA, dihomo-γ-linolenic acid; ARA, arachidonic acid.

In FIG. 8, the abbreviations have the following meanings: GLA, γ-linolenic acid; DGLA, dihomo-γ-linolenic acid; ARA, arachidonic acid.

DESCRIPTION OF EMBODIMENT

Figure 1:
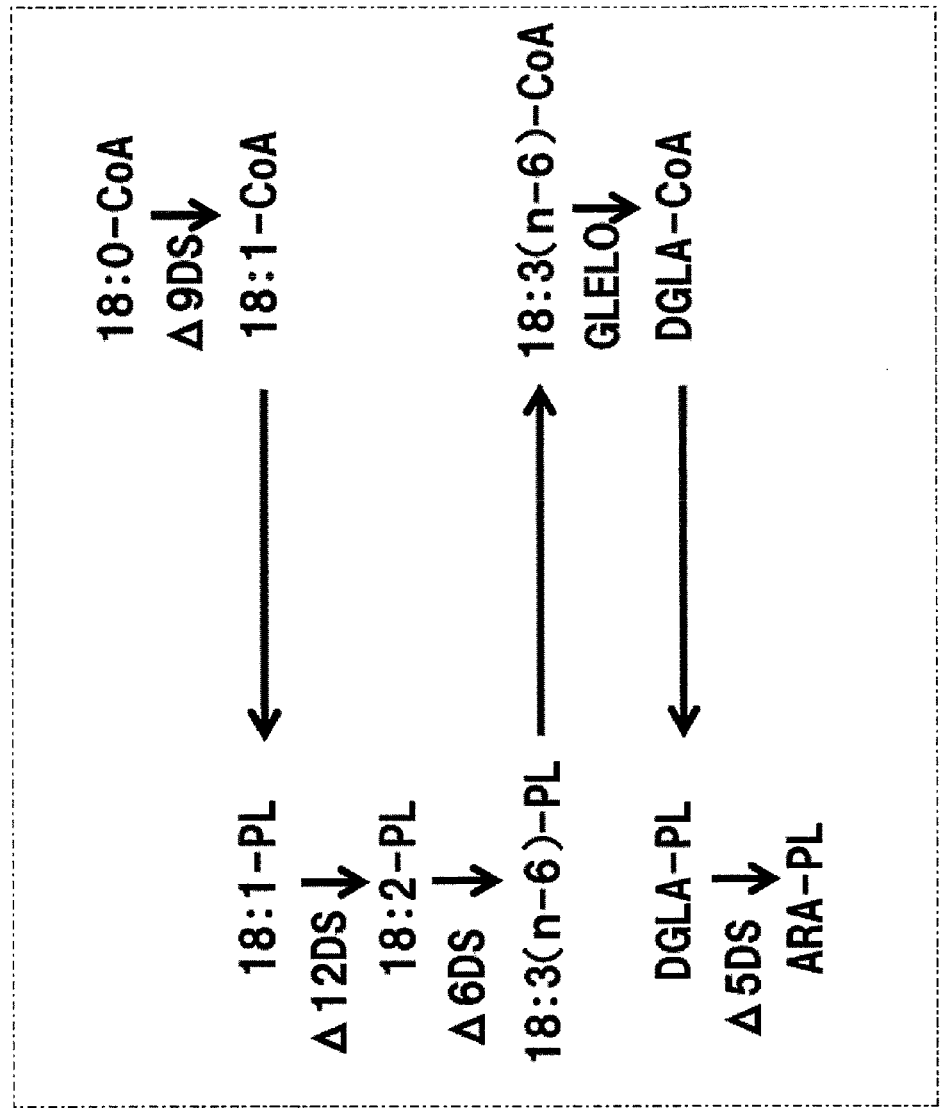
FIG. 1 is a schematic diagram showing the biosynthetic pathway of arachidonic acid.

The present invention relates to novel lysophospholipid acyltransferases ("LPLATs") from the genus *Mortierella* characterized by transferring an acyl group between acyl-CoA and phospholipids in the biosynthetic process of arachidonic acid. The proteins of the present invention can act on lysophospholipids. The acyl donor is typically acyl-CoA, but not limited thereto.

Embodiments of the present invention are specifically described below.

Nucleic Acids Encoding Lysophospholipid Acyltransferases of the Present Invention Lysophospholipid acyltransferases (LPLATs) encoded by the nucleic acids of the present invention include LPLAT5 and 6 as typical examples. Unlike fatty acid compositions produced by hosts expressing known LPAATs from *M. alpina*, LPLAT5 and 6 could produce fatty acid compositions characterized by a high proportion of arachidonic acid, as explained in the Examples below. Therefore, the LPLATs of the present invention preferably produce arachidonic acid with very high efficiency as compared with known LPAATs from *M. alpina*.

Relationship of the cDNA, CDS, ORF of the nucleic acids encoding LPLAT5 and LPLAT6 of the present invention and amino acid sequences is summarized in Table 1 below.

TABLE 1

|  | LPLAT5 | | LPLAT6 | |
| --- | --- | --- | --- | --- |
|  | SEQ ID NO: | Corresponding region in SEQ ID NO: 4 | SEQ ID NO: | Corresponding region in SEQ ID NO: 9 |
| ORF | SEQ ID NO: 1 | 161-1690 | SEQ ID NO: 6 | 38-1756 |
| Amino acid sequence | SEQ ID NO: 2 | ***** | SEQ ID NO: 7 | ***** |
| CDS | SEQ ID NO: 3 | 161-1693 | SEQ ID NO: 8 | 38-1759 |
| cDNA | SEQ ID NO: 4 | ***** | SEQ ID NO: 9 | ***** |

In summary, sequences related to LPLAT5 of the present invention include SEQ ID NO: 1 representing the sequence of the ORF region of LPLAT5; SEQ ID NO: 2 representing the amino acid sequence of LPLAT5; SEQ ID NO: 3 representing the sequence of the CDS region of LPLAT5; SEQ ID NO: 4 representing the nucleotide sequence of the cDNA; and SEQ ID NO: 5 representing the genomic sequence. More specifically, nucleotides 161-1693 of SEQ ID NO: 4 representing the cDNA sequence of LPLAT5 corresponds to the CDS (SEQ ID NO: 3), and nucleotides 161-1690 corresponds to the ORF (SEQ ID NO: 1). The cDNA sequence of LPLAT5 and its deduced amino acid sequence are shown in FIG. 2. The genomic sequence of (SEQ ID NO: 5) LPLAT5 contains two introns and exon regions corresponding to nucleotides 1-314, 461-587 and 668-1759 of SEQ ID NO: 5.

Similarly, sequences related to LPLAT6 of the present invention include SEQ ID NO: 6 representing the sequence of the ORF region of LPLAT6; SEQ ID NO: 7 representing the amino acid sequence of LPLAT6; SEQ ID NO: 8 representing the sequence of the CDS region of LPLAT6; SEQ ID NO: 9 representing the nucleotide sequence of the cDNA; and SEQ ID NO: 10 representing the genomic sequence. More specifically, nucleotides 38-1759 of SEQ ID NO: 9 representing the cDNA sequence of LPLAT6 corresponds to the CDS (SEQ ID NO: 8), and nucleotides 38-1756 corresponds to the ORF (SEQ ID NO: 6). The cDNA sequence of LPLAT6 and its deduced amino acid sequence are shown in FIG. 3. The genomic sequence (SEQ ID NO: 10) of LPLAT6 contains one intron and exon regions corresponding to nucleotides 1-1095 and 1318-1944 of SEQ ID NO: 10.

The nucleic acids of the present invention include single-stranded and double-stranded DNAs as well as RNA complements thereof, and may be either naturally occurring or artificially prepared. DNAs include, but are not limited to, genomic DNAs, cDNAs corresponding to the genomic DNAs, chemically synthesized DNAs, PCR-amplified DNAs and combinations thereof, as well as DNA/RNA hybrids, for example.

Preferred embodiments of the nucleic acids of the present invention include (a) a nucleic acid that comprises the nucleotide sequence shown in SEQ ID NO: 1 or 6; (b) a nucleic acid that comprises a nucleotide sequence encoding a protein consisting of the amino acid sequence shown in SEQ ID NO: 2 or 7; (c) a nucleic acid that comprises the nucleotide sequence shown in SEQ ID NO: 4 or 9; or (d) a nucleic acid that comprises the nucleotide sequence shown in SEQ ID NO: 5 or 10, etc.

To obtain the above nucleotide sequences, nucleotide sequence data of EST or genomic DNA from an organism having LPLAT activity can also be searched for nucleotide sequences encoding proteins sharing high identity to a known protein having LPLAT activity. The organism having LPLAT activity is preferably a lipid-producing fungus such as, but not limited to, *M. alpina*.

To perform EST analysis, a cDNA library is first constructed. Procedures for cDNA library construction can be found in "Molecular Cloning, A Laboratory Manual 3rd ed." (Cold Spring Harbor Press (2001)). Commercially available cDNA library construction kits may also be used. A procedure for constructing a cDNA library suitable for the present invention is as follows, for example. That is, an appropriate strain of the lipid-producing fungus *M. alpina* is inoculated into an appropriate medium and precultured for an appropriate period. The cultures are collected at appropriate time points during the main cultivation and cells are harvested to prepare total RNA. Total RNA can be prepared using a known technique such as the guanidine hydrochloride/CsCl method. Poly(A)$^+$RNA can be purified from the resulting total RNA using a commercially available kit. Further, a cDNA library can be constructed using a commercially available kit. Then, ESTs can be obtained by determining the nucleotide sequences of any clones from the constructed cDNA library, by using primers designed to allow sequencing of an insert on a vector. For example, directional cloning can be performed when the cDNA library has been constructed using a ZAP-cDNA GigapackIII Gold Cloning Kit (STRATAGENE).

As a result of homology analysis of SEQ ID NOs: 1 and 6 using BLASTX against amino acid sequences deposited in GenBank, the amino acid sequence deduced from SEQ ID NO: 1 shows homology to LPLAT homologs from fungi and the amino acid sequence deduced from SEQ ID NO: 6 shows homology to LPLAT homologs from animals. The nucleotide sequence identity and amino acid sequence identity of the sequence showing the highest identity to the ORF of each sequence were determined by clustalW, revealing that a lysophospholipid acyltransferase homolog from *Schizosaccharomyces pombe* (GI:161085648) showed the lowest E-value or the highest identity to SEQ ID NO: 1 and the nucleotide sequence identity and amino acid sequence identity in ORF were 43.2% and 33.3%, respectively. Similarly, a putative protein from *Xenopus laevis* (GI:56788919) showed the highest identity to SEQ ID NO: 6 and the nucleotide sequence identity and amino acid sequence identity in ORF were 41.2% and 28.6%, respectively.

The nucleotide sequence identity and amino acid sequence identity in ORF between LPLAT5 and LPLAT6 are 40.0% and 19.1%, respectively.

The present invention also encompasses nucleic acids functionally equivalent to nucleic acids that comprise the nucleotide sequences shown in SEQ ID NOs: 1 and 6 above (herein sometimes referred to as "nucleotide sequences of the present invention") and nucleotide sequences encoding proteins consisting of the amino acid sequences shown in SEQ ID NO: 2 and 7 (herein sometimes referred to as "amino acid sequences of the present invention"). The expression "functionally equivalent" means that a protein encoded by a nucleotide sequence of the present invention and a protein consisting of an amino acid sequence of the present invention have "lysophospholipid acyltransferase activity (LPLAT activity)", "the activity of increasing the proportion of arachidonic acid in the compositional ratio of fatty acids in a host transformed with a recombinant vector containing a nucleic acid encoding a protein of the present invention as compared with the proportion in the compositional ratio of fatty acids in a host that has not been transformed with the vector" (hereinafter sometimes referred to as "the activity of increasing the proportion of arachidonic acid")", and/or "the activity involved in one or more conversions selected from the group consisting of the conversion from 18:1-CoA to 18:1-PL, conversion from 18:3(n-6)-PL to 18:3(n-6)-CoA, and conversion from DGLA-CoA to DGLA-PL (hereinafter sometimes referred to as "the activity involved in the biosynthetic pathway of arachidonic acid")". Preferably, it means that the proteins have an activity similar to that of LPLAT5 and/or 6.

The "lysophospholipid acyltransferase (LPLAT) activity" of the present invention refers to the activity of transferring an acyl group between acyl-CoA and a lysophospholipid. "Lysophospholipid" refers to a lipid having one acyl group removed from a phospholipid. As used herein, lysophospholipids include, but not specifically limited to, lysophosphatidic acid (LPA), lysophosphatidylcholine (LPC), lysophosphatidylserine (LPS), lysophosphatidylethanolamine (LPE), lysophosphatidylinositol (LPI), etc.

The LPLATs of the present invention may specifically act on one lysophospholipid or multiple specific lysophospholipids.

The LPLAT activity of the present invention can be assayed by known methods including, for example, the method described in J.B.C., 282(47), 34288-34298 (2007).

The "activity of increasing the proportion of arachidonic acid" of the present invention refers to the activity of increasing the proportion of arachidonic acid in the compositional ratio of fatty acids in a host transformed with a recombinant vector containing a nucleic acid of the present invention as compared with the proportion in the compositional ratio of fatty acids in a host that has not been transformed with the vector, as described above. Specifically, it refers to the activity of increasing the proportion of arachidonic acid in the compositional ratio of fatty acids of a host transformed with a recombinant vector containing a nucleic acid that comprises a nucleotide sequence of the present invention or a nucleic acid that comprises a nucleotide sequence encoding a protein consisting of an amino acid sequence of the present invention as compared with the proportion in the compositional ratio of fatty acids in a host that has not been transformed with the vector. The activity can be assayed by known methods comprising, for example, transforming an expression vector pYE22m containing a nucleotide sequence of the present invention or the like into a recombinant host of yeast *Saccharomyces cerevisiae* capable of producing arachidonic acid by introducing and expressing Δ12 fatty acid desaturase gene, Δ6 fatty acid desaturase gene, GLELO fatty acid elongase gene, and Δ5 fatty acid desaturase gene; culturing the resulting transformant; harvesting the cultured cells; and subjecting them to fatty acid analysis by the procedure described in the Examples below.

The "activity involved in the biosynthetic pathway of arachidonic acid" of the present invention refers to the activity involved in the conversion from 18:1-CoA to 18:1-PL, conversion from 18:3(n-6)-PL to 18:3(n-6)-CoA, and/or conversion from DGLA-CoA to DGLA-PL. Preferably, the activity refers to the activity involved in the conversion from 18:3(n-6)-PL to 18:3(n-6)-CoA, and/or the conversion from DGLA-CoA from DGLA-PL. Here, 18:1- represents an oleoyl group, 18:3(n-6)- represents a γ-lilnoleyl group, DGLA- represents a dihomo-γ-lilnoleyl group, PL represents a phospholipid, and CoA represents coenzyme A, respectively.

Therefore, DGLA-CoA refers to acyl-CoA containing a dihomo-γ-lilnoleyl group, and DGLA-PL refers to a phospholipid containing a dihomo-γ-lilnoleyl group, for example. The activity involved in the biosynthetic pathway of arachidonic acid can be identified by observing the conversion from each starting substrate to the produced substrate. Alternatively, it can be identified by observing that a protein of the present invention is overexpressed in a host or cell transformed with a recombinant vector containing a nucleic acid encoding a protein of the present invention or the expression of the protein is suppressed in a cell capable of producing arachidonic acid. For example, it can be identified by analyzing the compositional ratio of fatty acids in a host or cell overexpressing a protein of the present invention or a host or cell underexpressing a protein of the present invention and observing changes in the compositional ratio of fatty acids to assess the conversion from each starting substrate to the produced substrate by the procedure described in the Examples below.

More preferably, the nucleotide sequences of the present invention or the like are nucleic acids that comprise a nucleotide sequence encoding a protein having LPLAT activity, the activity of increasing the proportion of arachidonic acid, and/or the activity involved in the biosynthetic pathway of arachidonic acid.

Still more preferably, the lysophospholipid acyltransferases (LPLATs) encoded by the nucleic acids of the present invention refer to enzymes belonging to the membrane-bound O-acyltransferase (MBOAT) family among LPLATs.

The "MBOAT family" refers to a family belonging to the protein of PFAM accession number PF03062, and refers to a group of enzymes having a transmembrane domain in the amino acid sequence of glycerophospholipid acyltransferases. PFAM (pfam.sanger.ac.uk/) refers to a database of profiles obtained by protein family alignments provided by Sanger Institute. Each profile is composed of similar sequences and analyzed by a hidden Markov model. The protein family to which a desired protein belongs can be searched using keywords, the nucleic acid sequence encoding the protein, the amino acid sequence of the protein, the accession number and the like, in addition to the protein name of interest. Search using the nucleic acid sequences encoding the LPLATs obtained by the present invention or the amino acid sequences of the LPLATs reveals that the proteins belong to the MBOAT family of accession number PF03062. Moreover, enzymes belonging to the MBOAT family have a conserved histidine residue in common at the active center, such as the histidine residue at position 317 in the amino acid sequence of LPLAT5, and the histidine residue at position 456 in the amino acid sequence of LPLAT6, for example.

Unlike the LPAAT family, the MBOAT family does not contain the LPAAT motif. The LPAAT motif refers to the conserved motif "HXXXXD (HX$_4$D)" occurring at four sites in the amino acid sequences of the LPAAT proteins described in patent document 3. For example, the LPAAT motif occurs at amino acid residues 115-120 of SEQ ID NO: 2 in patent document 3 in LPAAT3 and at amino acid residues 115-120 of SEQ ID NO: 4 in LPAAT4, which are from the lipid-producing fungus *M. alpina* described in patent document 3. However, the LPLAT proteins of the present invention contain no such motif.

In *M. alpina*, four LPLATs have been hitherto found (patent documents 1-3), but no LPLAT enzyme belonging to the MBOAT family has been found. Thus, the LPLATs of the present invention are most preferably LPLATs belonging to the MBOAT family and having the above activity of the present invention.

Nucleic acids functionally equivalent to the nucleic acids of the present invention as described above include a nucleic acid that comprises the nucleotide sequence of any one of (a)-(e) below. As used in reference to the nucleotide sequences herein below, "the above activity of the present invention" refers to the "LPLAT activity, the activity of increasing the proportion of arachidonic acid, and/or the activity involved in the biosynthetic pathway of arachidonic acid" defined above.

(a) A nucleic acid that comprises a nucleotide sequence encoding a protein consisting of an amino acid sequence with deletion, substitution or addition of one or more amino acids in the amino acid sequence shown in SEQ ID NO: 2 or 7, and having the above activity of the present invention.

The nucleic acid of the present invention comprises a nucleotide sequence encoding a protein consisting of an amino acid sequence with deletion, substitution or addition of one or more amino acids in the amino acid sequence shown in SEQ ID NO: 2 or 7, and having the above activity of the present invention. The "above activity of the present invention" is as described above.

Specifically, it comprises a nucleotide sequence encoding a protein consisting of an amino acid sequence with deletion, substitution and/or addition of one or more (preferably one or several (e.g., 1-400, 1-200, 1-100, 1-50, 1-30, 1-25, 1-20, 1-15, more preferably 10, 9, 8, 7, 6, 5, 4, 3, 2, or 1)) amino acids in the amino acid sequence shown in SEQ ID NO: 2 or 7; and having the above activity of the present invention. Here, the expression "amino acid sequence with deletion, substitution, and/or addition" means that one or more amino acids are deleted, substituted and/or added at one or more random positions in the same amino acid sequence. Two or more of the deletion, substitution and/or addition may occur at the same time, but the number of the deletion, substitution and/or addition is preferably smaller, in general.

In the above modifications, the substitution is preferably conservative. Conservative substitution refers to replacement of a particular amino acid residue by another residue having similar physicochemical characteristics, and may be any substitution that does not substantially affect the structural characteristics of the original sequence, e.g., it may be any substitution so far as the substituted amino acids do not disrupt a helix present in the original sequence or do not disrupt any other type of secondary structure characteristic of the original sequence.

Conservative substitution is typically introduced by synthesis in biological systems or chemical peptide synthesis, preferably by chemical peptide synthesis. Substituents here may include unnatural amino acid residues, as well as peptidomimetics, and reversed or inverted forms of amino acid sequences in which unsubstituted regions are reversed or inverted.

A non-limitative list of groups of amino acid residues that can be substituted for each other is shown below.
Group A: leucine, isoleucine, norleucine, valine, norvaline, alanine, 2-aminobutanoic acid, methionine, O-methylserine, t-butylglycine, t-butylalanine and cyclohexylalanine;
Group B: aspartic acid, glutamic acid, isoaspartic acid, isoglutamic acid, 2-aminoadipic acid and 2-aminosuberic acid;
Group C: asparagine and glutamine;
Group D: lysine, arginine, ornithine, 2,4-diaminobutanoic acid and 2,3-diaminopropionic acid;
Group E: proline, 3-hydroxyproline and 4-hydroxyproline;
Group F: serine, threonine and homoserine; and
Group G: phenylalanine and tyrosine.
Non-conservative substitution may include replacement of a member of one of the above groups by a member of another group, in which case the hydropathic indices of amino acids (amino acid hydropathic indices) should preferably be considered in order to retain biological functions of the proteins of the present invention (Kyte et al., J. Mol. Biol., 157:105-131 (1982)).

Non-conservative substitution may also include amino acid replacement based on hydrophilicity.

In the specification and drawings herein, nucleotide and amino acid notions and abbreviations are based on the IUPAC-IUB Commission on Biochemical Nomenclature or protocols conventionally used in the art as described, for example, in Immunology—A Synthesis (second edition, edited by E. S. Golub and D. R. Gren, Sinauer Associates, Sunderland, Mass. (1991)). Any optical isomers of amino acids that may exist refer to L-isomers, unless otherwise specified.

Stereoisomers of the above amino acids such as D-amino acids, unnatural amino acids such as α,α-disubstituted amino acids, N-alkylamino acids, lactic acid, and other non-canonical amino acids may also be components of the proteins of the present invention.

Proteins are herein written with the amino-terminus on the left and the carboxy-terminus on the right in accordance with standard usage and convention in the art. Similarly, single-stranded polynucleotide sequences are written with the 5'-end on the left end, and double-stranded polynucleotide sequences are written with the 5'-end of one strand on the left in general, unless otherwise specified.

One skilled in the art will be able to design and generate suitable variants of the proteins described herein using techniques known in the art. For example, one may identify suitable areas of the protein molecule that may be structurally changed without destroying biological activity of a protein of the present invention by targeting areas not believed to be important for the biological activity of the protein of the present invention. Also, one may identify residues and areas conserved between similar proteins. Furthermore, one will be able to introduce conservative amino acid substitutions into areas that may be important for the biological activity or structure of the protein of the present invention without destroying the biological activity and without adversely affecting the polypeptide structure of the protein.

One skilled in the art can perform so-called structure-function studies identifying residues in a peptide similar to a peptide of a protein of the present invention that are important for biological activity or structure of the protein of the present invention, and comparing the amino acid residues in the two peptides to predict which residues in a protein similar to the protein of the present invention are amino acid residues that correspond to amino acid residues that are important for biological activity or structure. Further, one may choose variants that retain the biological activity of the protein of the present invention by opting for chemically similar amino acid substitutions for such predicted amino acid residues. One skilled in the art can also analyze the three-dimensional structure and amino acid sequence of the variants of the protein. In view of the analytical results, one may further predict the alignment of amino acid residues with respect to the three-dimensional structure of the protein. Based on the analytical results as described above, one skilled in the art may also generate variants containing no changes to amino acid residues predicted to be on the surface of the protein, since such residues may be involved in important interactions with other molecules. Moreover, one skilled in the art may generate variants containing a single amino acid substitution among the amino acid residues constituting the protein of the present invention. The variants can be screened by known assays to gather information about the individual variants. As a result, one may evaluate usefulness of the individual amino acid residues constituting the protein of the present invention by comparing variants containing a change to a particular amino acid residue to assess whether they show reduced biological activity as compared with the biological activity of the protein of the present invention, or they show no such biological activity, or they show unsuitable activity inhibiting the biological activity of the protein of the present invention. Moreover, based on information gathered from such routine experiments, one skilled in the art can readily analyze undesirable amino acid substitutions for variants of the protein of the present invention either alone or in combination with other mutations.

As described above, proteins consisting of an amino acid sequence with deletion, substitution or addition of one or more amino acids in the amino acid sequence shown in SEQ ID NO: 2 or 7 can be prepared by such techniques as site-directed mutagenesis as described in "Molecular Cloning, A Laboratory Manual 3rd ed." (Cold Spring Harbor Press (2001)); "Current Protocols in Molecular Biology" (John Wiley & Sons (1987-1997); Kunkel (1985) Proc. Natl. Acad. Sci. USA 82: 488-92; Kunkel (1988) Method. Enzymol. 85: 2763-6, etc. Preparation of such variants containing amino acid deletions, substitutions or additions or the like can be carried out by known procedures such as e.g., the Kunkel method or the Gapped duplex method, using a mutation-introducing kit based on site-directed mutagenesis such as e.g., a QuikChange™ Site-Directed Mutagenesis Kit (Stratagene), a GeneTailor™ Site-Directed Mutagenesis System (Invitrogen) or a TaKaRa Site-Directed Mutagenesis System (Mutan-K, Mutan-Super Express Km, etc.; Takara Bio Inc.).

In addition to the site-directed mutagenesis mentioned above, techniques for introducing deletion, substitution or addition of one or more amino acids in the amino acid sequences of proteins while retaining their activity include treatment of a gene with a mutagen, and selective cleavage of a gene to remove, substitute or add a selected nucleotide followed by ligation.

A nucleic acid of the present invention preferably comprises a nucleotide sequence encoding a protein consisting of an amino acid sequence with deletion, substitution or addition of 1-50 amino acids in the amino acid sequence shown in SEQ ID NO: 2 or 7, and having the above activity of the present invention. There is no limitation on the number or sites of amino acid changes or modifications in the proteins of the present invention so far as the above activity of the present invention is retained. The method for assaying the above activity of the present invention is as described above.

(b) A nucleic acid that hybridizes under stringent conditions to a nucleic acid consisting of a nucleotide sequence complementary to the nucleotide sequence consisting of SEQ ID NO: 1 or 6 and that comprises a nucleotide sequence encoding a protein having the above activity of the present invention.

The nucleic acid of the present invention hybridizes under stringent conditions to a nucleic acid consisting of a nucleotide sequence complementary to the nucleotide sequence consisting of SEQ ID NO: 1 or 6 and comprises a nucleotide sequence encoding a protein having the above activity of the present invention. The "above activity of the present invention" is as described above.

The above nucleotide sequence can be obtained from a cDNA library and a genomic library or the like by a known hybridization technique such as colony hybridization, plaque hybridization or Southern blotting using a probe prepared from an appropriate fragment by a method known to those skilled in the art.

Detailed procedures for hybridization can be found in "Molecular Cloning, A Laboratory Manual 3rd ed." (Cold Spring Harbor Press (2001); especially Sections 6-7); "Current Protocols in Molecular Biology" (John Wiley & Sons (1987-1997); especially Sections 6.3-6.4); "DNA Cloning 1: Core Techniques, A Practical Approach 2nd ed." (Oxford University (1995); especially Section 2.10 for hybridization conditions), etc.

The strength of hybridization conditions is determined primarily by hybridization conditions, more preferably by hybridization conditions and washing conditions. As used herein, "stringent conditions" include moderately or highly stringent conditions.

Specifically, moderately stringent conditions include, for example, hybridization conditions of 1×SSC-6×SSC at 42° C.-55° C., more preferably 1×SSC-3×SSC at 45° C.-50° C., most preferably 2×SSC at 50° C. When the hybridization solution contains about 50% formamide, for example, temperatures 5-15° C. below the temperatures indicated above are used. Washing conditions include 0.5×SSC-6×SSC at 40° C.-60° C. During hybridization and washing, typically 0.05%-0.2%, preferably about 0.1% SDS may be added.

Highly stringent (high stringent) conditions include hybridization and/or washing at higher temperatures and/or lower salt concentrations than those of the moderately stringent conditions. For example, hybridization conditions include 0.1×SSC-2×SSC at 55° C.-65° C., more preferably 0.1×SSC-1×SSC at 60° C.-65° C., most preferably 0.2×SSC at 63° C. Washing conditions include 0.2×SSC-2×SSC at 50° C.-68° C., more preferably 0.2×SSC at 60-65° C.

Hybridization conditions specifically used in the present invention include for example, but are not limited to, prehybridization in 5×SSC, 1% SDS, 50 mM Tris-HCl (pH 7.5) and 50% formamide at 42° C. followed by hybridization with a probe at 42° C. overnight, and then washing three times in 0.2×SSC, 0.1% SDS at 65° C. for 20 minutes.

Commercially available hybridization kits using no radioactive probe can also be used. Specifically, hybridization may be performed using a DIG nucleic acid detection kit (Roche Diagnostics) or an ECL direct labeling & detection system (Amersham), etc.

A nucleic acid included in the present invention preferably hybridizes under conditions of 2×SSC, 50° C. to a nucleic acid consisting of a nucleotide sequence complementary to the nucleotide sequence consisting of SEQ ID NO: 1 or 6 and comprises a nucleotide sequence encoding a protein having the above activity of the present invention.

(c) A nucleic acid that comprises a nucleotide sequence sharing an identity of 80% or more with the nucleotide sequence consisting of SEQ ID NO: 1 or 6 and encoding a protein having the above activity of the present invention.

The nucleic acid of the present invention comprises a nucleotide sequence having at least 80% identity to the nucleotide sequence shown in SEQ ID NO: 1 or 6 and encoding a protein having the above activity of the present invention. The "above activity of the present invention" is as described above.

Preferably, the nucleic acid comprises a nucleotide sequence having at least 80%, more preferably 85%, still more preferably 90% (e.g., 92% or more, still more preferably 95% or more, even 97%, 98% or 99%) identity to the nucleotide sequence shown in SEQ ID NO: 1 or 6 and encoding a protein having the above activity of the present invention.

The percent identity between two nucleic acid sequences can be determined by visual inspection and mathematical calculation, or preferably by comparing sequence information of the two nucleic acids using a computer program. Computer programs for sequence comparison include, for example, the BLASTN program (Altschul et al. (1990) J. Mol. Biol. 215: 403-10) version 2.2.7 available from the website of the U.S. National Library of Medicine: www.ncbi.nlm.nih.gov/blast/bl2seq/bls.html, or the WU-BLAST 2.0 algorithm, etc. Standard default parameter settings for WU-BLAST 2.0 are available at the following Internet site: blast.wustl.edu.

(d) A nucleic acid that comprises a nucleotide sequence encoding a protein consisting of an amino acid sequence sharing an identity of 80% or more with the amino acid sequence consisting of SEQ ID NO: 2 or 7 and having the above activity of the present invention.

The nucleic acid of the present invention comprises a nucleotide sequence encoding a protein consisting of an amino acid sequence sharing an identity of 80% or more with the amino acid sequence consisting of SEQ ID NO: 2 or 7 and having the above activity of the present invention. The "above activity of the present invention" is as described above.

Specifically, the amino acid sequence has 80% or more, preferably 85% or more, more preferably 90%, still more preferably 95% or more, even more preferably 97% (e.g., 98%, even 99%) or more identity to the amino acid sequence of SEQ ID NO: 2 or 7 or the like.

The nucleic acid of the present invention preferably comprises a nucleotide sequence encoding a protein consisting of an amino acid sequence sharing an identity of 95% or more with the amino acid sequence consisting of SEQ ID NO: 2 or 7 and having the above activity of the present invention. More preferably, the nucleic acid comprises a nucleotide sequence encoding a protein consisting of an amino acid sequence sharing an identity of 98% or more with the amino acid sequence consisting of SEQ ID NO: 2 or 7 and having the above activity of the present invention.

The percent identity between two amino acid sequences can be determined by visual inspection and mathematical calculation. Alternatively, the percent identity can be determined by using a computer program. Such computer programs include, for example, BLAST, FASTA (Altschul et al., J. Mol. Biol., 215:403-410 (1990)) and ClustalW, etc. In particular, various conditions (parameters) for an identity search with the BLAST program are described by Altschul et al. (Nucl. Acids. Res., 25, p. 3389-3402, 1997) and publicly available from the website of the National Center for Biotechnology Information (NCBI) or the DNA Data Bank of Japan (DDBJ) (BLAST Manual, Altschul et al., NCB/NLM/NIH Bethesda, Md. 20894; Altschul et al.). The percent identity can also be determined using genetic information processing programs such as GENETYX Ver.7 (Genetyx), DNASIS Pro (Hitachisoft), Vector NTI (Infomax), etc.

Certain alignment schemes for aligning amino acid sequences may result in the matching of even a specific short region of the sequences, and thereby it is possible to detect a region with very high sequence identity in such a small aligned region, even when there is no significant relationship between the full-length sequences used. In addition, the BLAST algorithm may use the BLOSUM62 amino acid scoring matrix and optional parameters as follows: (A) inclusion of a filter to mask off segments of the query sequence that have low compositional complexity (as determined by the SEG program of Wootton and Federhen (Computers and Chemistry, 1993); also see Wootton and Federhen, 1996, "Analysis of compositionally biased regions in sequence databases," Methods Enzymol., 266: 554-71) or segments consisting of short-periodicity internal repeats (as determined by the XNU program of Claverie and States (Computers and Chemistry, 1993)), and (B) a statistical significance threshold for reporting matches against database sequences, or E-score (the expected probability of matches being found merely by chance according to the stochastic model of Karlin and Altschul, 1990; if the statistical significance ascribed to a match is greater than this E-score threshold, the match will not be reported).

(e) A nucleic acid that hybridizes under stringent conditions to a nucleic acid consisting of a nucleotide sequence complementary to a nucleotide sequence encoding a protein consisting of the amino acid sequence shown in SEQ ID NO: 2 or 7 and that comprises a nucleotide sequence encoding a protein having the above activity of the present invention.

The nucleic acid of the present invention hybridizes under stringent conditions to a nucleic acid consisting of a nucleotide sequence complementary to a nucleotide sequence encoding a protein consisting of the amino acid sequence shown in SEQ ID NO: 2 or 7 and comprises a nucleotide sequence encoding a protein having the above activity of the present invention.

The "above activity of the present invention" and hybridization conditions are as described above.

Further, the nucleic acids of the present invention also include a nucleic acid that comprises a nucleotide sequence with deletion, substitution or addition of one or more nucleotides in the nucleotide sequence consisting of SEQ ID NO: 1 or 6, and encoding a protein having the above activity of the present invention. Specifically, it is also possible to use a nucleic acid which comprises a nucleotide sequence with deletion, substitution or addition of one or more (preferably one or several (e.g., 1-1500, 1-1000, 1-500, 1-300, 1-250, 1-200, 1-150, 1-100, 1-50, 1-30, 1-25, 1-20, 1-15, more preferably 10, 9, 8, 7, 6, 5, 4, 3, 2, or 1)) nucleotides in the nucleotide sequence shown in SEQ ID NO:1 or 6, and encoding a protein having the above activity of the present invention. As used here, the expression "nucleotide sequence with deletion, substitution or addition" means that one or more nucleotides are deleted, substituted and/or added at one or more random positions in the same nucleotide sequence. Two or more of the deletion, substitution and/or addition may occur at the same time, but the number of the deletion, substitution and/or addition is preferably smaller, in general.

Preferred embodiments of the nucleic acids of the present invention also include a nucleic acid of any one of (a)-(d) below:
(a) a nucleic acid that comprises the nucleotide sequence shown in SEQ ID NO: 1 or 6 or a partial sequence thereof;
(b) a nucleic acid that comprises a nucleotide sequence encoding the amino acid sequence shown in SEQ ID NO: 2 or 7 or a partial sequence thereof;
(c) a nucleic acid that comprises the nucleotide sequence shown in SEQ ID NO: 4 or 9 or a partial sequence thereof;
(d) a nucleic acid that comprises the nucleotide sequence shown in SEQ ID NO: 5 or 10 or a partial sequence thereof.

The nucleic acids defined as (a) a nucleic acid that comprises the nucleotide sequence shown in SEQ ID NO: 1 or 6; (b) a nucleic acid that comprises a nucleotide sequence encoding a protein consisting of the amino acid sequence shown in SEQ ID NO: 2 or 7; and (c) a nucleic acid that comprises the nucleotide sequence shown in SEQ ID NO: 4 or 9 are as described above. The partial sequence of the above sequences are regions contained in the above nucleotide sequences including ORFs, CDSs, biologically active regions, regions used as primers as described below, and regions capable of serving as probes, and may be naturally occurring or artificially prepared.

The nucleic acids of the present invention are preferably nucleic acids encoding a protein belonging to the membrane-bound O-acyltransferase family. The "membrane-bound O-acyltransferase family" is as described above.

The nucleic acids of the present invention also include:
(1) a nucleic acid of any one of (a)-(e) below:
(a) a nucleic acid that comprises a nucleotide sequence encoding a protein consisting of an amino acid sequence with deletion, substitution or addition of one or more amino acids in the amino acid sequence shown in SEQ ID NO: 2 or 7;
(b) a nucleic acid that hybridizes under stringent conditions to a nucleic acid consisting of a nucleotide sequence complementary to the nucleotide sequence consisting of SEQ ID NO: 1 or 6;
(c) a nucleic acid that comprises a nucleotide sequence sharing an identity of 80% or more with the nucleotide sequence consisting of SEQ ID NO: 1 or 6;
(d) a nucleic acid that comprises a nucleotide sequence encoding a protein consisting of an amino acid sequence sharing an identity of 80% or more with the amino acid sequence consisting of SEQ ID NO: 2 or 7;
(e) a nucleic acid that hybridizes under stringent conditions to a nucleic acid consisting of a nucleotide sequence complementary to a nucleotide sequence encoding a protein consisting of the amino acid sequence shown in SEQ ID NO: 2 or 7; and
(2) the nucleic acid of (1), which is any one of (a)-(e) below:
(a) a nucleic acid that comprises a nucleotide sequence encoding a protein consisting of an amino acid sequence with deletion, substitution or addition of 1-50 amino acids in the amino acid sequence shown in SEQ ID NO: 2 or 7;
(b) a nucleic acid that hybridizes under conditions of 2×SSC, 50° C. to a nucleic acid consisting of a nucleotide sequence complementary to the nucleotide sequence consisting of SEQ ID NO: 1 or 6;
(c) a nucleic acid that comprises a nucleotide sequence sharing an identity of 90% or more with the nucleotide sequence consisting of SEQ ID NO: 1 or 6;
(d) a nucleic acid that comprises a nucleotide sequence encoding a protein consisting of an amino acid sequence sharing an identity of 90% or more with the amino acid sequence consisting of SEQ ID NO: 2 or 7;
(e) a nucleic acid that hybridizes under conditions of 2×SSC, 50° C. to a nucleic acid consisting of a nucleotide sequence complementary to a nucleotide sequence encoding a protein consisting of the amino acid sequence shown in SEQ ID NO: 2 or 7.

Lysophospholipid Acyltransferase Proteins of the Present Invention

The proteins of the present invention are characterized in that they have "lysophospholipid acyltransferase activity (LPLAT activity)", "the activity of increasing the proportion of arachidonic acid", and/or "the activity involved in the biosynthetic pathway of arachidonic acid". The proteins of the present invention may be naturally occurring or artificially prepared.

The proteins of the present invention are preferably LPLAT5 and LPLAT6 consisting of the amino acid sequence shown in SEQ ID NO: 2 or 7. Further, the present invention also encompasses variants of LPLAT5 and LPLAT6, i.e. variants satisfying the criteria: having "lysophospholipid acyltransferase activity (LPLAT activity)", "the activity of increasing the proportion of arachidonic acid", and/or "the activity involved in the biosynthetic pathway of arachidonic acid".

The "lysophospholipid acyltransferase activity", "the activity of increasing the proportion of arachidonic acid" and "the activity involved in the biosynthetic pathway of arachidonic acid" are as described above in the section "Nucleic acids encoding lysophospholipid acyltransferases of the present invention". As used herein below, the "above activity of the present invention" refers to the "LPLAT activity, the activity of increasing the proportion of arachidonic acid, and/or the activity involved in the biosynthetic pathway of arachidonic acid" defined above.

The proteins of the present invention include a protein of (a) or (b) below:
(a) a protein consisting of an amino acid sequence with deletion, substitution or addition of one or more amino acids in the amino acid sequence of SEQ ID NO: 2 or 7, and having the above activity of the present invention;
(b) a protein consisting of an amino acid sequence sharing an identity of 80% or more with the amino acid sequence consisting of SEQ ID NO: 2 or 7 and having the above activity of the present invention.

The definitions of "an amino acid sequence with deletion, substitution or addition of one or more amino acids in an amino acid sequence" and "identity of 80% or more" are as explained above in the section "Nucleic acids encoding lysophospholipid acyltransferases of the present invention".

The proteins of the present invention also include a variant of a protein encoded by a nucleic acid comprising the nucleotide sequence of SEQ ID NO: 1 or 6, or a protein of an amino acid sequence with deletion, substitution or addition of one or more amino acids in the amino acid sequence shown in SEQ ID NO: 2 or 7 or otherwise modified, or a modified protein having a modified amino acid side chain, or a fusion protein with another protein and having the above activity of the present invention.

The proteins of the present invention may be artificially prepared by chemical synthesis techniques such as Fmoc method (fluorenylmethyloxycarbonyl method) and tBoc method (t-butyloxycarbonyl method). They can also be chemically synthesized using a peptide synthesizer available from Advanced ChemTech, Perkin Elmer, Pharmacia, Protein Technology Instrument, Synthecell-Vega, PerSeptive, Shimadzu Corporation or the like.

Moreover, the proteins of the present invention are preferably proteins belonging to the membrane-bound O-acyltransferase family. The definition or the like of the "membrane-bound O-acyltransferase family" is as explained above in the section "Nucleic acids encoding lysophospholipid acyltransferases of the present invention".

The proteins of the present invention also include:
(1) a protein of (a) or (b) below:
(a) a protein consisting of an amino acid sequence with deletion, substitution or addition of one or more amino acids in the amino acid sequence of SEQ ID NO: 2 or 7;
(b) a protein consisting of an amino acid sequence sharing an identity of 80% or more with the amino acid sequence consisting of SEQ ID NO: 2 or 7;
(2) the protein of (1), which is (a) or (b) below:
(a) a protein consisting of an amino acid sequence with deletion, substitution or addition of 1-50 amino acids in the amino acid sequence of SEQ ID NO: 2 or 7;
(b) a protein consisting of an amino acid sequence sharing an identity of 90% or more with the amino acid sequence consisting of SEQ ID NO: 2 or 7.

Cloning of the Nucleic Acids of the Present Invention

The nucleic acids encoding the LPLAT proteins of the present invention can be cloned by, for example, screening from a cDNA library using an appropriate probe. They can also be cloned by PCR amplification with appropriate primers followed by ligation to an appropriate vector. The resulting clone may further be subcloned into another vector.

For example, commercially available plasmid vectors can be used, such as pBlue-Script™ SK (+) (Stratagene), pGEM-T (Promega), pAmp (TM: Gibco-BRL), p-Direct (Clontech) and pCR2.1-TOPO (Invitrogen). For amplification by PCR, any regions of the nucleotide sequences shown in SEQ ID NO: 1 or 6 and the like may be used as primers, including the primers shown in Example 1 below, for example. PCR is performed by adding the above primers and a heat-resistant DNA polymerase or the like to act on cDNA prepared from *M. alpina* cells. The above procedure can be readily accomplished by those skilled in the art according to "Molecular Cloning, A Laboratory Manual 3rd ed." (Cold Spring Harbor Press (2001)) or the like.

The resulting PCR product can be purified using known methods. For example, purification methods include those using kits such as GENECLEAN (Funakoshi Co., Ltd.), QIAquick PCR purification Kits (QIAGEN), ExoSAP-IT (GE Healthcare Bio-Sciences); or using DEAE-cellulose filters or dialysis tubes, etc. When an agarose gel is used, DNA fragments are subjected to agarose gel electrophoresis and the DNA fragments re excised from the agarose gel, followed by purification with GENECLEAN (Funakoshi Co., Ltd.), QIAquick Gel extraction Kits (QIAGEN), a freeze-squeeze method, etc.

The nucleotide sequences of the cloned nucleic acids can be determined using a nucleotide sequencer.

Construction of Expression Vectors of the Present Invention and Preparation of Transformed Cells The present invention also provides recombinant vectors containing a nucleic acid encoding an LPLAT protein of the present invention. The present invention further provides cells transformed with the recombinant vectors.

Such recombinant vectors and transformants can be obtained as follows. That is, a plasmid carrying a nucleic acid encoding an LPLAT protein of the present invention is digested with restriction endonucleases. The restriction endonucleases used include for example, but not limited to, EcoRI, KpnI, BamHI and SalI, etc. The plasmid may be blunt-ended by T4 polymerase treatment. The digested DNA fragment is purified by agarose gel electrophoresis. This DNA fragment may be inserted into an expression vector by a known method, thereby giving a vector for expressing the LPLAT protein. This expression vector is transformed into a host to prepare a transformant, which is used for the expression of a desired protein.

The expression vector and host here are not specifically limited so far as a desired protein can be expressed, and suitable hosts include fungi, bacteria, plants and animals or cells thereof, for example. Fungi include filamentous fungi such as the lipid-producing fungus *M. alpina*, yeast such as *S. cerevisiae* (*Saccharomyces cerevisiae*), etc. Bacteria include *Escherichia coli, Bacillus subtilis*, etc. Further, plants include oil-producing plants such as rapeseed, soybean, cottonseed, safflower and flax.

Lipid-producing fungi that can be used include, for example, the strains described in MYCOTAXON, Vol. XLIV, NO. 2, pp. 257-265 (1992), specifically microorganisms belonging to the genus *Mortierella*, including microorganisms belonging to the subgenus *Mortierella* such as *Mortierella elongata* (*M. elongata*) WO8570, *Mortierella exigua* (*M.*

*exigua*) IFO8571, *Mortierella hygrophila* (*M. hygrophila*) IFO5941, *Mortierella alpina* IFO8568, ATCC16266, ATCC32221, ATCC42430, CBS219.35, CBS224.37, CBS250.53, CBS343.66, CBS527.72, CBS528.72, CBS529.72, CBS608.70, CBS754.68, or microorganisms belonging to the subgenus *Micromucor* such as *Mortierella isabellina* (*M. isabellina*) CBS194.28, IFO6336, IFO7824, IFO7873, IFO7874, IFO8286, IFO8308, IFO7884, *Mortierella nana* (*M. nana*) IFO8190, *Mortierella ramanniana* (*M. ramanniana*) IFO5426, IFO8186, CBS112.08, CBS212.72, IFO7825, IFO8184, IFO8185, IFO8287, *Mortierella vinacea* (*M. vinacea*) CBS236.82. Among others, *M. alpina* is preferred.

When a fungus is used as a host, the vector preferably has a structure that allows a nucleic acid of the present invention to self-replicate in the host or to be inserted onto a chromosome of the fungus. Also, it preferably contains a promoter and a terminator. When *M. alpina* is used as a host, the expression vector may be, for example, pD4, pDuraSC, pDura5 or the like. Any promoter that can be expressed in the host may be used, including *M. alpina*-derived promoters such as the promoter of the histone H4.1 gene, the promoter of the GAPDH (glyceraldehyde-3-phosphate dehydrogenase) gene and the promoter of the TEF (translation elongation factor) gene.

Techniques for transforming a recombinant vector into filamentous fungi such as *M. alpina* include electroporation, the spheroplast method, particle delivery, and direct microinjection of DNA into nuclei, etc. When an auxotrophic host strain is used, transformed strains can be obtained by selecting strains growing on a selective medium lacking its essential nutrients. When a drug resistance marker gene is used for transformation, cell colonies showing drug resistance can be obtained by culturing in a selective medium containing the drug.

When yeast is used as a host, the expression vector may be, for example, pYE22m or the like. Commercially available yeast expression vectors such as pYES (Invitrogen) and pESC (STRATAGENE) may also be used. Yeast hosts suitable for the present invention include, but are not limited to, *S. cerevisiae* strain EH13-15 (trp1, MATα), etc. Promoters used include, for example, those derived from yeast or the like, such as GAPDH promoter, GAL1 promoter and GAL10 promoter.

Techniques for transforming a recombinant vector into yeast include, for example, the lithium acetate method, electroporation, the spheroplast method, dextran-mediated transfection, calcium phosphate precipitation, polybrene-mediated transfection, protoplast fusion, encapsulation of (one or more) polynucleotide (s) in liposomes, and direct microinjection of DNA into nuclei, etc.

When a bacterium such as *E. coli* is used as a host, the expression vector may be, for example, pGEX, pUC18 or the like available from Pharmacia. Promoters that can be used include those derived from *E. coli*, phages and the like, such as trp promoter, lac promoter, PL promoter and PR promoter, for example. Techniques for transforming a recombinant vector into bacteria include, for example, electroporation and the calcium chloride method.

Methods for Preparing Fatty Acid Compositions of the Present Invention

The present invention provides methods for preparing a fatty acid composition from the transformed cell described above, i.e., methods for preparing a fatty acid composition from cultures of the transformed cell. Specifically, it can be prepared by the procedure described below. However, the present methods are not limited to the procedures below, but can also be carried out by using other conventional known procedures.

Any liquid medium (culture medium) may be used for culturing an organism expressing a protein of the present invention so far as it has appropriate pH and osmotic pressure and contains nutrients required for growth of each host, trace elements, and biological materials such as sera or antibiotics. For example, culture media that can be used for yeast cells transformed to express LPLAT 5 and 6 include, but not limited to, SC-Trp, Leu, Ura medium, YPD medium, YPD5 medium and the like.

Any culture conditions suitable for host growth and for stably maintaining the generated enzyme may be used, and specifically, individual conditions can be adjusted, including anaerobicity, incubation period, temperature, humidity, static or shaking culture, etc. Cultivation may be performed under the same conditions (one-step culture) or may be so-called two-step or three-step culture using two or more different culture conditions, but two-step culture and the like are preferred for large-scale culture, because of high culture efficiency.

Fatty Acid Compositions of the Present Invention

The present invention also provides fatty acid compositions comprising an assembly of one or more fatty acids in a cell expressing an LPLAT protein of the present invention, characterized in that the proportion of arachidonic acid in compositional ratio of fatty acids in the fatty acid composition is higher than the proportion of arachidonic acid in fatty acid compositions obtained by culturing non-transformed hosts. Preferably, it provides fatty acid compositions obtained by culturing a transformed cell expressing LPLAT5 and 6 of the present invention. In the Examples below, the proportion of arachidonic acid in an-arachidonic acid-producing yeast transformed with LPLAT5 or 6 increased at least 1.5-fold as compared with the proportion of arachidonic acid in the control fatty acid composition.

The fatty acids may be free fatty acids or those composing triglycerides, phospholipids or the like.

The fatty acids contained in the fatty acid compositions of the present invention are linear or branched monocarboxylic acids with long-chain carbohydrates, including for example, but not limited to, myristic acid (tetradecanoic acid) (14:0), myristoleic acid (tetradecenoic acid) (14:1), palmitic acid (hexadecanoic acid) (16:0), palmitoleic acid (9-hexadecenoic acid) (16:1), stearic acid (octadecanoic acid) (18:0), oleic acid (cis-9-octadecenoic acid) (18:1 (9) or sometimes simply referred to as 18:1), vaccenic acid (11-octadecenoic acid) (18:1 (11)), linoleic acid (cis,cis-9,12 octadecadienoic acid) (18:2 (9,12) or sometimes simply referred to as 18:2), α-linolenic acid (9,12,15-octadecatrienoic acid) (18:3 (9,12,15)), γ-linolenic acid (6,9,12-octadecatrienoic acid) (18:3 (6,9,12), GLA or sometimes referred to as 18:3(n-6)), stearidonic acid (6,9,12,15-octadecatetraenoic acid) (18:4 (6,9,12,15)), arachidic acid (icosanoic acid) (20:0), (8,11-icosadienoic acid) (20:2 (8,11)), mead acid (5,8,11-icosatrienoic acid) (20:3 (5,8,11)), dihomo-γ-linolenic acid (8,11,14-icosatrienoic acid) (20:3 (8,11,14) or sometimes referred to as DGLA), arachidonic acid (5,8,11,14-icosatetraenoic acid) (20:4 (5,8,11,14) or sometimes referred to as ALA), eicosatetraenoic acid (8,11,14,17-icosatetraenoic acid) (20:4 (8,11,14,17)), eicosapentaenoic acid (5,8,11,14,17-icosapentaenoic acid) (20:5 (5,8,11,14,17)), behenic acid (docosanoic acid) (22:0), (7,10,13,16-docosatetraenoic acid) (22:4 (7,10, 13,16)), (7,10,13,16,19-docosapentaenoic acid) (22:5 (7,10, 13,16,19)), (4,7,10,13,16-docosapentaenoic acid) (22:5 (4,7, 10,13,16)), (4,7,10,13,16,19-docosahexaenoic acid) (22:6

(4,7,10,13,16,19)), lignoceric acid (tetradocosanoic acid) (24:0), nervonic acid (cis-15-tetracosenoic acid) (24:1), cerotic acid (hexadocosanoic acid) (26:0), etc. The chemical names shown above are common names defined by the IUPAC Biochemical Nomenclature, and each followed by the systematic name and then the number of carbon atoms and the number and positions of double bonds in parentheses.

The fatty acid composition of the present inventions may be composed of any number and any type of fatty acids so far as they comprise a combination of one or more of the fatty acids listed above.

Lyophilized cells obtained by the methods for preparing fatty acid compositions of the present invention described above are stirred with a chloroform/methanol mixture prepared in a suitable ratio, and then heated for a suitable period. Further, separation of the cells by centrifugation and solvent recovery are repeated several times. Then, lipids are dried by a suitable method and then dissolved in a solvent such as chloroform. An aliquot of this sample is collected and fatty acids in the cells are converted into methyl esters using methanolic HCl, then extracted with hexane, and hexane is distilled off and the residue is analyzed by gas chromatography.

The proportion of arachidonic acid in the compositional ratio of fatty acids of the fatty acid composition obtained by culturing a cell transformed with a recombinant vector containing a nucleic acid of the present invention is higher than the proportion of arachidonic acid in known LPLAT fatty acid compositions. This is attributed to the fact that the LPLATs of the present invention can increase the conversion of fatty acids requiring acyl transfer from acyl-CoA to phospholipids or from phospholipids to CoA. Specifically, the proportion of arachidonic acid in fatty acid compositions produced by arachidonic acid-producing yeast (*S. cerevisiae*) expressing LPLAT5 and LPLAT6 according to preferred embodiments of the present invention increases, as further described in the Examples below. In this case, LPLAT5 was found to be involved in the conversion from 18:1-CoA to 18:1-PL, conversion from 18:3(n-6)-PL to 18:3(n-6)-CoA and conversion from DGLA-CoA to DGLA-PL, and LPLAT6 was found to be involved in the conversion from 18:3(n-6)-PL to 18:3(n-6)-CoA and conversion from DGLA-CoA to DGLA-PL.

As described in the Examples below, LPLAT6 was also found to be involved in the conversion from 18:3(n-6)-PL to 18:3(n-6)-CoA and conversion from DGLA-CoA to DGLA-PL in *M. alpina*.

Therefore, the present invention also provides a method for using a recombinant vector to increase the proportion of arachidonic acid in the compositional ratio of fatty acids in a host transformed with the vector as compared with the proportion in the compositional ratio of fatty acids in a host that has not been transformed with the vector.

Food or Other Products Comprising Fatty Acid Compositions of the Present Invention The present invention also provides food products comprising the above fatty acid compositions. The fatty acid compositions of the present invention can be routinely used to produce food products and industrial raw materials containing fats and oils (raw materials for cosmetics, pharmaceuticals (e.g., topical skin medicines), soaps, etc.) or for other purposes. Cosmetics (compositions) or pharmaceuticals (compositions) may be presented in any form including, but not limited to, solution, paste, gel, solid, powder or the like. Food products may also be presented in the form of a pharmaceutical formulation such as a capsule, or a processed food such as a natural liquid diet, low residue diet, elemental diet, nutritional drink or enteral feeding formula comprising a fatty acid composition of the present invention in combination with proteins, sugars, fats, trace elements, vitamins, emulsifiers, flavorings, etc.

Other examples of food products of the present invention include, but are not limited to, dietary supplements, health foods, functional foods, diets for children, modified milk for infants, modified milk for premature infants, geriatric diets, etc. The food products as used herein collectively refer to edible products in the form of solid, fluid, liquid or a mixture thereof.

Dietary supplements refer to food products fortified with specific nutritional ingredients. Health foods refer to food products known to be healthy or good for health, and include dietary supplements, natural foods, dietetic foods, etc. Functional foods refer to food products for supplying nutritional ingredients having physiological control functions, and may also be called foods for specified health use. Diets for children refer to food products intended for children up to about 6 years of age. Geriatric diets refer to food products treated to ease digestion and absorption as compared with untreated foods. Modified milk for infants refers to modified milk intended for children up to about one year of age. Modified milk for premature infants refers to modified milk intended for premature infants of up to about 6 months of age.

These food products include natural foods such as meat, fish, nuts (treated with fats and oils); foods cooked with fats and oils such as Chinese foods, Chinese noodles, soups; foods using fats and oils as heating media such as Tempura (deep-fried fish and vegetables), deep-fried foods coated in breadcrumbs, fried bean curd, Chinese fried rice, doughnuts, Karinto (Japanese fried dough cookies); fat- and oil-based food products or food products processed with fats and oils such as butter, margarine, mayonnaise, salad dressing, chocolate, instant noodles, caramel, biscuits, cookies, cake, ice cream; and food products sprayed or coated with fats and oils during finishing such as rice crackers, hard biscuits, sweet bean paste bread. However, the food products of the present invention are not limited to fat- and oil-containing foods, but also include processed agricultural foods such as bread, noodles, cooked rice, sweets (candies, chewing gums, gummies, tablets, Japanese sweets), bean curd and processed products thereof; fermented foods such as Sake (Japanese rice wine), medicinal liquor, Mirin (sweet cooking sherry), vinegar, soy sauce and Miso (soy bean paste); livestock food products such as yogurt, ham, bacon and sausage; processed seafood products such as Kamaboko (fish cake), Ageten (deep-fried fish cake) and Hanpen (puffy fish cake); and fruit drinks, soft drinks, sports drinks, alcoholic beverages, tea and the like.

Method for Evaluating or Selecting Strains Using Nucleic Acids Encoding LPLAT Proteins or LPLAT Proteins of the Present Invention The present invention also provides methods for evaluating or selecting lipid-producing strains using nucleic acids encoding LPLAT proteins or LPLAT proteins of the present invention. The methods are specifically described below.

(1) Evaluation Methods

One embodiment of the present invention is a method for evaluating a lipid-producing strain using a nucleic acid encoding an LPLAT protein or an LPLAT protein of the present invention. The evaluation method of the present invention may comprise evaluating a lipid-producing test strain for the above activity of the present invention using a primer or probe designed on the basis of a nucleotide sequence of the present invention. General procedures for such an evaluation method are known and described in, e.g., WO01/040514 or JP HEI 8-205900A. This evaluation method is briefly explained below.

First, the genome of a test strain is prepared. Any known preparation method can be used such as the Hereford method or potassium acetate method (see, e.g., Methods in Yeast Genetics, Cold Spring Harbor Laboratory Press, p 130 (1990)).

A primer or probe is designed on the basis of a nucleotide sequence of the present invention, preferably SEQ ID NO: 1 or 6. The primer or probe can be designed from any region of the nucleotide sequence of the present invention using known procedures. The number of nucleotides in a polynucleotide used as a primer is typically 10 or more, preferably 15 to 25. Typically, the number of nucleotides appropriate for a region to be flanked by the primers is generally 300 to 2000.

The primer or probe prepared above is used to assess whether or not the genome of the above test strain contains a sequence specific to the nucleotide sequence of the present invention. A sequence specific to the nucleotide sequence of the present invention may be detected using known procedures. For example, a polynucleotide comprising a part or all of a sequence specific to the nucleotide sequence of the present invention or a polynucleotide comprising a nucleotide sequence complementary to the above nucleotide sequence is used as one primer, and a polynucleotide comprising a part or all of a sequence upstream or downstream of this sequence or a polynucleotide comprising a nucleotide sequence complementary to the above nucleotide sequence is used as the other primer to amplify the nucleic acid of the test strain by PCR or the like, thereby determining the presence or absence of an amplified product, the molecular weight of the amplified product, etc.

PCR conditions suitable for the method of the present invention are not specifically limited. The resulting reaction product, i.e., the amplified product can be separated by electrophoresis on agarose gel or the like to determine the molecular weight of the amplified product. Thus, the above activity of the present invention of the test strain can be predicted or evaluated by assessing whether or not the molecular weight of the amplified product is enough to cover a nucleic acid molecule corresponding to a region specific to the nucleotide sequence of the present invention. Moreover, the above activity of the present invention can be more accurately predicted or evaluated by analyzing the nucleotide sequence of the amplified product by the method described above or the like. The method for evaluating the above activity of the present invention is as described above.

Alternatively, the evaluation method of the present invention may comprise culturing a test strain and determining the expression level of an LPLAT protein encoded by a nucleotide sequence of the present invention such as SEQ ID NO: 1 or 6, thereby evaluating the test strain for the above activity of the present invention. The expression level of the LPLAT protein can be determined by culturing the test strain under appropriate conditions and quantifying mRNA of the LPLAT protein or the protein. Quantification of mRNA or the protein may be accomplished by using known procedures. Quantification of mRNA may be accomplished by, for example, Northern hybridization or quantitative RT-PCR, while quantification of the protein may be accomplished by, for example, Western blotting (Current Protocols in Molecular Biology, John Wiley & Sons 1994-2003).

(2) Selection Methods

Another embodiment of the present invention is a method for selecting a lipid-producing strain using a nucleic acid encoding an LPLAT protein or an LPLAT protein of the present invention. The selection method of the present invention may comprise culturing test strains and determining the expression level of an LPLAT protein encoded by a nucleotide sequence of the present invention such as SEQ ID NO: 1 or 6 to select a strain having a desired expression level, whereby a strain having a desired activity can be selected. Alternatively, it may comprise predetermining a type strain, separately culturing the type strain and test strains, determining the above expression level in each strain, and comparing the expression level between the type strain and each test strain, whereby a desired strain can be selected. Specifically, a strain having a desired activity can be selected by culturing a type strain and test strains under appropriate conditions, determining the expression level in each strain, and selecting a test strain showing a higher or lower expression level than that of the type strain, for example. The desired activity may be assessed by determining the expression level of the LPLAT protein, as described above.

Alternatively, the selection method of the present invention may comprise culturing test strains and selecting a strain showing a higher or lower level of the above activity of the present invention, whereby a strain having a desired activity can be selected. The desired activity may be assessed by determining the expression level of the LPLAT protein, as described above.

Examples of test strains or type strains that can be used include for example, but are not limited to, a strain transformed with the above vector of the present invention, a strain with suppressed expression of the above nucleic acid of the present invention, a mutagenized strain, a naturally mutated strain, etc. Mutagenesis techniques include, but not limited to, physical methods such as UV or radioactive irradiation, and chemical methods such as chemical treatments with EMS (ethyl methanesulfonate), N-methyl-N-nitrosoguanidine or the like (see, e.g., Yasuji Oshima ed., Biochemistry Experiments vol. 39, Experimental Protocols for Yeast Molecular Genetics, pp. 67-75, Japan Scientific Societies Press).

Strains used as type and test strains of the present invention include, but are not limited to, the lipid-producing fungi or yeast listed above. Specifically, the type and test strains may be a combination of any strains belonging to different genera or species, and one or more test strains may be used simultaneously.

The following examples further illustrate the present invention. However, it should be understood that the present invention is not limited to the Examples below.

EXAMPLES

Example 1

Genomic Analysis of *M. Alpina*

*M. alpina* strain 1S-4 was inoculated into 100 ml of GY2:1 medium (2% glucose, 1% yeast extract, pH 6.0) and cultured with shaking for 2 days at 28° C. The cells were harvested by filtration to prepare genomic DNA using DNeasy (QIAGEN).

The nucleotide sequence of the genomic DNA was determined using Roche454GS FLX Standard. This involved two runs of fragment library sequence sequencing and three runs of mate pair library sequencing. The resulting nucleotide sequences were assembled into 300 supercontigs.

Construction of cDNA Libraries

*M. alpina* strain 1S-4 was inoculated into 100 ml of a medium (1.8% glucose, 1% yeast extract, pH 6.0) and pre-cultured for 3 days at 28° C. The total amount of the preculture was inoculated into 5 L of a medium (1.8% glucose, 1% soybean powder, 0.1% olive oil, 0.01% Adekanol, 0.3%

KH$_2$PO$_4$, 0.1% Na$_2$SO$_4$, 0.05% CaCl$_2$.2H$_2$O, 0.05% MgCl$_2$.6H$_2$O, pH 6.0) in a 10 L culture vessel (Able Co., Tokyo) and incubated with aeration and agitation under conditions of 300 rpm, 1 vvm, 26° C. for 8 days. On incubation days 1, 2 and 3, glucose was added in amounts equivalent to 2%, 2% and 1.5%, respectively. At each stage of incubation days 1, 2, 3, 6 and 8, cells were harvested to prepare total RNA by the guanidine hydrochloride/CsCl method. Using an Oligotex-dT30<Super> mRNA Purification Kit ("dT30" disclosed as SEQ ID NO: 45) (Takara Bio Inc.), poly(A)$^+$RNA was purified from the total RNA. A cDNA library at each stage was constructed using a ZAP-cDNA GigapackIII Gold Cloning Kit (STRATAGENE).

Search for Homologs of SCL4 from *S. cerevisiae*

Supercontigs containing the sequences shown in SEQ ID NO: 5 and SEQ ID NO: 10 were identified by tblastn analysis of the amino acid sequence deduced from SLC4 (YOR175c) encoding an LPLAT of the MBOAT family of *S. cerevisiae* (PfamPFO3062) against the genomic nucleotide sequence of *M. alpina* 1S-4.

Preparation of a Probe

To clone cDNAs corresponding to SEQ ID NO: 5 and SEQ ID NO: 10, the following primers were prepared (Table 2).

TABLE 2

| Primers | |
|---|---|
| MaLPAAT5-1F (SEQ ID NO: 11) | CTGTCTCCTTCCCAGAGGATCAGC |
| MaLPAAT5-3R (SEQ ID NO: 12) | ATAACCAAAGCGCAAGATCCATGG |
| MaLPAAT6-2F (SEQ ID NO: 13) | GTTGCCCACGTTGGCCGAGACGATC |
| MaLPAAT6-3R (SEQ ID NO: 14) | ATGGGTTCCGTGCCAGATCGCCAAG |

The cDNA libraries were used as templates to perform PCR with ExTaq (Takara Bio Inc.) and the above primers in the following sets: MaLPAAT5-1F/MaLPAAT5-3R and MaLPAAT6-2F/MaLPAAT5-3R. The resulting DNA fragments were cloned using a TOPO-TA cloning kit (INVITROGEN) to give a plasmid containing nucleotides 195-931 of SEQ ID NO: 4 designated pCR-LPLAT5-P and a plasmid containing nucleotides 766-1414 of SEQ ID NO: 9 designated pCR-LPLAT6-P. Then, these plasmids were used as templates to perform PCR with the above primers. ExTaq (Takara Bio Inc.) was used for the reaction, but a PCR labeling mix (Roche Diagnostics) was used instead of the dNTP mix included in the kit to prepare a probe labeled with digoxigenin (DIG) from the amplified DNA. This probe was used to screen the cDNA libraries.

Hybridization Conditions are as Follows.
Buffer: 5×SSC, 1% SDS, 50 mM Tris-HCl (pH 7.5), 50% formamide;
Temperature: 42° C. (overnight);
Washing conditions: 3 times in a solution of 0.2×SSC, 0.1% SDS (65° C.) for 20 minutes.
Detection was accomplished by using a DIG nucleic acid detection kit (Roche Diagnostics). Plasmids were excised by in vivo excision from phage clones obtained by screening to yield each plasmid DNA. The plasmid having the longest insert among those obtained by screening with LPLAT5 probe 1 was designated pB-LPLAT5, and the plasmid having the longest insert among those obtained by screening with LPLAT6 probe 1 was designated pB-LPLAT6. The nucleotide sequence of the insert of plasmid pB-LPLAT5, i.e., the cDNA of LPLAT5 was SEQ ID NO: 4, while the nucleotide sequence of the insert of plasmid pB-LPLAT6, i.e., the cDNA of LPLAT6 was SEQ ID NO: 9.

Sequence Analysis

The cDNA sequence of LPLAT5, i.e., SEQ ID NO: 4 contained a CDS consisting of nucleotides 161-1693 (SEQ ID NO: 3) and an ORF consisting of nucleotides 161-1690 (SEQ ID NO: 1). The cDNA sequence of LPLAT5 and its deduced amino acid sequence were described in FIG. 2.

On the other hand, the cDNA sequence of LPLAT6, i.e., SEQ ID NO: 9 contained a CDS consisting of nucleotides 38-1759 (SEQ ID NO: 8) and an ORF consisting of nucleotides 38-1756 (SEQ ID NO: 6). The cDNA sequence of LPLAT6 and its deduced amino acid sequence were described in FIG. 3.

SEQ ID NO: 1 and SEQ ID NO: 6 were subjected to homology analysis using BLASTX against amino acid sequences deposited in GENEBANK. The amino acid sequence deduced from SEQ ID NO: 1 showed homology to LPLAT homologs from fungi, while the amino acid sequence deduced from SEQ ID NO: 6 showed homology to LPLAT homologs from animals. The amino acid sequences showing the lowest E-value or the highest identity to each sequence were as follows. The nucleotide sequence identity and amino acid sequence identity of the sequence showing the highest identity to the ORF of each sequence were determined by clustalW and also reported below.

SEQ ID NO: 1 had 43.2% nucleotide sequence identity and 33.3% amino acid sequence identity in ORF to a lysophospholipid acyltransferase homolog from *Schizosaccharomyces pombe* (GI:161085648). On the other hand, SEQ ID NO: 6 had 41.2% nucleotide sequence identity and 28.6% amino acid sequence identity in ORF to a putative protein from *Xenopus laevis* (GI:56788919). The nucleotide sequence identity and amino acid sequence identity in ORF between LPLAT and LPLAT6 are 40.0% and 19.1%, respectively.

Figure 4B:
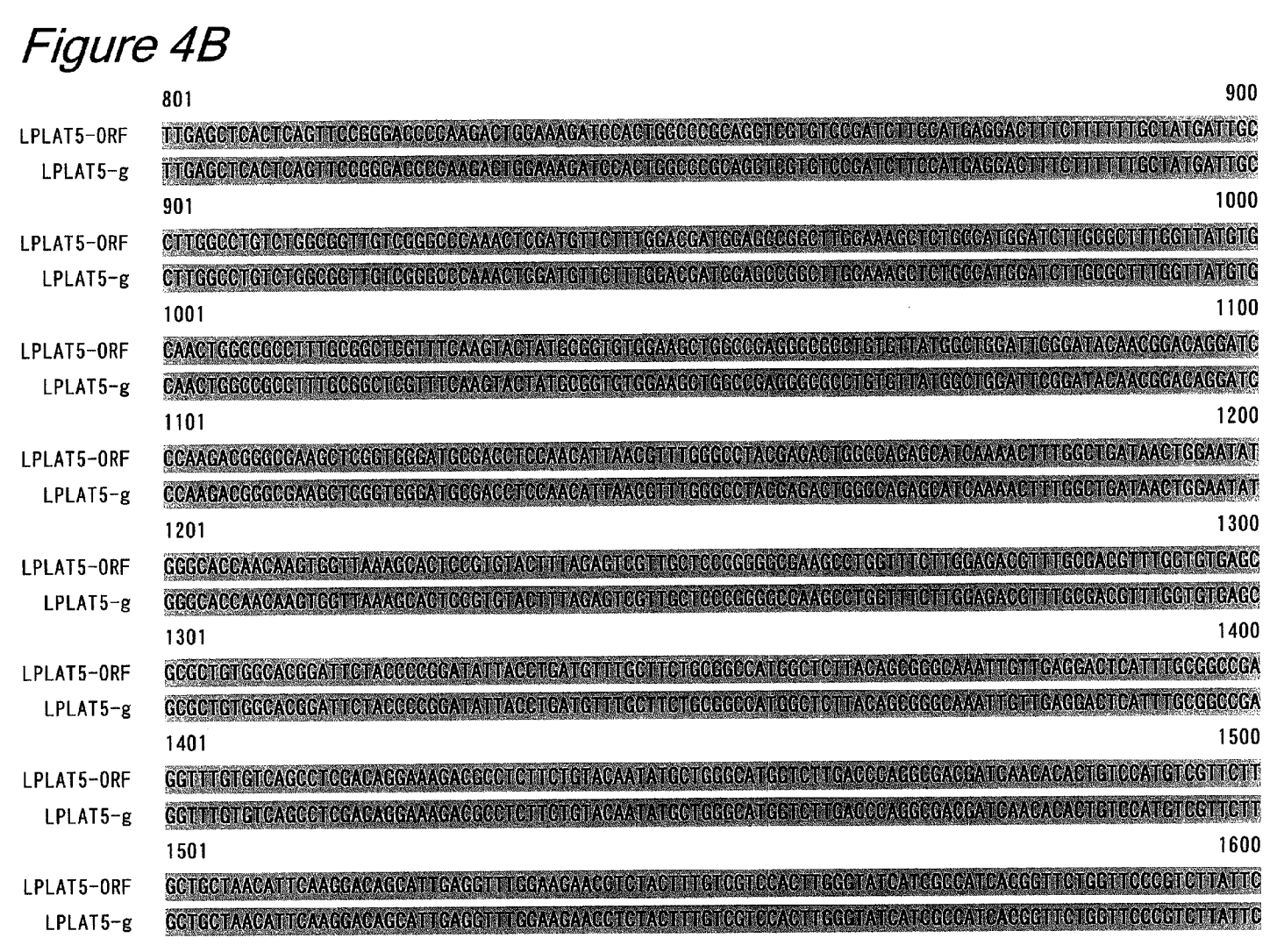
Figure 5A:
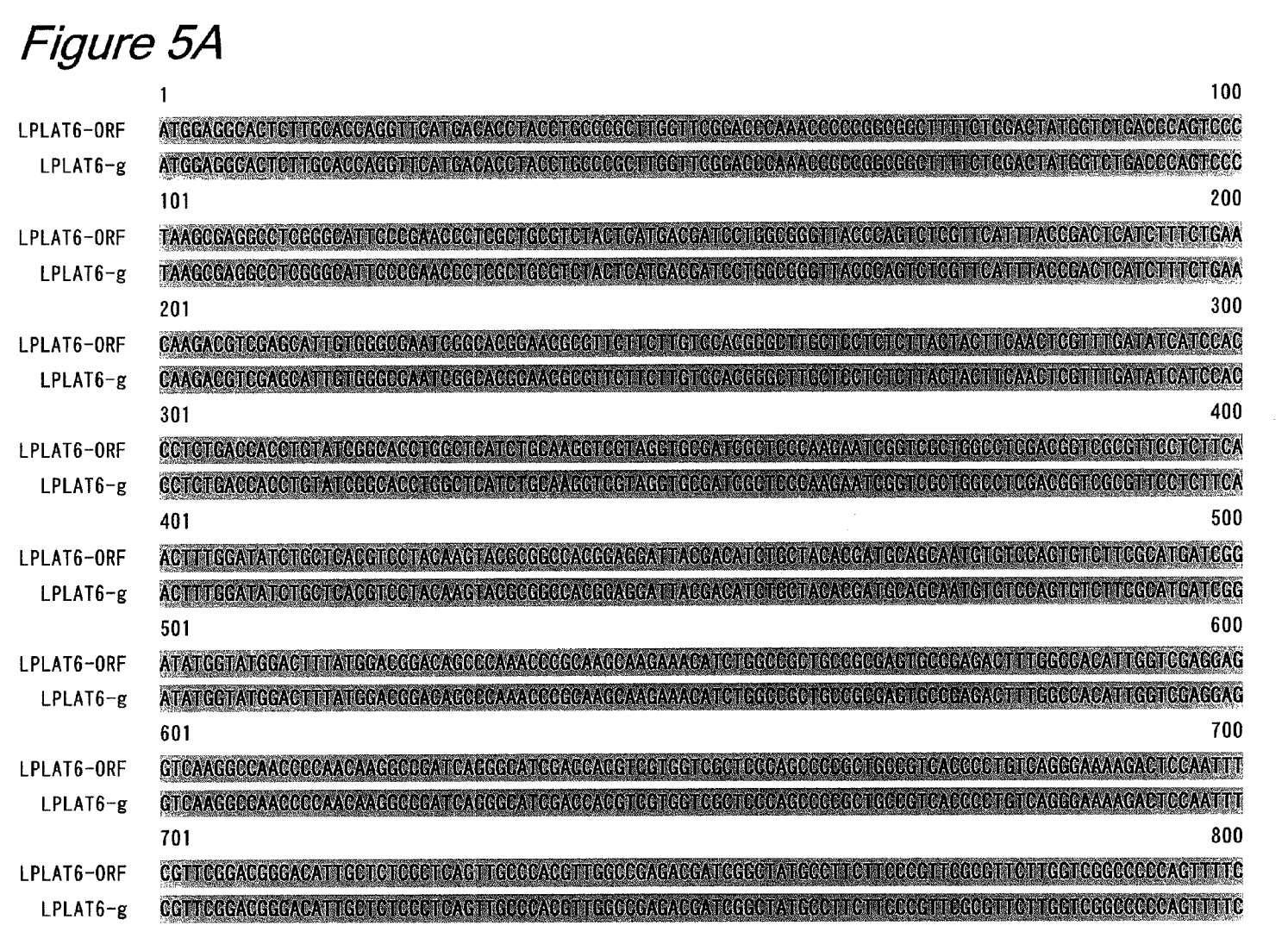
Figure 5B:
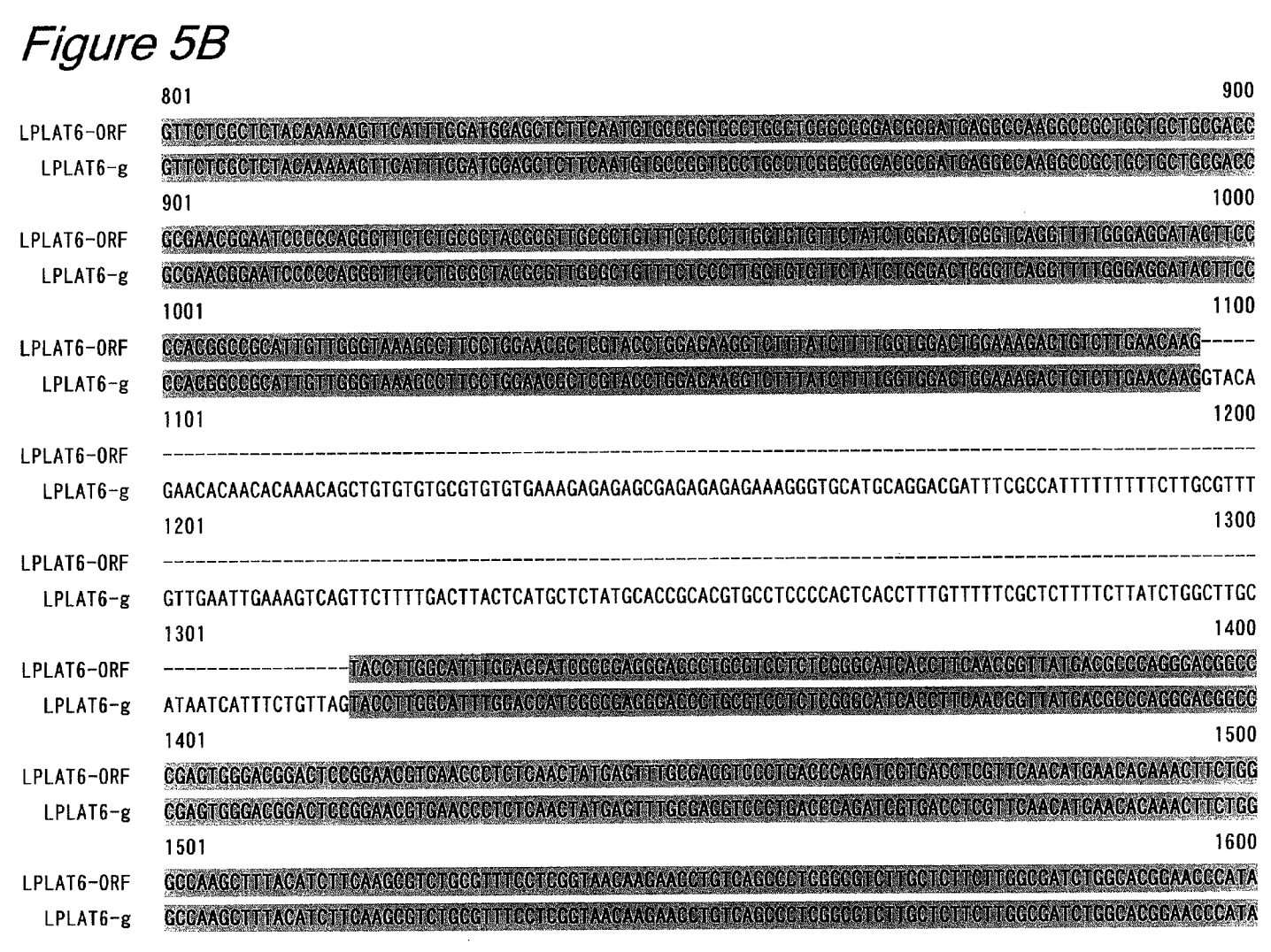
Figure 5C:
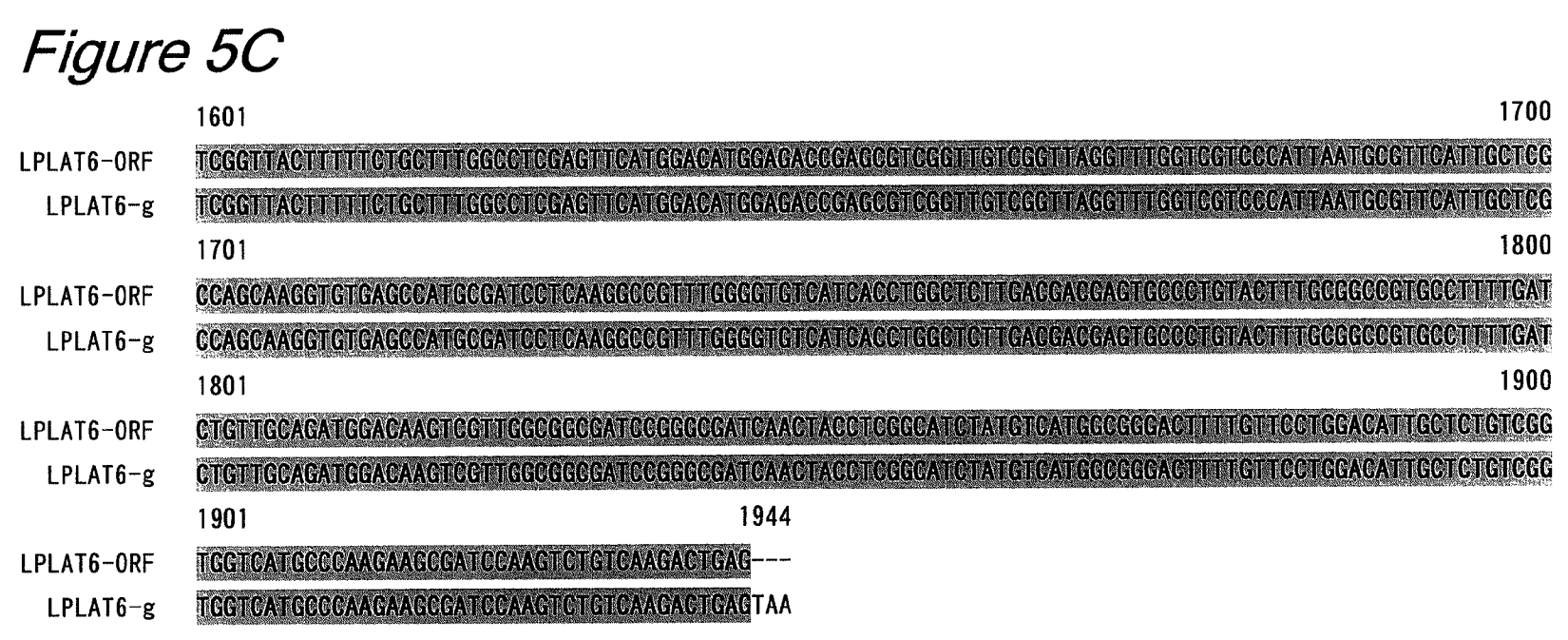

The genomic sequences containing the CDS of LPLAT5 (SEQ ID NO: 3) and the CDS of LPLAT6 (SEQ ID NO: 8) were described in SEQ ID NO: 5 and SEQ ID NO: 10, respectively. SEQ ID NO: 5 contained two introns and exons corresponding to nucleotides 1-314, 461-587, and 668-1759. On the other hand, SEQ ID NO: 10 contained one intron and exons corresponding to nucleotides 1-1095 and 1318-1944. FIG. 4 depicts the alignment between the genomic sequence and ORF sequence of LPLAT5, and FIG. 5 depicts the alignment between the genomic sequence and ORF sequence of LPLAT6.

Example 2

Construction of Yeast Expression Vectors

In order to express LPLAT5 and LPLAT6 in yeast, vectors were constructed as follows.
Using pBLPLAT5 as a template, PCR was performed with ExTaq (Takara Bio) and primer Eco-MaLPLAT5-F (SEQ ID NO: 15):

GAATTCATGCTAAACTCATTCTTCGGGGACGC and primer Xho-MaLPLAT5-R(SEQ ID NO: 16):

CTCGAGTTACAGCGTCTTGATTTTAACTGCAGC.

The resulting DNA fragments were TA-cloned using a TOPO-TA cloning Kit (INVITROGEN), and the nucleotide sequence of the insert was determined to give a plasmid having a correct nucleotide sequence designated pCR-LPLAT5. A DNA fragment of about 1.6 kb obtained by digesting this plasmid with restriction endonucleases EcoRI and XhoI was inserted into the EcoRI-SalI site of a yeast expression vector pYE22m (Appl. Microbiol. Biotechnol., 30, 515-520, 1989) to generate plasmid pYE-MALPLAT5.

On the other hand, a DNA fragment of 1.9 kb obtained by digesting pBLPLAT6 with restriction endonucleases EcoRI and KpnI was inserted into the EcoRI-KpnI site of the yeast-expressing vector pYE22m to generate plasmid pYE-LPLAT6.

Expression in Arachidonic Acid-Producing Yeast
(1) Breeding of Arachidonic Acid-Producing Yeast
To breed arachidonic acid-producing yeast (*S. cerevisiae*), the following plasmids were constructed.

First, PCR was performed using cDNA prepared from *M. alpina* strain 1S-4 as a template with ExTaq and the following primer set: Δ12-f/Δ12-r, Δ6-f/Δ6-r, GLELO-f/GLELO-r or Δ5-f/Δ5-r to amplify the Δ12 fatty acid desaturase gene, Δ6 fatty acid desaturase gene, GLELO fatty acid elongase gene and Δ5 fatty acid desaturase gene of *M. alpina* strain 1S-4.

```
Δ12-f:    TCTAGAATGGCACCTCCCAACACTATTG            (SEQ ID NO: 17)

Δ12-r:    AAGCTTTTACTTCTTGAAAAAGACCACGTC          (SEQ ID NO: 18)

Δ6-f:     TCTAGAATGGCTGCTGCTCCCAGTGTGAG           (SEQ ID NO: 19)

Δ6-r:     AAGCTTTTACTGTGCCTTGCCCATCTTGG           (SEQ ID NO: 20)

GLELO-f:  TCTAGAATGGAGTCGATTGCGCAATTCC            (SEQ ID NO: 21)

GLELO-r:  GAGCTCTTACTGCAACTTCCTTGCCTTCTC          (SEQ ID NO: 22)

Δ5-f:     TCTAGAATGGGTGCGGACACAGGAAAAACC          (SEQ ID NO: 23)

Δ5-r:     AAGCTTTTACTCTTCCTTGGGACGAAGACC.         (SEQ ID NO: 24)
```

These were cloned using a TOPO-TA-cloning Kit. The nucleotide sequences were identified, and the clones containing the nucleotide sequences were designated as plasmids pCR-MAΔ12DS (containing the nucleotide sequence of SEQ ID NO: 25), pCR-MAΔ6DS (containing the nucleotide sequence of SEQ ID NO: 26), pCR-MAGLELO (containing the nucleotide sequence of SEQ ID NO: 27), and pCR-MAΔ5DS (containing the nucleotide sequence of SEQ ID NO: 28).

A DNA fragment of about 1.2 kb obtained by digesting plasmid pURA34 (JP 2001-120276 A) with restriction endonuclease HindIII was inserted into the HindIII site of a vector obtained by digesting the vector pUC18 with restriction endonucleases EcoRI and SphI followed by blunt-ending and self-ligating to generate a clone designated pUC-URA 3 with the EcoRI site of the vector at the 5'-end of URA 3. A DNA fragment of about 2.2 kb obtained by digesting YEp13 with restriction endonucleases SalI and XhoI was inserted into the SalI site of the vector pUC18 to generate a clone designated pUC-LEU2 with the EcoRI site of the vector at the 5'-end of LEU2.

Then, a DNA fragment of about 1.2 kbp obtained by digesting plasmid pCR-MAΔ12DS with restriction endonuclease HindIII followed by blunt-ending and further digesting it with restriction endonuclease XbaI was ligated to a DNA fragment of about 6.6 kbp obtained by digesting the vector pESC-URA (STRATAGENE) with restriction endonuclease SpeI followed by blunt-ending and further digesting it with restriction endonuclease SpeI to generate plasmid pESC-U-Δ12. A DNA fragment of about 1.6 kbp obtained by digesting plasmid pCR-MAΔ6DS with restriction endonuclease XbaI followed by blunt-ending and further digesting it with restriction endonuclease HindIII was ligated to a DNA fragment of about 8 kbp obtained by digesting plasmid pESC-U-Δ12 with restriction endonuclease SalI followed by blunt-ending and further digesting it with restriction endonuclease HindIII to generate plasmid pESC-U-Δ12:Δ6. A fragment of about 4.2 kb obtained by partially digesting this with restriction endonuclease PvuII was inserted into the SmaI site of pUC-URA 3 to generate plasmid pUC-URA-Δ12:Δ6.

A DNA fragment of about 0.95 kbp obtained by digesting plasmid pCR-MAGLELO with restriction endonucleases XbaI and SacI was ligated to a DNA fragment of about 7.7 kbp obtained by digesting the vector pESC-LEU (STRATAGENE) with restriction endonucleases XbaI and SacI to generate plasmid pESC-L-GLELO. A DNA fragment of about 1.3 kbp obtained by digesting plasmid pCR-MAΔ5DS with restriction endonuclease XbaI followed by blunt-ending and further digesting it with restriction endonuclease HindIII was ligated to a DNA fragment of about 8.7 kbp obtained by digesting plasmid pESC-L-GLELO with restriction endonuclease ApaI followed by blunt-ending and further digesting it with restriction endonuclease HindIII to generate plasmid pESC-L-GLELO:Δ5. A fragment of about 3.2 kb obtained by digesting this with restriction endonuclease PvuII was inserted into the SmaI site of pUC-LEU2 to generate plasmid pUC-LEU-GLELO:Δ5. *S. cerevisiae* strain YPH499 (STRATAGENE) was co-transformed with plasmid pUC-URA-Δ12:Δ6 and plasmid pUC-LEU-GLELO:Δ5. Transformed strains were selected by viability on SC-Leu, Ura agar medium (2% agar) containing, per liter, 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine, 6 g threonine and 1.2 g tryptophan). Random one of the selected strains was designated as ARA3-1 strain. This strain can produce arachidonic acid by expressing the Δ12 fatty acid desaturase gene, Δ6 fatty acid desaturase gene, GLELO fatty acid elongase gene, and Δ5 fatty acid desaturase gene from the GAL1/10 promoter upon cultivation in a galactose-containing medium.

(2) Transformation of Arachidonic Acid-Producing Yeast
ARA3-1 strain was transformed with plasmids pYE22m, pYE-MALPLAT5, and pYE-MALPLAT6. Transformed strains were selected by viability on SC-Trp, Leu, Ura agar medium (2% agar) containing, per liter, 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine, and 6 g threonine). Random three strains transformed with each plasmid were used for the subsequent cultivation. In Tables 3-8 below, control represents strains transformed with plasmid pYE22m, LPLAT5 represents strains transformed with plasmid pYE-MALPLAT5, and LPLAT6 represents strains transformed with plasmid pYE-MALPLAT6.

(3) Cultivation in a Fatty Acid Free Medium

The above transformed strains were cultured with shaking in 10 ml of SC-Trp, Leu, Ura liquid medium at 30° C. for 1 day, and 1 ml of the cultures were incubated with shaking in 10 ml of SG-Trp, Leu, Ura liquid medium containing, per liter, 6.7 g Yeast nitrogen base w/o amino acids (DIFCO), 20 g galactose and 1.3 g amino acid powder (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine, and 6 g threonine) at 15° C. for 6 days. The cells were harvested, washed with water and then lyophilized and subjected to fatty acid analysis.

The results are shown in Table 3.

TABLE 3

Compositional ratio of fatty acids in yeast cells expressing each gene (%)

| | cultured in a fatty acid-free medium | | |
|---|---|---|---|
| | Control | LPLAT5 | LPLAT6 |
| 16:0 | 22.16 ± 0.42 | 20.88 ± 0.13 | 20.38 ± 0.13 |
| 16:1 | 28.79 ± 0.55 | 30.81 ± 0.32 | 30.22 ± 0.31 |
| 18:0 | 10.35 ± 0.23 | 9.98 ± 0.08 | 9.81 ± 0.11 |
| 18:1 | 20.28 ± 0.30 | 17.08 ± 0.17 | 20.81 ± 0.21 |
| 18:2 | 7.61 ± 0.05 | 9.16 ± 0.15 | 8.10 ± 0.09 |
| 18:3 (n-6) | 0.47 ± 0.03 | 0.18 ± 0.01 | 0.11 ± 0.02 |
| DGLA | 0.46 ± 0.01 | 0.40 ± 0.02 | 0.00 ± 0.00 |
| ARA | 0.38 ± 0.02 | 0.58 ± 0.03 | 0.89 ± 0.03 |
| other | 9.51 ± 0.94 | 11.03 ± 0.77 | 9.68 ± 0.15 | mean ± SD

Based on the results in Table 3, the conversion of a fatty acid to another fatty acid in the arachidonic acid synthetic pathway was determined. For example, the conversion of 18:2→18:3(n-6) is determined as follows:

Conversion=(18:3(n-6)+DGLA+ARA)/(18:2+18:3(n-6)+DGLA+ARA)×100

The results are shown in Table 4.

TABLE 4

Conversions of fatty acids in the arachidonic acid biosynthetic pathway (%)

| | cultured in a fatty acid-free medium | | |
|---|---|---|---|
| | Control | LPLAT5 | LPLAT6 |
| 18:1→18:2 | 29.63 ± 0.28 | 36.09 ± 0.39 | 28.29 ± 0.40 |
| 18:2→18:3(n-6) | 14.63 ± 0.55 | 11.33 ± 0.35 | 10.99 ± 0.42 |
| 18:3(n-6)→DGLA | 64.15 ± 0.85 | 84.50 ± 0.91 | 88.81 ± 1.81 |
| DGLA→ARA | 45.17 ± 1.61 | 59.02 ± 0.30 | 100.00 ± 0.00 | mean ± SD

As shown in Tables 3 and 4, the proportion of arachidonic acid to total fatty acids increased 1.5-fold in the LPLAT5-expressing strains and 2.3-fold in the LPLAT6-expressing strains as compared with the control. The conversions of fatty acids in the arachidonic acid biosynthetic pathway were reviewed, revealing that the conversions of 18:1→18:2, 18:3(n-6)→DGLA, and DGLA→ARA increased in the LPLAT5-expressing strains while the conversion of DGLA→ARA remarkably increased in the LPLAT6-expressing strains. These conversions required acyl transfer from acyl-CoA to phospholipids or from phospholipids to CoA as shown in FIG. 1, suggesting that LPLAT5 and LPLAT6 are involved in these conversions.

(4) Cultivation in a Medium Containing Linoleic Acid

The transformed strains were cultured with shaking in 10 ml of SC-Trp, Leu, Ura liquid medium at 30° C. for 1 day, and 1 ml of the cultures were inoculated into 10 ml of SG-Trp, Leu, Ura liquid medium containing 5 mg/ml linoleic acid and 0.1% Triton X-100 and incubated with shaking at 15° C. for 6 days. Cells were harvested, washed with water and then lyophilized and subjected to fatty acid analysis. The results are shown in Table 5.

TABLE 5

Compositional ratio of fatty acids in yeast cells expressing each gene (%)

| | cultured in a medium containing linoleic acid | | |
|---|---|---|---|
| | Control | LPLAT5 | LPLAT6 |
| 16:0 | 21.30 ± 0.44 | 19.20 ± 0.10 | 21.45 ± 0.22 |
| 16:1 | 17.33 ± 0.56 | 17.98 ± 0.10 | 18.69 ± 0.20 |
| 18:0 | 7.82 ± 0.43 | 7.74 ± 0.05 | 8.05 ± 0.15 |
| 18:1 | 10.12 ± 0.26 | 9.21 ± 0.03 | 10.69 ± 0.17 |
| 18:2 | 36.05 ± 0.44 | 39.51 ± 0.05 | 34.53 ± 0.27 |
| 18:3(n-6) | 0.69 ± 0.06 | 0.35 ± 0.07 | 0.09 ± 0.06 |
| DGLA | 0.29 ± 0.02 | 0.29 ± 0.01 | 0.04 ± 0.09 |
| ARA | 0.12 ± 0.02 | 0.24 ± 0.01 | 0.42 ± 0.01 |
| other | 6.27 ± 0.25 | 5.50 ± 0.15 | 6.04 ± 0.29 | mean ± SD

Based on the results in Table 5, the conversion of a fatty acid to another fatty acid in the arachidonic acid synthetic pathway was determined. The results are shown in Table 6.

TABLE 6

Conversions of fatty acids in the arachidonic acid biosynthetic pathway (%)

| | Control | LPLAT5 | LPLAT6 |
|---|---|---|---|
| 18:2→18:3(n-6) | 2.97 ± 0.12 | 2.15 ± 0.22 | 1.57 ± 0.37 |
| 18:3(n-6)→DGLA | 37.65 ± 2.58 | 60.49 ± 4.53 | 85.08 ± 10.00 |
| DGLA→ARA | 29.66 ± 3.51 | 45.43 ± 1.86 | 92.72 ± 14.56 | mean ± SD

As shown in Table 5, the proportion of arachidonic acid to total fatty acids increased 2-fold in the LPLAT5-expressing strains and 3.5-fold in the LPLAT6-expressing strains as compared with the control. In the LPLAT5-expressing strains, the proportion of linoleic acid added increased as compared with the control. The conversions of fatty acids in the arachidonic acid biosynthetic pathway (Table 6) were reviewed, revealing that the conversions of 18:3(n-6)→DGLA and DGLA→ARA increased in both LPLAT5-expressing strains and LPLAT6-expressing strains, especially remarkably increased in the LPLAT6-expressing strains.

(5) Cultivation in a Medium Containing γ-Linolenic Acid

The transformed strains were cultured with shaking in 10 ml of SC-Trp, Leu, Ura liquid medium at 30° C. for 1 day, and 1 ml of the cultures were inoculated into 10 ml of SG-Trp, Leu, Ura liquid medium containing 5 mg/ml γ-linolenic acid and 0.1% Triton X-100 and incubated with shaking at 15° C. for 6 days. Cells were harvested, washed with water and then lyophilized and subjected to fatty acid analysis. The results are shown in Table 7.

TABLE 7

Compositional ratio of fatty acids in yeast cells expressing each gene (%)

| | cultured in a medium containing γ-linolenic acid | | |
|---|---|---|---|
| | Control | LPLAT5 | LPLAT6 |
| 16:0 | 20.97 ± 0.24 | 17.59 ± 0.06 | 22.02 ± 0.09 |
| 16:1 | 16.11 ± 1.02 | 17.28 ± 0.23 | 16.17 ± 0.37 |
| 18:0 | 8.54 ± 0.06 | 7.78 ± 0.08 | 9.59 ± 0.07 |
| 18:1 | 9.03 ± 0.86 | 8.80 ± 0.04 | 9.46 ± 0.17 |
| 18:2 | 4.57 ± 0.11 | 5.10 ± 0.04 | 5.02 ± 0.10 |
| 18:3(n-6) | 20.36 ± 1.67 | 25.28 ± 0.26 | 17.97 ± 0.78 |
| DGLA | 10.88 ± 0.29 | 9.60 ± 0.05 | 1.86 ± 0.07 |
| ARA | 4.74 ± 0.09 | 4.82 ± 0.04 | 13.50 ± 0.22 |
| other | 4.81 ± 0.11 | 3.75 ± 0.04 | 4.42 ± 0.06 | mean ± SD

Based on the results in Table 7, the conversion of a fatty acid to another fatty acid in the arachidonic acid synthetic pathway was determined (Table 8).

TABLE 8

Conversions of fatty acids downstream of γ-linolenic acid in the arachidonic acid biosynthetic pathway (%)

| | cultured in a medium containing γ-linolenic acid | | |
|---|---|---|---|
| | Control | LPLAT5 | LPLAT6 |
| 18:3(n-6)→DGLA | 43.25 ± 1.29 | 36.33 ± 0.27 | 46.10 ± 1.14 |
| DGLA→ARA | 31.70 ± 2.70 | 33.44 ± 0.26 | 87.91 ± 0.54 | mean ± SD

As shown in Table 7, the proportion of γ-linolenic acid added to total fatty acids increased in the LPLAT5-expressing strains. However, the proportions of the downstream products dihomo-γ-linolenic acid and arachidonic acid did not increase (Table 8). In contrast, the proportion of arachidonic acid to total fatty acids increased 2.8-fold as compared with the control and the conversion of DGLA→ARA significantly increased in the LPLAT6-expressing strains (Table 8).

These results show that LPLAT5 and LPLAT6 can increase the conversions of fatty acids requiring acyl transfer from acyl-CoA to phospholipids or from phospholipids to CoA. The involvement of LPLAT5 in the conversion from 18:1-CoA to 18:1-PL, conversion from 18:3(n-6)-PL to 18:3(n-6)-CoA and conversion from DGLA-CoA to DGLA-PL was suggested. On the other hand, the involvement of LPLAT6 in the conversion from 18:3(n-6)-PL to 18:3(n-6)-CoA and conversion from DGLA-CoA to DGLA-PL was suggested.

Example 3

Functional Analysis of LPLAT6 in *M. alpina*

Construction of *Mortierella* Expression Vectors

The following oligonucleotides were synthesized for use as adapters.

```
                                    (SEQ ID NO: 29)
A-1: GATCCGGCGCGCCGCGGCCGCTCTAGAGTCGACGGCGCGCCA (SEQ ID NO: 30)
A-2: AGCTTGGCGCGCCGTCGACTCTAGAGCGGCCGCGGCGCGCCG.
```

A-1 and A-2 were annealed and ligated to a fragment obtained by digesting the plasmid pUC18 with restriction endonucleases EcoRI and HindIII to generate pUC18-R.

Using genomic DNA or a plasmid prepared from *M. alpina* strain 1S-4 as a template, each DNA fragment was amplified by PCR using ExTaq (Takara Bio) with the following primer set and cloned using TOPO-TA cloning Kit (Invitrogen).

Specifically, genomic DNA was used as a template to amplify genomic DNA of about 2 kbp containing the URA 5 gene using the primer set:

```
                                    (SEQ ID NO: 31)
    primer URA5g-F1: GTCGACCATGACAAGTTTGC,
    and (SEQ ID NO: 32)
    primer URA5g-R1: GTCGACTGGAAGACGAGCACG;
``` to amplify the GAPDH promoter of about 0.9 kbp using the primer set:

```
                                    (SEQ ID NO: 33)
primer GAPDHp-F1: GTCGACGATCACGTCGGGTGATGAGTTG,
and (SEQ ID NO: 34)
primer GAPDHp-R1: TCTAGAGATGTTGAATGTGTGGTGTGTG;
``` and to amplify the GAPDH terminator of about 0.5 kbp using the primer set:

```
    primer GAPDHt-F1:
                                    (SEQ ID NO: 35)
    GCGGCCGCTAAGAAAAGGGAGTGAATCGC,
    and primer GAPDHt-R1:
                                    (SEQ ID NO: 36)
    GGATCCGGCGCGCCGATCCATGCACGGGTCCTTCTC.
```

Plasmid pB-LPLAT6 was used as a template to amplify the CDS of about 1.6 kbp of the LPLAT6 gene using the primer set:

```
    primer XbaI-LPLAT6-F1:
                                    (SEQ ID NO: 37)
    TCTAGAATGGAGGCACTCTTGCACCAGG,
    and primer NotI-LPLAT6-R1:
                                    (SEQ ID NO: 38)
    GCGGCCGCTTACTCAGTCTTGACAGACTTG;
``` and to amplify a 3'-fragment of about 0.7 kbp of the CDS of the LPLAT6 gene using the primer set:

```
    primer EcoRV-LPLAT6-F2:
                                    (SEQ ID NO: 39)
    GATATCGGGTAAAGCCTTCCTGGAACG,
    and primer XbaI-LPLAT6-R2:
                                    (SEQ ID NO: 40)
    TCTAGATTACTCAGTCTTGACAGACTTGGATCG.
```

Likewise, plasmid pCR-MAΔ5DS was used as a template to amplify the CDS of about 1.3 kbp of the Δ5 fatty acid desaturase gene using the primer set:

```
    primer XbaI-Δ5DS-F1:
                                    (SEQ ID NO: 41)
    TCTAGAATGGGTGCGGACACAGGAAAAAC,
    and
```

-continued primer NotI-Δ5DS-R1:
(SEQ ID NO: 42)
GCGGCCGCTTACTCTTCCTTGGGACGAAG;

and to amplify a 3'-fragment of about 0.5 kbp of the CDS of the Δ5 fatty acid desaturase gene using the primer set:

(SEQ ID NO: 43)
primer NdeI-Δ5DS-R2: TCTAGATTACTCTTCCTTGGGACGAAG,
and (SEQ ID NO: 44)
primer XbaI-Δ5DS-F2: CATATGCATCCAGGACATCAACATCTTG.

Into the restriction endonuclease EcoRI/NotI sites of plasmid pUC18-R was inserted a fragment excised with the same restriction endonucleases from the GAPDH terminator to generate plasmid pUC-GAPDHt. Subsequently, plasmid pUC-GAPDHt was cleaved with restriction endonucleases XbaI and SalI, and a fragment excised with the same restriction endonucleases from the GAPDH promoter was inserted to generate plasmid pUC-GAPDHpt. Plasmid pUC-GAPDHpt was cleaved with restriction endonuclease SalI, and a fragment cleaved with the same restriction endonuclease from the genomic DNA containing the URA 5 gene was inserted. The orientations of the inserts were confirmed and a vector containing the URA 5 gene inserted in the same orientation as that of the restriction endonuclease sites EcoRI→HindIII was selected and designated as plasmid pDUraRSC.

Plasmid pDUraRSC was cleaved with restriction endonucleases XbaI and NotI, and a DNA fragment excised with the same restriction endonucleases from the CDS of the LPLAT6 gene was inserted to generate plasmid pDUraRSC-LPLAT6. A DNA fragment of about 7 kbp obtained by cleaving plasmid pDUraRSC-LPLAT6 with restriction endonucleases EcoRV and XbaI was ligated to a DNA fragment excised with the same restriction endonucleases from the 3'-fragment of about 0.7 kbp of the CDS of the LPLAT6 gene to generate plasmid pDUraRSC-LPLAT6-RNAi.

Construction of Vectors with Suppressed Expression of Δ5DS (RNAi)

Plasmid pDUraRSC was cleaved with restriction endonucleases XbaI and NotI, and a DNA fragment excised with the same restriction endonucleases from the CDS of the Δ5 fatty acid desaturase gene to generate plasmid pDUraRSC-Δ5DS. A DNA fragment of about 1.2 kbp obtained by cleaving plasmid pDUraRSC-Δ5DS with restriction endonucleases EcoRI and NdeI was ligated to a DNA fragment of about 5.5 kbp obtained by cleaving it with restriction endonucleases XbaI and EcoRI and a fragment excised with restriction endonucleases NdeI and XbaI from the 3'-fragment of about 0.5 kbp of the CDS of the Δ5 fatty acid desaturase gene to generate plasmid pDUraRSC-Δ5DS-RNAi.

Acquisition of Transformed M. alpina Strains

An uracil-auxotrophic strain Aura-3 derived from M. alpina according to a method described in a patent document (WO2005/019437 entitled "Method of Breeding Lipid-Producing Fungus") in plasmid pDUraRSC-LPLAT6-RNAi or plasmid pDUraRSC-Δ5DS-RNAi was used as a host and transformed by the particle delivery method. SC agar medium (0.5% Yeast Nitrogen Base w/o Amino Acids and Ammonium Sulfate (Difco), 0.17% ammonium sulfate, 2% glucose, 0.002% adenine, 0.003% tyrosine, 0.0001% methionine, 0.0002% arginine, 0.0002% histidine, 0.0004% lysine, 0.0004% tryptophan, 0.0005% threonine, 0.0006% isoleucine, 0.0006% leucine, 0.0006% phenylalanine, and 2% agar) was used for selecting transformed strains.

Evaluation of Transformed M. alpina Strains

About 50 strains transformed with each plasmid were inoculated into 4 ml of GY medium (2% glucose, 1% yeast extract, pH 6.0) and cultured with shaking at 28° C. for 4 days. At the end of the cultivation, cells were harvested by filtration and lyophilized. A part of the lyophilized cells (about 10-20 mg) were collected, and fatty acids in the cells were converted into methyl esters using methanolic HCl, then extracted with hexane, and hexane was distilled off and the residue was subjected to fatty acid analysis by gas chromatography. Among the strains transformed with the different plasmids, those having a higher proportion of dihomo-γ-linolenic acid than the proportion of arachidonic acid, i.e., LPLAT6-D#6 (transformed with plasmid pDUraRSC-LPLAT6-RNAi) and Δ5DS-D#45 (transformed with plasmid pDUraRSC-Δ5DS-RNAi) were selected.

Figure 7:
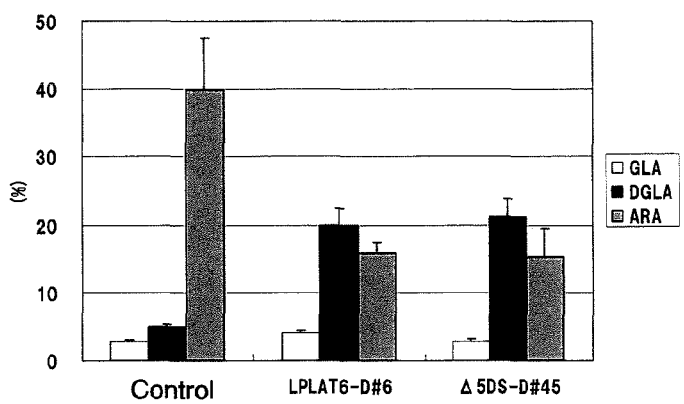
FIG. 7 is a graph showing the composition ratio of polyunsaturated fatty acids in triacylglycerol fractions when the expression of LPLAT6 or Δ5 fatty acid desaturase is suppressed in *M. alpina*.
Figure 8:
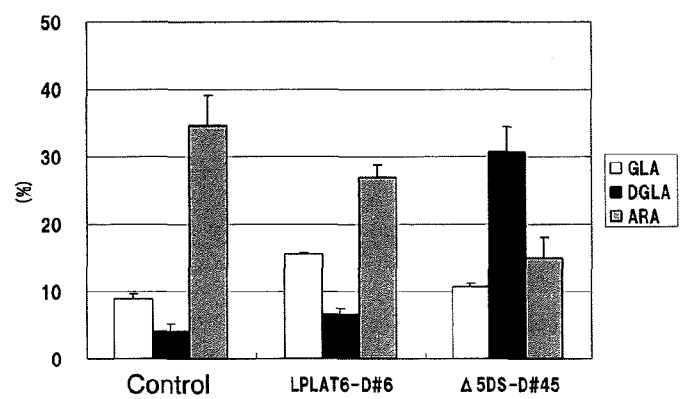
FIG. 8 is a graph showing the composition ratio of polyunsaturated fatty acids in phospholipid fractions when the expression of LPLAT6 or Δ5 fatty acid desaturase is suppressed in *M. alpina*.

These two strains and a control (wild-type M. alpina strain 1S-4) were cultured with shaking in 4 ml of GY medium at 28° C. for 4 days. At the end of the cultivation, cells were harvested by filtration and lyophilized. A part of the lyophilized cells (about 10-20 mg) were collected, and mechanically disrupted. The cells were maintained in 4 ml of chloroform-methanol (2:1) at 70° C. for 1 hour with intermittent stirring, and then centrifuged to collect the supernatant. The remaining cells were maintained in another 4 ml of chloroform-methanol (2:1) at 70° C. for 1 hour with intermittent stirring, and then centrifuged to collect the supernatant, which was combined with the previous supernatant. Lipids were dried in a SpeedVac centrifuge concentrator, and dissolved in 5 ml of chloroform. One ml of the solution was dried in the same manner as described above, and fatty acids were converted into methyl esters using methanolic HCl and subjected to fatty acid analysis. On the other hand, 2 ml of the solution in chloroform was also dried in the same manner as described above, and dissolved in a small amount of chloroform and the total amount of the solution was subjected to thin-layer chromatography as follows. Lipids were fractionated by thin-layer chromatography on silica gel 60 plates (Merck), eluting with hexane:diethyl ether:acetic acid of 70:30:1. The plates were sprayed with an aqueous solution containing 0.015% Primuline, 80% acetone (Primuline solution), and lipids were visualized by UV irradiation, whereby triacylglycerol (TG) fractions and phospholipid (PL) fractions were marked with a pencil and the silica gel in the marked areas was scraped off and collected in test tubes. Fatty acids were converted into methyl esters using methanolic HCl and subjected to fatty acid analysis by gas chromatography. Thus, fatty acids were converted into methyl esters by a reaction with 1 ml of dichloromethane and 2 ml of 10% methanolic HCl at 50° C. for 3 hours. Then, 4 ml of hexane and 1 ml of water were added and the solution was vigorously stirred and then centrifuged and the upper layer was collected. The solvent was distilled off in a SpeedVac and the residue was dissolved in acetonitrile and subjected to fatty acid analysis by gas chromatography. The results are shown in FIGS. 6-8.

Figure 6:
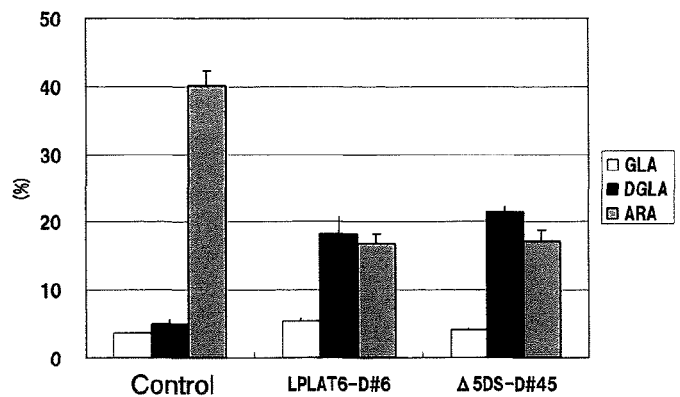
FIG. 6 is a graph showing the composition ratio of polyunsaturated fatty acids in cells when the expression of LPLAT6 or Δ5 fatty acid desaturase is suppressed in *M. alpina*.

FIG. 6 shows the composition ratio of polyunsaturated fatty acids in total lipids extracted with chloroform-methanol (2:1). In contrast to the control containing a high proportion of arachidonic acid, LPLAT6-D#6 strain and Δ5DS-D#45 strain showed comparable proportions of dihomo-γ-linolenic acid and arachidonic acid because of the inhibition of the conversion from dihomo-γ-linolenic acid to arachidonic acid. FIG. 7 shows the composition ratio of polyunsaturated fatty acids in triacylglycerols constituting a major portion of lipids in cells. Similarly to the composition ratio in total lipids in cells, LPLAT6-D#6 strain and Δ5DS-D#45 strain showed a higher proportion of dihomo-γ-linolenic acid as compared with the control. However, the fatty acid composition ratio in phospholipid fractions shown in FIG. 8 differed greatly between LPLAT6-D#6 strain and Δ5DS-D#45 strain. Specifically, Δ5DS-D#45 strain showed a high proportion of dihomo-γ-linolenic acid, while LPLAT6-D#6 strain showed a high proportion of arachidonic acid but behind the control and also showed a high proportion of γ-linolenic acid as compared with the control and Δ5DS-D#45 strain.

The biosynthetic pathway of arachidonic acid in *M. alpina* is presumed to proceed as shown in FIG. 1. The experiments described above also strongly suggested that the 05 fatty acid desaturase acts on DGLA-PL to produce arachidonic acid. In contrast, 18:3(n-6)-PL accumulated in the strains with suppressed expression of LPLAT6. The proportion of DGLA in TG fractions increased, but no significant increase of the proportion of DGLA was observed in PL fractions. These results strongly suggested that LPLAT6 is responsible for the conversion of 18:3(n-6)-PL to 18:3(n-6)-CoA and the conversion of DGLA-CoA to DGLA-PL in *M. alpina*.

Sequence Listing Free Text
SEQ ID NO: 11: primer
SEQ ID NO: 12: primer
SEQ ID NO: 13: primer
SEQ ID NO: 14: primer
SEQ ID NO: 15: primer
SEQ ID NO: 16: primer
SEQ ID NO: 17: primer
SEQ ID NO: 18: primer
SEQ ID NO: 19: primer
SEQ ID NO: 20: primer
SEQ ID NO: 21: primer
SEQ ID NO: 22: primer
SEQ ID NO: 23: primer
SEQ ID NO: 24: primer
SEQ ID NO: 29: adapter A-1
SEQ ID NO: 30: adapter A-2
SEQ ID NO: 31: primer URA 5g-F1
SEQ ID NO: 32: primer URA 5g-R1
SEQ ID NO: 33: primer GAPDHp-F1
SEQ ID NO: 34: primer GAPDHp-R1
SEQ ED NO: 35: primer GAPDHt-F1
SEQ ID NO: 36: primer GAPDHt-R1
SEQ ID NO: 37: primer XbaI-LPLAT6-F1
SEQ ID NO: 38: primer NotI-LPLAT6-R1
SEQ ID NO: 39: primer EcoRV-LPLAT6-F2
SEQ ID NO: 40: primer XbaI-LPLAT6-R2
SEQ ID NO: 41: primer XbaI-Δ5DS-F1
SEQ ID NO: 42: primer NotI-Δ5DS-R1
SEQ ID NO: 43: primer NdeI-Δ5DS-F1
SEQ ID NO: 44: primer XbaI-Δ5DS-R1

The invention claimed is:

1. A cDNA or recombinant vector comprising a nucleic acid of any one of (a)-(e) below:
   (a) a nucleic acid that comprises a nucleotide sequence encoding a protein consisting of an amino acid sequence with deletion, substitution or addition of one to 50 amino acids in the amino acid sequence shown in SEQ ID NO: 7, and having lysophospholipid acyltransferase activity;
   (b) a nucleic acid that hybridizes under hybridization conditions of 0.1×SSC-1×SSC at 60° C.-65° C. and washing conditions of 0.2×SSC-2×SSC at 50° C.-68° C. to a nucleic acid consisting of a full length complement to the nucleotide sequence consisting of SEQ ID NO: 6 and that comprises a nucleotide sequence encoding a protein having lysophospholipid acyltransferase activity;
   (c) a nucleic acid that comprises a nucleotide sequence sharing an identity of 90% or more with the nucleotide sequence consisting of SEQ ID NO: 6 and encoding a protein having lysophospholipid acyltransferase activity;
   (d) a nucleic acid that comprises a nucleotide sequence encoding a protein consisting of an amino acid sequence sharing an identity of 90% or more with the amino acid sequence consisting of SEQ ID NO: 7 and having lysophospholipid acyltransferase activity; and
   (e) a nucleic acid that hybridizes under conditions of 0.1×SSC-1×SSC at 60° C.-65° C. and washing conditions of 0.2×SSC-2×SSC at 50° C.-68° C. to a nucleic acid consisting of a full length complement to a nucleotide sequence encoding a protein consisting of the amino acid sequence shown in SEQ ID NO: 7 and that comprises a nucleotide sequence encoding a protein having lysophospholipid acyltransferase activity.

2. A cDNA or recombinant vector comprising a nucleic acid of any one of (a)-(e) below:
   (a) a nucleic acid that comprises a nucleotide sequence encoding a protein consisting of an amino acid sequence with deletion, substitution or addition of one to 50 amino acids in the amino acid sequence shown in SEQ ID NO: 7, and having the activity of increasing the proportion of arachidonic acid in the compositional ratio of fatty acids in a host transformed with a recombinant vector containing the nucleic acid as compared with the proportion in the compositional ratio of fatty acids in a host that has not been transformed with the vector;
   (b) a nucleic acid that hybridizes under hybridization conditions of 0.1×SSC-1×SSC at 60° C.-65° C. and washing conditions of 0.2×SSC-2×SSC at 50° C.-68° C. to a nucleic acid consisting of a full length complement to the nucleotide sequence consisting of SEQ ID NO: 6 and that comprises a nucleotide sequence encoding a protein having the activity of increasing the proportion of arachidonic acid in the compositional ratio of fatty acids in a host transformed with a recombinant vector containing the nucleic acid as compared with the proportion in the compositional ratio of fatty acids in a host that has not been transformed with the vector;
   (c) a nucleic acid that comprises a nucleotide sequence sharing an identity of 90% or more with the nucleotide sequence consisting of SEQ ID NO: 6 and encoding a protein having the activity of increasing the proportion of arachidonic acid in the compositional ratio of fatty acids in a host transformed with a recombinant vector containing the nucleic acid as compared with the proportion in the compositional ratio of fatty acids in a host that has not been transformed with the vector;
   (d) a nucleic acid that comprises a nucleotide sequence encoding a protein consisting of an amino acid sequence sharing an identity of 90% or more with the amino acid sequence consisting of SEQ ID NO: 7 and having the activity of increasing the proportion of arachidonic acid in the compositional ratio of fatty acids in a host transformed with a recombinant vector containing the nucleic acid as compared with the proportion in the compositional ratio of fatty acids in a host that has not been transformed with the vector; and
   (e) a nucleic acid that hybridizes under hybridization conditions of 0.1×SSC-1×SSC at 60° C.-65° C. and washing conditions of 0.2×SSC-2×SSC at 50° C.-68° C. to a nucleic acid consisting of a full length complement to a nucleotide sequence encoding a protein consisting of the amino acid sequence shown in SEQ ID NO: 7 and that comprises a nucleotide sequence encoding a protein having the activity of increasing the proportion of arachidonic acid in the compositional ratio of fatty acids in a host transformed with a recombinant vector containing the nucleic acid as compared with the proportion in the compositional ratio of fatty acids in a host that has not been transformed with the vector.

3. The cDNA or recombinant vector of claim 1 wherein the encoded protein belongs to the membrane-bound O-acyltransferase family.

4. A cDNA or recombinant vector comprising a nucleic acid of (a) or (b) below:
   (a) a nucleic acid that comprises the nucleotide sequence shown in SEQ ID NO: 6; or
   (b) a nucleic acid that comprises a nucleotide sequence encoding a protein consisting of the amino acid sequence shown in SEQ ID NO: 7.

5. An isolated protein of (a) or (b) below:
   (a) a protein consisting of an amino acid sequence with deletion, substitution or addition of one to 50 amino acids in the amino acid sequence of SEQ ID NO: 7, and having lysophospholipid acyltransferase activity; or
   (b) a protein consisting of an amino acid sequence sharing an identity of 90% or more with the amino acid sequence consisting of SEQ ID NO: 7 and having lysophospholipid acyltransferase activity.

6. An isolated protein of (a) or (b) below:
   (a) a protein consisting of an amino acid sequence with deletion, substitution or addition of one to 50 amino acids in the amino acid sequence of SEQ ID NO: 7, and having the activity of increasing the proportion of arachidonic acid in the compositional ratio of fatty acids in a host transformed with a recombinant vector containing a nucleic acid encoding the amino acid sequence as compared with the proportion in the compositional ratio of fatty acids in a host that has not been transformed with the vector; or
   (b) a protein consisting of an amino acid sequence sharing an identity of 90% or more with the amino acid sequence consisting of SEQ ID NO: 7 and having the activity of increasing the proportion of arachidonic acid in the compositional ratio of fatty acids in a host transformed with a recombinant vector containing a nucleic acid encoding the amino acid sequence as compared with the proportion in the compositional ratio of fatty acids in a host that has not been transformed with the vector.

7. The protein of claim 5, which belongs to the membrane-bound O-acyltransferase family.

8. An isolated protein consisting of the amino acid sequence shown in SEQ ID NO: 7.

9. An isolated cell transformed with the recombinant vector of claim 1.

10. A fatty acid composition obtained by culturing the transformed cell of claim 9 wherein the proportion of arachidonic acid in the compositional ratio of fatty acids in said fatty acid composition is higher than the proportion of arachidonic acid in the fatty acid composition obtained by culturing a non-transformed host.

11. A method for preparing a fatty acid composition, comprising collecting a fatty acid composition obtained by culturing the transformed cell of claim 9 wherein the proportion of arachidonic acid in the compositional ratio of fatty acids in said fatty acid composition is higher than the proportion of arachidonic acid in the fatty acid composition obtained by culturing a non-transformed host, from cultures of the transformed cell of claim 9.

12. A food product comprising the fatty acid composition of claim 10.

13. A method for using a recombinant vector of claim 1 to increase the proportion of arachidonic acid in the compositional ratio of fatty acids in an isolated host cell transformed with the vector as compared with the proportion in the compositional ratio of fatty acids in an isolated host cell that has not been transformed with the vector, the method comprising:
   transforming the isolated host cell with the vector; and
   allowing the transformed host cell to produce arachidonic acid.

14. A cDNA or recombinant vector comprising a nucleic acid of any one of (a)-(e) below:
   (a) a nucleic acid that comprises a nucleotide sequence encoding a protein consisting of an amino acid sequence with deletion, substitution or addition of one to 50 amino acids in the amino acid sequence shown in SEQ ID NO: 7, and involved in the conversion from 18:3(n-6)-PL to 18:3(n-6)-CoA or conversion from DGLA-CoA to DGLA-PL;
   (b) a nucleic acid that hybridizes under hybridization conditions of 0.1×SSC-1×SSC at 60° C.-65° C. and washing conditions of 0.2×SSC-2×SSC at 50° C.-68° C. to a nucleic acid consisting of a full length complement to the nucleotide sequence consisting of SEQ ID NO: 6 and that comprises a nucleotide sequence encoding a protein involved in the conversion from 18:3(n-6)-PL to 18:3(n-6)-CoA and/or or conversion from DGLA-CoA to DGLA-PL;
   (c) a nucleic acid that comprises a nucleotide sequence sharing an identity of 90% or more with the nucleotide sequence consisting of SEQ ID NO: 6 and encoding a protein involved in the conversion from 18:3(n-6)-PL to 18:3(n-6)-CoA or conversion from DGLA-CoA to DGLA-PL;
   (d) a nucleic acid that comprises a nucleotide sequence encoding a protein consisting of an amino acid sequence sharing an identity of 90% or more with the amino acid sequence consisting of SEQ ID NO: 7 and involved in the conversion from 18:3(n-6)-PL to 18:3(n-6)-CoA or conversion from DGLA-CoA to DGLA-PL; and
   (e) a nucleic acid that hybridizes under hybridization conditions of 0.1×SSC-1×SSC at 60° C.-65° C. and washing conditions of 0.2×SSC-2×SSC at 50° C.-68° C. to a nucleic acid consisting of a nucleotide sequence complementary full length complement to a nucleotide sequence encoding a protein consisting of the amino acid sequence shown in SEQ ID NO: 7 and that comprises a nucleotide sequence encoding a protein involved in the conversion from 18:3(n-6)-PL to 18:3(n-6)-CoA or conversion from DGLA-CoA to DGLA-PL.

15. An isolated protein of (a) or (b) below:
   (a) a protein consisting of an amino acid sequence with deletion, substitution or addition of one to 50 amino acids in the amino acid sequence of SEQ ID NO: 7, and involved in the conversion from 18:3(n-6)-PL to 18:3(n-6)-CoA or conversion from DGLA-CoA to DGLA-PL; or
   (b) a protein consisting of an amino acid sequence sharing an identity of 90% or more with the amino acid sequence consisting of SEQ ID NO: 7 and involved in the conversion from 18:3(n-6)-PL to 18:3(n-6)-CoA or conversion from DGLA-CoA to DGLA-PL.

* * * * *

UNITED STATES PATENT AND TRADEMARK OFFICE
CERTIFICATE OF CORRECTION

PATENT NO.       : 8,790,906 B2  
APPLICATION NO.  : 13/255390  
DATED            : July 29, 2014  
INVENTOR(S)      : M. Ochiai Page 1 of 1

It is certified that error appears in the above-identified patent and that said Letters Patent is hereby corrected as shown below:

In the Claims

At column 86, line 4 (claim 14) please delete "and/or."

At column 86, lines 21 and 22 (claim 14) please delete "nucleotide sequence complementary."

Signed and Sealed this  
Fourteenth Day of April, 2015

Michelle K. Lee  
*Director of the United States Patent and Trademark Office*

```
SEQUENCE LISTING

<160> NUMBER OF SEQ ID NOS: 45

<210> SEQ ID NO 1
<211> LENGTH: 1530
<212> TYPE: DNA
<213> ORGANISM: Mortierella alpina
<220> FEATURE:
<221> NAME/KEY: CDS
<222> LOCATION: (1)..(1530)

<400> SEQUENCE: 1 atg cta aac tca ttc ttc ggg acg ctc tcg gag gct gtc tcc ttc cca      48
Met Leu Asn Ser Phe Phe Gly Thr Leu Ser Glu Ala Val Ser Phe Pro
1               5                   10                  15 gag gat cag ctt cgt tgc ctc tcg gct ctg tta ctc tcc tac cct ctg      96
Glu Asp Gln Leu Arg Cys Leu Ser Ala Leu Leu Leu Ser Tyr Pro Leu
            20                  25                  30 gca ctt gct ttt cgc cta ctg ccc aac aac ccc aac ctt aaa cat act     144
Ala Leu Ala Phe Arg Leu Leu Pro Asn Asn Pro Asn Leu Lys His Thr
        35                  40                  45 gtc tct gtc ctg act tcc ttc ttc ctg atc gtg gtt att gtg gat gat     192
Val Ser Val Leu Thr Ser Phe Phe Leu Ile Val Val Ile Val Asp Asp
    50                  55                  60 ctc gtc gga ttg atg cat ctt ctg gga tcc agc atc gct gtc tgg agg     240
Leu Val Gly Leu Met His Leu Leu Gly Ser Ser Ile Ala Val Trp Arg
65                  70                  75                  80 ata atg ggt gcc gtt caa ggc aaa tgg ggg cca cgg cta gtt ttt att     288
Ile Met Gly Ala Val Gln Gly Lys Trp Gly Pro Arg Leu Val Phe Ile
                85                  90                  95 ggc gtt atg ctc cat atg agc gtc agt cat ctg ctt cgt cag ttc cac     336
Gly Val Met Leu His Met Ser Val Ser His Leu Leu Arg Gln Phe His
            100                 105                 110 gac tat aga gga tac aag ctg gat cac acc ggt cct caa atg att ctc     384
Asp Tyr Arg Gly Tyr Lys Leu Asp His Thr Gly Pro Gln Met Ile Leu
        115                 120                 125
```

```
acc atg aaa ctc acc tct tgg gcc ttc aat gtc tat gat ggc cgc cgt      432
Thr Met Lys Leu Thr Ser Trp Ala Phe Asn Val Tyr Asp Gly Arg Arg
        130                 135                 140 aac cca aag gaa ctc agc aga tat cag caa gac cac gcc gtc cta tcg      480
Asn Pro Lys Glu Leu Ser Arg Tyr Gln Gln Asp His Ala Val Leu Ser
145                 150                 155                 160 ttc cct tcc ctt ctt cac tac ctc agc tat gtc ttc ttc ttc ccc tcc      528
Phe Pro Ser Leu Leu His Tyr Leu Ser Tyr Val Phe Phe Phe Pro Ser
                    165                 170                 175 gtt ctc gtt ggt ccc tca ttc gaa tat atg gat tat atc cgc ttc att      576
Val Leu Val Gly Pro Ser Phe Glu Tyr Met Asp Tyr Ile Arg Phe Ile
            180                 185                 190 gag ctc act cag ttc cgg gac ccc aag act gga aag atc cac tgg ccc      624
Glu Leu Thr Gln Phe Arg Asp Pro Lys Thr Gly Lys Ile His Trp Pro
        195                 200                 205 gca ggt cgt gtc cga tct tcc atg agg act ttc ttt ttt gct atg att      672
Ala Gly Arg Val Arg Ser Ser Met Arg Thr Phe Phe Phe Ala Met Ile
210                 215                 220 gcc ttg gcc tgt ctg gcg gtt gtc ggg ccc aaa ctc gat gtt ctt tgg      720
Ala Leu Ala Cys Leu Ala Val Val Gly Pro Lys Leu Asp Val Leu Trp
225                 230                 235                 240 acg atg gag ccg gct tgg aaa gct ctg cca tgg atc ttg cgc ttt ggt      768
Thr Met Glu Pro Ala Trp Lys Ala Leu Pro Trp Ile Leu Arg Phe Gly
                245                 250                 255 tat gtg caa ctg gcc gcc ttt gcg gct cgt ttc aag tac tat gcg gtg      816
Tyr Val Gln Leu Ala Ala Phe Ala Ala Arg Phe Lys Tyr Tyr Ala Val
            260                 265                 270 tgg aag ctg gcc gag ggc gcc tgt gtt atg gct gga ttc gga tac aac      864
Trp Lys Leu Ala Glu Gly Ala Cys Val Met Ala Gly Phe Gly Tyr Asn
        275                 280                 285 gga cag gat ccc aag acg ggc gaa gct cgg tgg gat gcg acc tcc aac      912
Gly Gln Asp Pro Lys Thr Gly Glu Ala Arg Trp Asp Ala Thr Ser Asn
290                 295                 300 att aac gtt tgg gcc tac gag act ggc cag agc atc aaa act ttg gct      960
Ile Asn Val Trp Ala Tyr Glu Thr Gly Gln Ser Ile Lys Thr Leu Ala
305                 310                 315                 320 gat aac tgg aat atg ggc acc aac aag tgg tta aag cac tcc gtg tac     1008
Asp Asn Trp Asn Met Gly Thr Asn Lys Trp Leu Lys His Ser Val Tyr
                325                 330                 335 ttt aga gtc gtt gct ccc ggg gcg aag cct ggt ttc ttg gag acg ttt     1056
Phe Arg Val Val Ala Pro Gly Ala Lys Pro Gly Phe Leu Glu Thr Phe
            340                 345                 350 gcg acg ttt ggt gtg agc gcg ctg tgg cac gga ttc tac ccc gga tat     1104
Ala Thr Phe Gly Val Ser Ala Leu Trp His Gly Phe Tyr Pro Gly Tyr
        355                 360                 365 tac ctg atg ttt gct tct gcg gcc atg gct ctt aca gcg ggc aaa ttg     1152
Tyr Leu Met Phe Ala Ser Ala Ala Met Ala Leu Thr Ala Gly Lys Leu
370                 375                 380 ttg agg act cat ttg cgg ccg agg ttt gtg tca gcc tcg aca gga aag     1200
Leu Arg Thr His Leu Arg Pro Arg Phe Val Ser Ala Ser Thr Gly Lys
385                 390                 395                 400 acg cct ctt ctg tac aat atg ctg ggc atg gtc ttg acc cag gcg acg     1248
Thr Pro Leu Leu Tyr Asn Met Leu Gly Met Val Leu Thr Gln Ala Thr
                405                 410                 415 atc aac aca ctg tcc atg tcg ttc ttg ctg cta aca ttc aag gac agc     1296
Ile Asn Thr Leu Ser Met Ser Phe Leu Leu Leu Thr Phe Lys Asp Ser
            420                 425                 430 att gag gtt tgg aag aac ctc tac ttt gtc gtc cac ttg ggt atc atc     1344
Ile Glu Val Trp Lys Asn Leu Tyr Phe Val Val His Leu Gly Ile Ile
        435                 440                 445
```

```
gcc atc acg gtt ctg gtt ccc gtc tta ttc cca gtg aag cga aag ccc       1392
Ala Ile Thr Val Leu Val Pro Val Leu Phe Pro Val Lys Arg Lys Pro
    450                 455                 460 aag aaa gag cag cag cag ccc gag gtc gag aag gtc aag gaa ctc atg       1440
Lys Lys Glu Gln Gln Gln Pro Glu Val Glu Lys Val Lys Glu Leu Met
465                 470                 475                 480 cat gat gtt gca gag gag gtt gcc acc gtc tct gtg agt gct gcc agc       1488
His Asp Val Ala Glu Glu Val Ala Thr Val Ser Val Ser Ala Ala Ser
                485                 490                 495 gag ctc ctt gac acc tct gct gca gtt aaa atc aag acg ctg               1530
Glu Leu Leu Asp Thr Ser Ala Ala Val Lys Ile Lys Thr Leu
500                 505                 510
```

<210> SEQ ID NO 2
<211> LENGTH: 510
<212> TYPE: PRT
<213> ORGANISM: Mortierella alpina

<400> SEQUENCE: 2

```
Met Leu Asn Ser Phe Phe Gly Thr Leu Ser Glu Ala Val Ser Phe Pro
1               5                   10                  15

Glu Asp Gln Leu Arg Cys Leu Ser Ala Leu Leu Ser Tyr Pro Leu
            20                  25                  30

Ala Leu Ala Phe Arg Leu Leu Pro Asn Asn Pro Asn Leu Lys His Thr
        35                  40                  45

Val Ser Val Leu Thr Ser Phe Phe Leu Ile Val Val Ile Val Asp Asp
    50                  55                  60

Leu Val Gly Leu Met His Leu Leu Gly Ser Ser Ile Ala Val Trp Arg
65                  70                  75                  80

Ile Met Gly Ala Val Gln Gly Lys Trp Gly Pro Arg Leu Val Phe Ile
                85                  90                  95

Gly Val Met Leu His Met Ser Val Ser His Leu Leu Arg Gln Phe His
            100                 105                 110

Asp Tyr Arg Gly Tyr Lys Leu Asp His Thr Gly Pro Gln Met Ile Leu
        115                 120                 125

Thr Met Lys Leu Thr Ser Trp Ala Phe Asn Val Tyr Asp Gly Arg Arg
    130                 135                 140

Asn Pro Lys Glu Leu Ser Arg Tyr Gln Gln Asp His Ala Val Leu Ser
145                 150                 155                 160

Phe Pro Ser Leu Leu His Tyr Leu Ser Tyr Val Phe Phe Pro Ser
                165                 170                 175

Val Leu Val Gly Pro Ser Phe Glu Tyr Met Asp Tyr Ile Arg Phe Ile
            180                 185                 190

Glu Leu Thr Gln Phe Arg Asp Pro Lys Thr Gly Lys Ile His Trp Pro
        195                 200                 205

Ala Gly Arg Val Arg Ser Ser Met Arg Thr Phe Phe Ala Met Ile
    210                 215                 220

Ala Leu Ala Cys Leu Ala Val Val Gly Pro Lys Leu Asp Val Leu Trp
225                 230                 235                 240

Thr Met Glu Pro Ala Trp Lys Ala Leu Pro Trp Ile Leu Arg Phe Gly
                245                 250                 255

Tyr Val Gln Leu Ala Ala Phe Ala Ala Arg Phe Lys Tyr Tyr Ala Val
            260                 265                 270

Trp Lys Leu Ala Glu Gly Ala Cys Val Met Ala Gly Phe Gly Tyr Asn
        275                 280                 285
```

```
Gly Gln Asp Pro Lys Thr Gly Glu Ala Arg Trp Asp Ala Thr Ser Asn
    290                 295                 300

Ile Asn Val Trp Ala Tyr Glu Thr Gly Gln Ser Ile Lys Thr Leu Ala
305                 310                 315                 320

Asp Asn Trp Asn Met Gly Thr Asn Lys Trp Leu Lys His Ser Val Tyr
                325                 330                 335

Phe Arg Val Val Ala Pro Gly Ala Lys Pro Gly Phe Leu Glu Thr Phe
            340                 345                 350

Ala Thr Phe Gly Val Ser Ala Leu Trp His Gly Phe Tyr Pro Gly Tyr
        355                 360                 365

Tyr Leu Met Phe Ala Ser Ala Ala Met Ala Leu Thr Ala Gly Lys Leu
    370                 375                 380

Leu Arg Thr His Leu Arg Pro Arg Phe Val Ser Ala Ser Thr Gly Lys
385                 390                 395                 400

Thr Pro Leu Leu Tyr Asn Met Leu Gly Met Val Leu Thr Gln Ala Thr
                405                 410                 415

Ile Asn Thr Leu Ser Met Ser Phe Leu Leu Thr Phe Lys Asp Ser
            420                 425                 430

Ile Glu Val Trp Lys Asn Leu Tyr Phe Val Val His Leu Gly Ile Ile
        435                 440                 445

Ala Ile Thr Val Leu Val Pro Val Leu Phe Pro Val Lys Arg Lys Pro
    450                 455                 460

Lys Lys Glu Gln Gln Gln Pro Glu Val Glu Lys Val Lys Glu Leu Met
465                 470                 475                 480

His Asp Val Ala Glu Glu Val Ala Thr Val Ser Val Ser Ala Ala Ser
                485                 490                 495

Glu Leu Leu Asp Thr Ser Ala Ala Val Lys Ile Lys Thr Leu
            500                 505                 510

<210> SEQ ID NO 3
<211> LENGTH: 1533
<212> TYPE: DNA
<213> ORGANISM: Mortierella alpina

<400> SEQUENCE: 3 atgctaaaact cattcttcgg gacgctctcg gaggctgtct ccttcccaga ggatcagctt    60
cgttgcctct cggctctgtt actctcctac cctctggcac ttgcttttcg cctactgccc   120 aacaaccccca accttaaaca tactgtctct gtcctgactt ccttcttcct gatcgtggtt   180
attgtggatg atctcgtcgg attgatgcat cttctgggat ccagcatcgc tgtctggagg   240
ataatgggtg ccgttcaagg caaatggggg ccacggctag ttttttattgg cgttatgctc   300 catatgagcg tcagtcatct gcttcgtcag ttccacgact atagaggata caagctggat   360
cacaccggtc ctcaaatgat tctcaccatg aaactcacct cttgggcctt caatgtctat   420
gatggccgcc gtaacccaaa ggaactcagc agatatcagc aagaccacgc cgtcctatcg   480 ttccccttccc ttcttcacta cctcagctat gtcttcttct cccctccgt tctcgttggt   540 ccctcattcg aatatatgga ttatatccgc ttcattgagc tcactcagtt ccgggacccc   600
aagactggaa agatccactg gcccgcaggt cgtgtccgat cttccatgag gactttcttt   660
tttgctatga ttgccttggc ctgtctggcg gttgtcgggc ccaaactcga tgttctttgg   720
acgatggagc cggcttggaa agctctgcca tggatcttgc gctttggtta tgtgcaactg   780
gccgcctttg cggctcgttt caagtactat gcggtgtgga agctggccga gggcgcctgt   840
gttatggctg gattcggata caacggacag gatcccaaga cgggcgaagc tcggtgggat   900
```

-continued

```
gcgacctcca acattaacgt ttgggcctac gagactggcc agagcatcaa aactttggct      960
gataactgga atatgggcac caacaagtgg ttaaagcact ccgtgtactt tagagtcgtt     1020
gctcccgggg cgaagcctgg tttcttggag acgtttgcga cgtttggtgt gagcgcgctg     1080
tggcacggat tctaccccgg atattacctg atgtttgctt ctgcggccat ggctcttaca     1140
gcgggcaaat tgttgaggac tcatttgcgg ccgaggtttg tgtcagcctc gacaggaaag     1200
acgcctcttc tgtacaatat gctgggcatg gtcttgaccc aggcgacgat caacacactg     1260
tccatgtcgt tcttgctgct aacattcaag gacagcattg aggtttggaa gaacctctac     1320
tttgtcgtcc acttgggtat catcgccatc acggttctgg ttcccgtctt attcccagtg     1380
aagcgaaagc ccaagaaaga gcagcagcag cccgaggtcg agaaggtcaa ggaactcatg     1440
catgatgttg cagaggaggt tgccaccgtc tctgtgagtg ctgccagcga gctccttgac     1500
acctctgctg cagttaaaat caagacgctg taa                                  1533
```

<210> SEQ ID NO 4
<211> LENGTH: 1834
<212> TYPE: DNA
<213> ORGANISM: Mortierella alpina
<220> FEATURE:
<221> NAME/KEY: CDS
<222> LOCATION: (161)..(1690)

<400> SEQUENCE: 4

```
cctccctcct cctcgtagac gaactccttc ccgctgacgg agaagtcttg agctgagttc       60
atcctcaaag agatcaaatt ttttcccctc cctctcctcg tcgtcttcac gtctcttctt      120
ctttctatac cacagcacac tcgccatagc acaactcacc atg cta aac tca ttc        175
                                              Met Leu Asn Ser Phe
                                              1               5 ttc ggg acg ctc tcg gag gct gtc tcc ttc cca gag gat cag ctt cgt        223
Phe Gly Thr Leu Ser Glu Ala Val Ser Phe Pro Glu Asp Gln Leu Arg
                10                  15                  20 tgc ctc tcg gct ctg tta ctc tcc tac cct ctg gca ctt gct ttt cgc        271
Cys Leu Ser Ala Leu Leu Leu Ser Tyr Pro Leu Ala Leu Ala Phe Arg
            25                  30                  35 cta ctg ccc aac aac ccc aac ctt aaa cat act gtc tct gtc ctg act        319
Leu Leu Pro Asn Asn Pro Asn Leu Lys His Thr Val Ser Val Leu Thr
        40                  45                  50 tcc ttc ttc ctg atc gtg gtt att gtg gat gat ctc gtc gga ttg atg        367
Ser Phe Phe Leu Ile Val Val Ile Val Asp Asp Leu Val Gly Leu Met
    55                  60                  65 cat ctt ctg gga tcc agc atc gct gtc tgg agg ata atg ggt gcc gtt        415
His Leu Leu Gly Ser Ser Ile Ala Val Trp Arg Ile Met Gly Ala Val
70                  75                  80                  85 caa ggc aaa tgg ggg cca cgg cta gtt ttt att ggc gtt atg ctc cat        463
Gln Gly Lys Trp Gly Pro Arg Leu Val Phe Ile Gly Val Met Leu His
                90                  95                 100 atg agc gtc agt cat ctg ctt cgt cag ttc cac gac tat aga gga tac        511
Met Ser Val Ser His Leu Leu Arg Gln Phe His Asp Tyr Arg Gly Tyr
            105                 110                 115 aag ctg gat cac acc ggt cct caa atg att ctc acc atg aaa ctc acc        559
Lys Leu Asp His Thr Gly Pro Gln Met Ile Leu Thr Met Lys Leu Thr
        120                 125                 130 tct tgg gcc ttc aat gtc tat gat ggc cgc cgt aac cca aag gaa ctc        607
Ser Trp Ala Phe Asn Val Tyr Asp Gly Arg Arg Asn Pro Lys Glu Leu
    135                 140                 145 agc aga tat cag caa gac cac gcc gtc cta tcg ttc cct tcc ctt ctt        655
Ser Arg Tyr Gln Gln Asp His Ala Val Leu Ser Phe Pro Ser Leu Leu
```

```
Ser Arg Tyr Gln Gln Asp His Ala Val Leu Ser Phe Pro Ser Leu Leu
150                 155                 160                 165 cac tac ctc agc tat gtc ttc ttc ttc ccc tcc gtt ctc gtt ggt ccc        703
His Tyr Leu Ser Tyr Val Phe Phe Phe Pro Ser Val Leu Val Gly Pro
                170                 175                 180 tca ttc gaa tat atg gat tat atc cgc ttc att gag ctc act cag ttc        751
Ser Phe Glu Tyr Met Asp Tyr Ile Arg Phe Ile Glu Leu Thr Gln Phe
            185                 190                 195 cgg gac ccc aag act gga aag atc cac tgg ccc gca ggt cgt gtc cga        799
Arg Asp Pro Lys Thr Gly Lys Ile His Trp Pro Ala Gly Arg Val Arg
        200                 205                 210 tct tcc atg agg act ttc ttt ttt gct atg att gcc ttg gcc tgt ctg        847
Ser Ser Met Arg Thr Phe Phe Phe Ala Met Ile Ala Leu Ala Cys Leu
    215                 220                 225 gcg gtt gtc ggg ccc aaa ctc gat gtt ctt tgg acg atg gag ccg gct        895
Ala Val Val Gly Pro Lys Leu Asp Val Leu Trp Thr Met Glu Pro Ala
230                 235                 240                 245 tgg aaa gct ctg cca tgg atc ttg cgc ttt ggt tat gtg caa ctg gcc        943
Trp Lys Ala Leu Pro Trp Ile Leu Arg Phe Gly Tyr Val Gln Leu Ala
                250                 255                 260 gcc ttt gcg gct cgt ttc aag tac tat gcg gtg tgg aag ctg gcc gag        991
Ala Phe Ala Ala Arg Phe Lys Tyr Tyr Ala Val Trp Lys Leu Ala Glu
            265                 270                 275 ggc gcc tgt gtt atg gct gga ttc gga tac aac gga cag gat ccc aag       1039
Gly Ala Cys Val Met Ala Gly Phe Gly Tyr Asn Gly Gln Asp Pro Lys
        280                 285                 290 acg ggc gaa gct cgg tgg gat gcg acc tcc aac att aac gtt tgg gcc       1087
Thr Gly Glu Ala Arg Trp Asp Ala Thr Ser Asn Ile Asn Val Trp Ala
    295                 300                 305 tac gag act ggc cag agc atc aaa act ttg gct gat aac tgg aat atg       1135
Tyr Glu Thr Gly Gln Ser Ile Lys Thr Leu Ala Asp Asn Trp Asn Met
310                 315                 320                 325 ggc acc aac aag tgg tta aag cac tcc gtg tac ttt aga gtc gtt gct       1183
Gly Thr Asn Lys Trp Leu Lys His Ser Val Tyr Phe Arg Val Val Ala
                330                 335                 340 ccc ggg gcg aag cct ggt ttc ttg gag acg ttt gcg acg ttt ggt gtg       1231
Pro Gly Ala Lys Pro Gly Phe Leu Glu Thr Phe Ala Thr Phe Gly Val
            345                 350                 355 agc gcg ctg tgg cac gga ttc tac ccc gga tat tac ctg atg ttt gct       1279
Ser Ala Leu Trp His Gly Phe Tyr Pro Gly Tyr Tyr Leu Met Phe Ala
        360                 365                 370 tct gcg gcc atg gct ctt aca gcg ggc aaa ttg ttg agg act cat ttg       1327
Ser Ala Ala Met Ala Leu Thr Ala Gly Lys Leu Leu Arg Thr His Leu
    375                 380                 385 cgg ccg agg ttt gtg tca gcc tcg aca gga aag acg cct ctt ctg tac       1375
Arg Pro Arg Phe Val Ser Ala Ser Thr Gly Lys Thr Pro Leu Leu Tyr
390                 395                 400                 405 aat atg ctg ggc atg gtc ttg acc cag gcg acg atc aac aca ctg tcc       1423
Asn Met Leu Gly Met Val Leu Thr Gln Ala Thr Ile Asn Thr Leu Ser
                410                 415                 420 atg tcg ttc ttg ctg cta aca ttc aag gac agc att gag gtt tgg aag       1471
Met Ser Phe Leu Leu Leu Thr Phe Lys Asp Ser Ile Glu Val Trp Lys
            425                 430                 435 aac ctc tac ttt gtc gtc cac ttg ggt atc atc gcc atc acg gtt ctg       1519
Asn Leu Tyr Phe Val Val His Leu Gly Ile Ile Ala Ile Thr Val Leu
        440                 445                 450 gtt ccc gtc tta ttc cca gtg aag cga aag ccc aag aaa gag cag cag       1567
Val Pro Val Leu Phe Pro Val Lys Arg Lys Pro Lys Lys Glu Gln Gln
    455                 460                 465
```

```
cag ccc gag gtc gag aag gtc aag gaa ctc atg cat gat gtt gca gag      1615
Gln Pro Glu Val Glu Lys Val Lys Glu Leu Met His Asp Val Ala Glu
470                 475                 480                 485 gag gtt gcc acc gtc tct gtg agt gct gcc agc gag ctc ctt gac acc      1663
Glu Val Ala Thr Val Ser Val Ser Ala Ala Ser Glu Leu Leu Asp Thr
            490                 495                 500 tct gct gca gtt aaa atc aag acg ctg taaatggatg ctttgcgacg            1710
Ser Ala Ala Val Lys Ile Lys Thr Leu
            505                 510 ttccctcttg accatagcga gcacgctatc attaccacat ctgtacacat acctctccac    1770
actccacgca caacttatgt gcataaagaa cagctttcca ctgtaaaaaa aaaaaaaaaa    1830
aaaa                                                                 1834

<210> SEQ ID NO 5
<211> LENGTH: 1759
<212> TYPE: DNA
<213> ORGANISM: Mortierella alpina

<400> SEQUENCE: 5
atgctaaact cattcttcgg gacgctctcg gaggctgtct ccttcccaga ggatcagctt      60
cgttgcctct cggctctgtt actctcctac cctctggcac ttgcttttcg cctactgccc     120
aacaacccca accttaaaca tactgtctct gtcctgactt ccttcttcct gatcgtggtt     180
attgtggatg atctcgtcgg attgatgcat cttctgggat ccagcatcgc tgtctggagg     240
ataatgggtg ccgttcaagg caaatggggg ccacggctag tttttattgg cgttatgctc     300
catatgagcg tcaggtaacg tttgccttgc aggcctttga accctgctg tgtagctagc      360 caaagtcctt cttgtcgccc ccacacccat gccctaactg agatcctgca cctcgctcta     420
tcattccttc actcctcata tcatcgtgat gcaattacag tcatctgctt cgtcagttcc     480
acgactatag aggatacaag ctggatcaca ccggtcctca atgattctc accatgaaac      540 tcacctcttg ggccttcaat gtctatgatg ccgccgtaa cccaaaggta ataatgacac      600
ccatcacgct aggaaaacgt ttattataca tttgaacgtc aaactcaccc tctcttctcg     660
gtcgcaggaa ctcagcagat atcagcaaga ccacgccgtc ctatcgttcc cttcccttct     720
tcactacctc agctatgtct tcttcttccc ctccgttctc gttggtccct cattcgaata     780
tatggattat atccgcttca ttgagctcac tcagttccgg gaccccaaga ctggaaagat     840
ccactggccc gcaggtcgtg tccgatcttc catgaggact ttcttttttg ctatgattgc     900 cttgcctgt ctggcggttg tcgggcccaa actcgatgtt ctttgacga tggagccggc       960 ttggaaagct ctgccatgga tcttgcgctt tggttatgtg caactggccg ccttgcggc     1020 tcgtttcaag tactatgcgg tgtggaagct ggccgagggc gcctgtgtta tggctggatt    1080
cggatacaac ggacaggatc ccaagacggg cgaagctcgg tgggatgcga cctccaacat    1140
taacgttggg gcctacgaga ctggccgagc atcaaaact ttggctgata actggaatat     1200
gggcaccaac aagtggttaa agcactccgt gtactttaga gtcgttgctc ccgggggcgaa   1260 gcctggtttc ttgagacgt ttgcgacgtt tggtgtgagc gcgctgtggc acggattcta     1320
ccccggatat tacctgatgt ttgcttctgc ggccatggct cttacagcgg caaattgtt     1380 gaggactcat ttgcggccga ggtttgtgtc agcctcgaca ggaaagacgc tcttctgta     1440 caatatgctg gcatggtct tgacccaggc gacgatcaac acactgtcca tgtcgttctt     1500
gctgctaaca ttcaaggaca gcattgaggt ttggaagaac ctctactttg tcgtccactt    1560
gggtatcatc gccatcacgg ttctggttcc cgtcttattc ccagtgaagc gaaagcccaa    1620
```

```
gaaagagcag cagcagcccg aggtcgagaa ggtcaaggaa ctcatgcatg atgttgcaga    1680
ggaggttgcc accgtctctg tgagtgctgc cagcgagctc cttgacacct ctgctgcagt    1740
taaaatcaag acgctgtaa                                                 1759

<210> SEQ ID NO 6
<211> LENGTH: 1719
<212> TYPE: DNA
<213> ORGANISM: Mortierella alpina
<220> FEATURE:
<221> NAME/KEY: CDS
<222> LOCATION: (1)..(1719)

<400> SEQUENCE: 6 atg gag gca ctc ttg cac cag gtt cat gac acc tac ctg ccc gct tgg     48
Met Glu Ala Leu Leu His Gln Val His Asp Thr Tyr Leu Pro Ala Trp
1               5                   10                  15 ttc gga ccc aaa ccc ccg gcg gct ttt ctc gac tat ggt ctg acc cag     96
Phe Gly Pro Lys Pro Pro Ala Ala Phe Leu Asp Tyr Gly Leu Thr Gln
            20                  25                  30 tcc cta agc gag gcc tcg ggc att ccc gaa ccc tcg ctg cgt cta ctc    144
Ser Leu Ser Glu Ala Ser Gly Ile Pro Glu Pro Ser Leu Arg Leu Leu
        35                  40                  45 atg acg atc ctg gcg ggt tac cca gtc tcg ttc att tac cga ctc atc    192
Met Thr Ile Leu Ala Gly Tyr Pro Val Ser Phe Ile Tyr Arg Leu Ile
    50                  55                  60 ttt ctg aac aag acg tcg agc att gtg ggc gaa tcg gca cgg aac gcg    240
Phe Leu Asn Lys Thr Ser Ser Ile Val Gly Glu Ser Ala Arg Asn Ala
65                  70                  75                  80 ttc ttc ttg tcc acg ggc ttg ctc ctc tct tac tac ttc aac tcg ttt    288
Phe Phe Leu Ser Thr Gly Leu Leu Leu Ser Tyr Tyr Phe Asn Ser Phe
                85                  90                  95 gat atc atc cac cct ctg acc acc tgt atc ggc acc tgg ctc atc tgc    336
Asp Ile Ile His Pro Leu Thr Thr Cys Ile Gly Thr Trp Leu Ile Cys
            100                 105                 110 aag gtc gta ggt gcg atc gct ccc aag aat cgg tcg ctg gcc tcg acg    384
Lys Val Val Gly Ala Ile Ala Pro Lys Asn Arg Ser Leu Ala Ser Thr
        115                 120                 125 gtc gcg ttc ctc ttc aac ttt gga tat ctg ctc acg tcc tac aag tac    432
Val Ala Phe Leu Phe Asn Phe Gly Tyr Leu Leu Thr Ser Tyr Lys Tyr
    130                 135                 140 gcg gcc acg gag gat tac gac atc tgc tac acg atg cag caa tgt gtc    480
Ala Ala Thr Glu Asp Tyr Asp Ile Cys Tyr Thr Met Gln Gln Cys Val
145                 150                 155                 160 cag tgt ctt cgc atg atc gga tat ggt atg gac ttt atg gac gga cag    528
Gln Cys Leu Arg Met Ile Gly Tyr Gly Met Asp Phe Met Asp Gly Gln
                165                 170                 175 ccc aaa ccc gca agc aag aaa cat ctg gcc gct gcc gcg agt gcc gag    576
Pro Lys Pro Ala Ser Lys Lys His Leu Ala Ala Ala Ala Ser Ala Glu
            180                 185                 190 act ttg gcc aca ttg gtc gag gag gtc aag gcc aac ccc aac aag gcc    624
Thr Leu Ala Thr Leu Val Glu Glu Val Lys Ala Asn Pro Asn Lys Ala
        195                 200                 205 gat cag ggc atc gac cac gtc gtg gtc gct ccc agc ccc gct gcc gtc    672
Asp Gln Gly Ile Asp His Val Val Val Ala Pro Ser Pro Ala Ala Val
    210                 215                 220 acc cct gtc agg gaa aag act cca att tcg ttc gga cgg gac att gct    720
Thr Pro Val Arg Glu Lys Thr Pro Ile Ser Phe Gly Arg Asp Ile Ala
225                 230                 235                 240 ctc cct cag ttg ccc acg ttg gcc gag acg atc ggc tat gcc ttc ttc    768
```

```
            Leu Pro Gln Leu Pro Thr Leu Ala Glu Thr Ile Gly Tyr Ala Phe Phe
                            245                 250                 255 ccg ttc gcg ttc ttg gtc ggc ccc cag ttt tcg ttc tcg ctc tac aaa             816
Pro Phe Ala Phe Leu Val Gly Pro Gln Phe Ser Phe Ser Leu Tyr Lys
                260                 265                 270 aag ttc att tcg atg gag ctc ttc aat gtg ccg gtg cct gcc tcg gcc             864
Lys Phe Ile Ser Met Glu Leu Phe Asn Val Pro Val Pro Ala Ser Ala
                275                 280                 285 gga cgc gat gag gcc aag gcc gct gct gct gcg acc gcg aac gga atc             912
Gly Arg Asp Glu Ala Lys Ala Ala Ala Ala Ala Thr Ala Asn Gly Ile
        290                 295                 300 ccc cag ggt tct ctg cgc tac gcg ttg cgc tgt ttc tcc ctt ggt gtg             960
Pro Gln Gly Ser Leu Arg Tyr Ala Leu Arg Cys Phe Ser Leu Gly Val
305                 310                 315                 320 ttc tat ctg gga ctg ggt cag gtt ttg gga gga tac ttc ccc acg gcc            1008
Phe Tyr Leu Gly Leu Gly Gln Val Leu Gly Gly Tyr Phe Pro Thr Ala
                325                 330                 335 gca ttg ttg ggt aaa gcc ttc ctg gaa cgc tcg tac ctg gag aag gtc            1056
Ala Leu Leu Gly Lys Ala Phe Leu Glu Arg Ser Tyr Leu Glu Lys Val
                340                 345                 350 ttt atc ttt tgg tgg act gga aag act gtc ttg aac aag tac ctt ggc            1104
Phe Ile Phe Trp Trp Thr Gly Lys Thr Val Leu Asn Lys Tyr Leu Gly
                355                 360                 365 att tgg acc atc gcc gag gga ccc tgc gtc ctc tcg ggc atc acc ttc            1152
Ile Trp Thr Ile Ala Glu Gly Pro Cys Val Leu Ser Gly Ile Thr Phe
370                 375                 380 aac ggt tat gac gcc cag gga cgg ccc gag tgg gac gga ctc cgg aac            1200
Asn Gly Tyr Asp Ala Gln Gly Arg Pro Glu Trp Asp Gly Leu Arg Asn
385                 390                 395                 400 gtg aac cct ctc aac tat gag ttt gcg acg tcc ctg acc cag atc gtg            1248
Val Asn Pro Leu Asn Tyr Glu Phe Ala Thr Ser Leu Thr Gln Ile Val
                405                 410                 415 acc tcg ttc aac atg aac aca aac ttc tgg gcc aag ctt tac atc ttc            1296
Thr Ser Phe Asn Met Asn Thr Asn Phe Trp Ala Lys Leu Tyr Ile Phe
                420                 425                 430 aag cgt ctg cgt ttc ctc ggt aac aag aac ctg tca gcc ctc ggc gtc            1344
Lys Arg Leu Arg Phe Leu Gly Asn Lys Asn Leu Ser Ala Leu Gly Val
                435                 440                 445 ttg ctc ttc ttg gcg atc tgg cac gga acc cat atc ggt tac ttt ttc            1392
Leu Leu Phe Leu Ala Ile Trp His Gly Thr His Ile Gly Tyr Phe Phe
450                 455                 460 tgc ttt ggc ctc gag ttc atg gac atg gag acc gag cgt cgg ttg tcg            1440
Cys Phe Gly Leu Glu Phe Met Asp Met Glu Thr Glu Arg Arg Leu Ser
465                 470                 475                 480 gtt agg ttt ggt cgt ccc att aat gcg ttc att gct cgc cag caa ggt            1488
Val Arg Phe Gly Arg Pro Ile Asn Ala Phe Ile Ala Arg Gln Gln Gly
                485                 490                 495 gtg agc cat gcg atc ctc aag gcc gtt tgg ggt gtc atc acc tgg ctc            1536
Val Ser His Ala Ile Leu Lys Ala Val Trp Gly Val Ile Thr Trp Leu
                500                 505                 510 ttg acg acg agt gcc ctg tac ttt gcg gcc gtg cct ttt gat ctg ttg            1584
Leu Thr Thr Ser Ala Leu Tyr Phe Ala Ala Val Pro Phe Asp Leu Leu
                515                 520                 525 cag atg gac aag tcg ttg gcg gcg atc cgg gcg atc aac tac ctc ggc            1632
Gln Met Asp Lys Ser Leu Ala Ala Ile Arg Ala Ile Asn Tyr Leu Gly
                530                 535                 540 atc tat gtc atg gcg gga ctt ttg ttc ctg gac att gct ctg tcg gtg            1680
Ile Tyr Val Met Ala Gly Leu Leu Phe Leu Asp Ile Ala Leu Ser Val
545                 550                 555                 560
```

```
                gtc atg ccc aag aag cga tcc aag tct gtc aag act gag              1719
                Val Met Pro Lys Lys Arg Ser Lys Ser Val Lys Thr Glu
                            565                 570
```

<210> SEQ ID NO 7
<211> LENGTH: 573
<212> TYPE: PRT
<213> ORGANISM: Mortierella alpina

<400> SEQUENCE: 7

```
Met Glu Ala Leu Leu His Gln Val His Asp Thr Tyr Leu Pro Ala Trp
1               5                   10                  15

Phe Gly Pro Lys Pro Pro Ala Ala Phe Leu Asp Tyr Gly Leu Thr Gln
            20                  25                  30

Ser Leu Ser Glu Ala Ser Gly Ile Pro Glu Pro Ser Leu Arg Leu Leu
        35                  40                  45

Met Thr Ile Leu Ala Gly Tyr Pro Val Ser Phe Ile Tyr Arg Leu Ile
    50                  55                  60

Phe Leu Asn Lys Thr Ser Ser Ile Val Gly Glu Ser Ala Arg Asn Ala
65                  70                  75                  80

Phe Phe Leu Ser Thr Gly Leu Leu Ser Tyr Tyr Phe Asn Ser Phe
                85                  90                  95

Asp Ile Ile His Pro Leu Thr Thr Cys Ile Gly Thr Trp Leu Ile Cys
                100                 105                 110

Lys Val Val Gly Ala Ile Ala Pro Lys Asn Arg Ser Leu Ala Ser Thr
            115                 120                 125

Val Ala Phe Leu Phe Asn Phe Gly Tyr Leu Leu Thr Ser Tyr Lys Tyr
        130                 135                 140

Ala Ala Thr Glu Asp Tyr Asp Ile Cys Tyr Thr Met Gln Gln Cys Val
145                 150                 155                 160

Gln Cys Leu Arg Met Ile Gly Tyr Gly Met Asp Phe Met Asp Gly Gln
                165                 170                 175

Pro Lys Pro Ala Ser Lys His Leu Ala Ala Ala Ser Ala Glu
            180                 185                 190

Thr Leu Ala Thr Leu Val Glu Glu Val Lys Ala Asn Pro Asn Lys Ala
        195                 200                 205

Asp Gln Gly Ile Asp His Val Val Ala Pro Ser Pro Ala Ala Val
    210                 215                 220

Thr Pro Val Arg Glu Lys Thr Pro Ile Ser Phe Gly Arg Asp Ile Ala
225                 230                 235                 240

Leu Pro Gln Leu Pro Thr Leu Ala Glu Thr Ile Gly Tyr Ala Phe Phe
                245                 250                 255

Pro Phe Ala Phe Leu Val Gly Pro Gln Phe Ser Phe Ser Leu Tyr Lys
            260                 265                 270

Lys Phe Ile Ser Met Glu Leu Phe Asn Val Pro Val Pro Ala Ser Ala
        275                 280                 285

Gly Arg Asp Glu Ala Lys Ala Ala Ala Ala Thr Ala Asn Gly Ile
    290                 295                 300

Pro Gln Gly Ser Leu Arg Tyr Ala Leu Arg Cys Phe Ser Leu Gly Val
305                 310                 315                 320

Phe Tyr Leu Gly Leu Gly Gln Val Leu Gly Tyr Phe Pro Thr Ala
                325                 330                 335

Ala Leu Leu Gly Lys Ala Phe Leu Glu Arg Ser Tyr Leu Glu Lys Val
            340                 345                 350

Phe Ile Phe Trp Trp Thr Gly Lys Thr Val Leu Asn Lys Tyr Leu Gly
```

```
                355                 360                 365
Ile Trp Thr Ile Ala Glu Gly Pro Cys Val Leu Ser Gly Ile Thr Phe
        370                 375                 380
Asn Gly Tyr Asp Ala Gln Gly Arg Pro Glu Trp Asp Gly Leu Arg Asn
385                 390                 395                 400
Val Asn Pro Leu Asn Tyr Glu Phe Ala Thr Ser Leu Thr Gln Ile Val
                405                 410                 415
Thr Ser Phe Asn Met Asn Thr Asn Phe Trp Ala Lys Leu Tyr Ile Phe
                420                 425                 430
Lys Arg Leu Arg Phe Leu Gly Asn Lys Asn Leu Ser Ala Leu Gly Val
            435                 440                 445
Leu Leu Phe Leu Ala Ile Trp His Gly Thr His Ile Gly Tyr Phe Phe
        450                 455                 460
Cys Phe Gly Leu Glu Phe Met Asp Met Glu Thr Glu Arg Arg Leu Ser
465                 470                 475                 480
Val Arg Phe Gly Arg Pro Ile Asn Ala Phe Ile Ala Arg Gln Gln Gly
                485                 490                 495
Val Ser His Ala Ile Leu Lys Ala Val Trp Gly Val Ile Thr Trp Leu
                500                 505                 510
Leu Thr Thr Ser Ala Leu Tyr Phe Ala Ala Val Pro Phe Asp Leu Leu
            515                 520                 525
Gln Met Asp Lys Ser Leu Ala Ala Ile Arg Ala Ile Asn Tyr Leu Gly
        530                 535                 540
Ile Tyr Val Met Ala Gly Leu Leu Phe Leu Asp Ile Ala Leu Ser Val
545                 550                 555                 560
Val Met Pro Lys Lys Arg Ser Lys Ser Val Lys Thr Glu
                565                 570

<210> SEQ ID NO 8
<211> LENGTH: 1722
<212> TYPE: DNA
<213> ORGANISM: Mortierella alpina

<400> SEQUENCE: 8
atggaggcac tcttgcacca ggttcatgac acctacctgc ccgcttggtt cggacccaaa      60 ccccccggcgg cttttctcga ctatggtctg acccagtccc taagcgaggc ctcgggcatt     120
cccgaaccct cgctgcgtct actcatgacg atcctggcgg gttacccagt ctcgttcatt     180
taccgactca tctttctgaa caagacgtcg agcattgtgg gcgaatcggc acggaacgcg     240
ttcttcttgt ccacgggctt gctcctctct tactacttca actcgtttga tatcatccac     300
cctctgacca cctgtatcgg cacctggctc atctgcaagg tcgtaggtgc gatcgctccc     360
aagaatcggt cgctggcctc gacggtcgcg ttcctcttca actttggata tctgctcacg     420
tcctacaagt acgcggccac ggaggattac gacatctgct acacgatgca gcaatgtgtc     480
cagtgtcttc gcatgatcgg atatggtatg gactttatgg acggacagcc caaacccgca     540
agcaagaaac atctggccgc tgccgcgagt gccgagactt tggccacatt ggtcgaggag     600
gtcaaggcca accccaacaa ggccgatcag ggcatcgacc acgtcgtggt cgctcccagc     660
cccgctgccg tcaccctgt cagggaaaag actccaattt cgttcggacg ggacattgct     720
ctccctcagt tgcccacgtt ggccgagacg atcggctatg ccttcttccc gttcgcgttc     780
ttggtcggcc cccagttttc gttctcgctc tacaaaaagt tcatttcgat ggagctcttc     840
aatgtgccgg tgcctgcctc ggccggacgc gatgaggcca aggccgctgc tgctgcgacc     900
```

-continued

```
gcgaacggaa tcccccaggg ttctctgcgc tacgcgttgc gctgtttctc ccttggtgtg    960
ttctatctgg gactgggtca ggttttggga ggatacttcc ccacggccgc attgttgggt   1020
aaagccttcc tggaacgctc gtacctggag aaggtcttta tcttttggtg gactggaaag   1080
actgtcttga acaagtacct tggcatttgg accatcgccg agggaccctg cgtcctctcg   1140
ggcatcacct tcaacggtta tgacgcccag ggacggcccg agtgggacgg actccggaac   1200
gtgaaccctc tcaactatga gtttgcgacg tccctgaccc agatcgtgac ctcgttcaac   1260
atgaacacaa acttctgggc caagctttac atcttcaagc gtctgcgttt cctcggtaac   1320
aagaacctgt cagccctcgg cgtcttgctc ttcttggcga tctggcacgg aacccatatc   1380
ggttactttt tctgctttgg cctcgagttc atggacatgg agaccgagcg tcggttgtcg   1440
gttaggtttg gtcgtcccat taatgcgttc attgctcgcc agcaaggtgt gagccatgcg   1500
atcctcaagg ccgtttgggg tgtcatcacc tggctcttga cgacgagtgc cctgtacttt   1560
gcggccgtgc cttttgatct gttgcagatg gacaagtcgt tggcggcgat ccgggcgatc   1620
aactacctcg gcatctatgt catggcggga cttttgttcc tggacattgc tctgtcggtg   1680
gtcatgccca gaagcgatc caagtctgtc aagactgagt aa                       1722
```

<210> SEQ ID NO 9
<211> LENGTH: 1901
<212> TYPE: DNA
<213> ORGANISM: Mortierella alpina
<220> FEATURE:
<221> NAME/KEY: CDS
<222> LOCATION: (38)..(1756)

<400> SEQUENCE: 9

```
ccctcccctg gcaaaaacag acagcgcacg agtaaag atg gag gca ctc ttg cac     55
                                        Met Glu Ala Leu Leu His
                                         1               5 cag gtt cat gac acc tac ctg ccc gct tgg ttc gga ccc aaa ccc ccg     103
Gln Val His Asp Thr Tyr Leu Pro Ala Trp Phe Gly Pro Lys Pro Pro
         10                  15                  20 gcg gct ttt ctc gac tat ggt ctg acc cag tcc cta agc gag gcc tcg     151
Ala Ala Phe Leu Asp Tyr Gly Leu Thr Gln Ser Leu Ser Glu Ala Ser
     25                  30                  35 ggc att ccc gaa ccc tcg ctg cgt cta ctc atg acg atc ctg gcg ggt     199
Gly Ile Pro Glu Pro Ser Leu Arg Leu Leu Met Thr Ile Leu Ala Gly
 40                  45                  50 tac cca gtc tcg ttc att tac cga ctc atc ttt ctg aac aag acg tcg     247
Tyr Pro Val Ser Phe Ile Tyr Arg Leu Ile Phe Leu Asn Lys Thr Ser
55                  60                  65                  70 agc att gtg ggc gaa tcg gca cgg aac gcg ttc ttg tcc acg ggc         295
Ser Ile Val Gly Glu Ser Ala Arg Asn Ala Phe Phe Leu Ser Thr Gly
                 75                  80                  85 ttg ctc ctc tct tac tac ttc aac tcg ttt gat atc atc cac cct ctg     343
Leu Leu Leu Ser Tyr Tyr Phe Asn Ser Phe Asp Ile Ile His Pro Leu
             90                  95                 100 acc acc tgt atc ggc acc tgg ctc atc tgc aag gtc gta ggt gcg atc     391
Thr Thr Cys Ile Gly Thr Trp Leu Ile Cys Lys Val Val Gly Ala Ile
         105                 110                 115 gct ccc aag aat cgg tcg ctg gcc tcg acg gtc gcg ttc ctc ttc aac     439
Ala Pro Lys Asn Arg Ser Leu Ala Ser Thr Val Ala Phe Leu Phe Asn
     120                 125                 130 ttt gga tat ctg ctc acg tcc tac aag tac gcg gcc acg gag gat tac     487
Phe Gly Tyr Leu Leu Thr Ser Tyr Lys Tyr Ala Ala Thr Glu Asp Tyr
 135                 140                 145                 150
```

-continued

| | |
|---|---|
| gac atc tgc tac acg atg cag caa tgt gtc cag tgt ctt cgc atg atc<br>Asp Ile Cys Tyr Thr Met Gln Gln Cys Val Gln Cys Leu Arg Met Ile<br>155 160 165 | 535 |
| gga tat ggt atg gac ttt atg gac gga cag ccc aaa ccc gca agc aag<br>Gly Tyr Gly Met Asp Phe Met Asp Gly Gln Pro Lys Pro Ala Ser Lys<br>170 175 180 | 583 |
| aaa cat ctg gcc gct gcc gcg agt gcc gag act ttg gcc aca ttg gtc<br>Lys His Leu Ala Ala Ala Ala Ser Ala Glu Thr Leu Ala Thr Leu Val<br>185 190 195 | 631 |
| gag gag gtc aag gcc aac ccc aac aag gcc gat cag ggc atc gac cac<br>Glu Glu Val Lys Ala Asn Pro Asn Lys Ala Asp Gln Gly Ile Asp His<br>200 205 210 | 679 |
| gtc gtg gtc gct ccc agc ccc gct gcc gtc acc cct gtc agg gaa aag<br>Val Val Val Ala Pro Ser Pro Ala Ala Val Thr Pro Val Arg Glu Lys<br>215 220 225 230 | 727 |
| act cca att tcg ttc gga cgg gac att gct ctc cct cag ttg ccc acg<br>Thr Pro Ile Ser Phe Gly Arg Asp Ile Ala Leu Pro Gln Leu Pro Thr<br>235 240 245 | 775 |
| ttg gcc gag acg atc ggc tat gcc ttc ttc ccg ttc gcg ttc ttg gtc<br>Leu Ala Glu Thr Ile Gly Tyr Ala Phe Phe Pro Phe Ala Phe Leu Val<br>250 255 260 | 823 |
| ggc ccc cag ttt tcg ttc tcg ctc tac aaa aag ttc att tcg atg gag<br>Gly Pro Gln Phe Ser Phe Ser Leu Tyr Lys Lys Phe Ile Ser Met Glu<br>265 270 275 | 871 |
| ctc ttc aat gtg ccg gtg cct gcc tcg gcc gga cgc gat gag gcc aag<br>Leu Phe Asn Val Pro Val Pro Ala Ser Ala Gly Arg Asp Glu Ala Lys<br>280 285 290 | 919 |
| gcc gct gct gct gcg acc gcg aac gga atc ccc cag ggt tct ctg cgc<br>Ala Ala Ala Ala Ala Thr Ala Asn Gly Ile Pro Gln Gly Ser Leu Arg<br>295 300 305 310 | 967 |
| tac gcg ttg cgc tgt ttc tcc ctt ggt gtg ttc tat ctg gga ctg ggt<br>Tyr Ala Leu Arg Cys Phe Ser Leu Gly Val Phe Tyr Leu Gly Leu Gly<br>315 320 325 | 1015 |
| cag gtt ttg gga gga tac ttc ccc acg gcc gca ttg ttg ggt aaa gcc<br>Gln Val Leu Gly Gly Tyr Phe Pro Thr Ala Ala Leu Leu Gly Lys Ala<br>330 335 340 | 1063 |
| ttc ctg gaa cgc tcg tac ctg gag aag gtc ttt atc ttt tgg tgg act<br>Phe Leu Glu Arg Ser Tyr Leu Glu Lys Val Phe Ile Phe Trp Trp Thr<br>345 350 355 | 1111 |
| gga aag act gtc ttg aac aag tac ctt ggc att tgg acc atc gcc gag<br>Gly Lys Thr Val Leu Asn Lys Tyr Leu Gly Ile Trp Thr Ile Ala Glu<br>360 365 370 | 1159 |
| gga ccc tgc gtc ctc tcg ggc atc acc ttc aac ggt tat gac gcc cag<br>Gly Pro Cys Val Leu Ser Gly Ile Thr Phe Asn Gly Tyr Asp Ala Gln<br>375 380 385 390 | 1207 |
| gga cgg ccc gag tgg gac gga ctc cgg aac gtg aac cct ctc aac tat<br>Gly Arg Pro Glu Trp Asp Gly Leu Arg Asn Val Asn Pro Leu Asn Tyr<br>395 400 405 | 1255 |
| gag ttt gcg acg tcc ctg acc cag atc gtg acc tcg ttc aac atg aac<br>Glu Phe Ala Thr Ser Leu Thr Gln Ile Val Thr Ser Phe Asn Met Asn<br>410 415 420 | 1303 |
| aca aac ttc tgg gcc aag ctt tac atc ttc aag cgt ctg cgt ttc ctc<br>Thr Asn Phe Trp Ala Lys Leu Tyr Ile Phe Lys Arg Leu Arg Phe Leu<br>425 430 435 | 1351 |
| ggt aac aag aac ctg tca gcc ctc ggc gtc ttg ctc ttc ttg gcg atc<br>Gly Asn Lys Asn Leu Ser Ala Leu Gly Val Leu Leu Phe Leu Ala Ile<br>440 445 450 | 1399 |
| tgg cac gga acc cat atc ggt tac ttt ttc tgc ttt ggc ctc gag ttc<br>Trp His Gly Thr His Ile Gly Tyr Phe Phe Cys Phe Gly Leu Glu Phe<br>455 460 465 470 | 1447 |

-continued

```
atg gac atg gag acc gag cgt cgg ttg tcg gtt agg ttt ggt cgt ccc      1495
Met Asp Met Glu Thr Glu Arg Arg Leu Ser Val Arg Phe Gly Arg Pro
            475                 480                 485 att aat gcg ttc att gct cgc cag caa ggt gtg agc cat gcg atc ctc      1543
Ile Asn Ala Phe Ile Ala Arg Gln Gln Gly Val Ser His Ala Ile Leu
        490                 495                 500 aag gcc gtt tgg ggt gtc atc acc tgg ctc ttg acg acg agt gcc ctg      1591
Lys Ala Val Trp Gly Val Ile Thr Trp Leu Leu Thr Thr Ser Ala Leu
        505                 510                 515 tac ttt gcg gcc gtg cct ttt gat ctg ttg cag atg gac aag tcg ttg      1639
Tyr Phe Ala Ala Val Pro Phe Asp Leu Leu Gln Met Asp Lys Ser Leu
    520                 525                 530 gcg gcg atc cgg gcg atc aac tac ctc ggc atc tat gtc atg gcg gga      1687
Ala Ala Ile Arg Ala Ile Asn Tyr Leu Gly Ile Tyr Val Met Ala Gly
535                 540                 545                 550 ctt ttg ttc ctg gac att gct ctg tcg gtg gtc atg ccc aag aag cga      1735
Leu Leu Phe Leu Asp Ile Ala Leu Ser Val Val Met Pro Lys Lys Arg
                555                 560                 565 tcc aag tct gtc aag act gag taaaaatgga caaaaaaaag caggttcttt         1786
Ser Lys Ser Val Lys Thr Glu
            570 taacttagat accaggagaa atgaatgaat gaagatgaac gagaatcaag gagacgaagg    1846 aactagtttc tgaatgagaa actgtgttcg aagataataa aaaaaaaaaa aaaaa         1901

<210> SEQ ID NO 10
<211> LENGTH: 1944
<212> TYPE: DNA
<213> ORGANISM: Mortierella alpina

<400> SEQUENCE: 10
atggaggcac tcttgcacca ggttcatgac acctacctgc ccgcttggtt cggacccaaa      60
cccccggcgg cttttctcga ctatggtctg acccagtccc taagcgaggc ctcgggcatt     120
cccgaaccct cgctgcgtct actcatgacg atcctggcgg gttacccagt ctcgttcatt     180
taccgactca tctttctgaa caagacgtcg agcattgtgg gcgaatcggc acggaacgcg     240
ttcttcttgt ccacgggctt gctcctctct tactacttca actcgtttga tatcatccac     300
cctctgacca cctgtatcgg cacctggctc atctgcaagg tcgtaggtgc gatcgctccc     360
aagaatcggt cgctggcctc gacggtcgcg ttcctcttca actttggata tctgctcacg     420
tcctacaagt acgcggccac ggaggattac gacatctgct acacgatgca gcaatgtgtc     480
cagtgtcttc gcatgatcgg atatggtatg gactttatgg acgacagcc caaacccgca     540 agcaagaaac atctggccgc tgccgcgagt gccgagactt ggccacatt ggtcgaggag     600 gtcaaggcca accccaacaa ggccgatcag ggcatcgacc acgtcgtggt cgctcccagc     660
cccgctgccg tcacccctgt cagggaaaag actccaattt cgttcggacg ggacattgct     720
ctccctcagt tgcccacgtt ggccgagacg atcggctatg ccttcttccc gttcgcgttc     780
ttggtcggcc cccagttttc gttctcgctc tacaaaaagt tcatttcgat ggagctcttc     840
aatgtgccgg tgcctgcctc ggccggacgc gatgaggcca aggccgctgc tgctgcgacc     900
gcgaacggaa tccccagggg ttctctgcgc tacgcgttgc gctgtttctc ccttggtgtg     960
ttctatctgg gactgggtca ggttttggga ggatacttcc ccacggccgc attgttgggt   1020
aaagccttcc tggaacgctc gtacctggag aaggtcttta tcttttgtg gactggaaag     1080 actgtcttga acaaggtaca gaacacaaca caaacagctg tgtgtgcgtg tgtgaaagag    1140
```

```
agagcgagag agagaaaggg tgcatgcagg acgatttcgc cattttttt tcttgcgttt   1200 gttgaattga aagtcagttc ttttgactta ctcatgctct atgcaccgca cgtgcctccc   1260
cactcacctt tgtttttcgc tcttttctta tctggcttgc ataatcattt ctgttagtac   1320
cttggcattt ggaccatcgc cgagggaccc tgcgtcctct cgggcatcac cttcaacggt   1380
tatgacgccc agggacggcc cgagtgggac ggactccgga acgtgaaccc tctcaactat   1440
gagtttgcga cgtccctgac ccagatcgtg acctcgttca acatgaacac aaacttctgg   1500
gccaagcttt acatcttcaa gcgtctgcgt ttcctcggta acaagaacct gtcagccctc   1560
ggcgtcttgc tcttcttggc gatctggcac ggaacccata tcggttactt tttctgcttt   1620
ggcctcgagt tcatggacat ggagaccgag cgtcggttgt cggttaggtt tggtcgtccc   1680
attaatgcgt tcattgctcg ccagcaaggt gtgagccatg cgatcctcaa ggccgtttgg   1740
ggtgtcatca cctggctctt gacgacgagt gccctgtact ttgcggccgt gccttttgat   1800
ctgttgcaga tggacaagtc gttggcggcg atccgggcga tcaactacct cggcatctat   1860
gtcatggcgg acttttgtt cctggacatt gctctgtcgg tggtcatgcc caagaagcga   1920
tccaagtctg tcaagactga gtaa                                            1944
```

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: synthetic
      primer

<400> SEQUENCE: 11
ctgtctcctt cccagaggat cagc                                              24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: synthetic
      primer

<400> SEQUENCE: 12
ataaccaaag cgcaagatcc atgg                                              24

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: synthetic
      primer

<400> SEQUENCE: 13
gttgcccacg ttggccgaga cgatc                                             25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: synthetic
      primer

<400> SEQUENCE: 14
atgggttccg tgccagatcg ccaag                                             25

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: synthetic
      primer

<400> SEQUENCE: 15
gaattcatgc taaactcatt cttcggggac gc                                    32

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: synthetic
      primer

<400> SEQUENCE: 16
ctcgagttac agcgtcttga ttttaactgc agc                                   33

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: synthetic
      primer

<400> SEQUENCE: 17
tctagaatgg cacctcccaa cactattg                                         28

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: synthetic
      primer

<400> SEQUENCE: 18
aagcttttac ttcttgaaaa agaccacgtc                                       30

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: synthetic
      primer

<400> SEQUENCE: 19
tctagaatgg ctgctgctcc cagtgtgag                                        29

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: synthetic
      primer

<400> SEQUENCE: 20
aagcttttac tgtgccttgc ccatcttgg                                        29

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: synthetic
      primer

<400> SEQUENCE: 21
tctagaatgg agtcgattgc gcaattcc                                        28

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: synthetic
      primer

<400> SEQUENCE: 22
gagctcttac tgcaacttcc ttgccttctc                                      30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: synthetic
      primer

<400> SEQUENCE: 23
tctagaatgg gtgcggacac aggaaaaacc                                      30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: synthetic
      primer

<400> SEQUENCE: 24
aagcttttac tcttccttgg gacgaagacc                                      30

<210> SEQ ID NO 25
<211> LENGTH: 1203
<212> TYPE: DNA
<213> ORGANISM: Mortierella alpina

<400> SEQUENCE: 25
atggcacctc ccaacactat tgatgccggt ttgacccagc gccatatcag cacctcggcc    60
gccccaacct ctgccaagcc cgccttcgag cgcaactacc agctccctga gttcaccatc   120
aaggagatcc gtgagtgcat ccctgcacac tgctttgagc gctccggtct ccgtggtctt   180
tgccacgttg ctattgatct gacctgggcc tcgctcttgt cctggctgc gacccagatc    240 gacaagttcg agaaccctt gatccgctac ttggcctggc tgcgtattg atcatgcag     300 ggtattgttt gcaccggtat ctgggtattg gcacacgaat gtggtcatca gtccttctcg   360
acctccaaga cccttaacaa cactgtcggc tggatcttgc actcgatgct cttggtccct   420
taccactcct ggagaatctc gcactcgaag caccacaagg ccactggcca catgaccaag   480
gaccaggtct tgttcccaa gacccgctct caggttggct tgccccccaa ggagaatgtt   540
gcagttgccg ttcaggagga ggatatgtcc gtgcacctgg atgaggaggc ccccattgtg   600

```
actttgttct ggatggtgat tcagttcctg ttcggatggc ctgcgtacct tattatgaac    660
gcctctggtc aagactatgg ccgctggacc tcgcacttcc acacctactc tcctatcttt    720
gagccccgca acttttcga cattatcatt tcggatctcg gtgtgttggc tgctcttggt    780
accttgatct acgcctccat gcagctctcg ctcttgaccg tgaccaagta ctacattgtc    840
ccctacttgt ttgtcaactt ctggttggtc ctgatcacct tcttgcagca caccgaccct    900
aagctgcccc attaccgtga gggtgcctgg aacttccagc gtggagccct ctgcaccgtt    960
gaccgctcgt tcggcaagtt cttggaccat atgttccacg gcattgtcca tacccatgta   1020
gcccatcact tgttctcgca gatgccgttc taccatgctg aggaagccac ccatcatctc   1080
aagaaactgc tgggagagta ctacgtctat gacccatcgc cgattgttgt tgcggtctgg   1140
aggtcgttcc gtgaatgccg attcgtggaa gaccatggag acgtggtctt tttcaagaag   1200
taa                                                                 1203

<210> SEQ ID NO 26
<211> LENGTH: 1374
<212> TYPE: DNA
<213> ORGANISM: Mortierella alpina

<400> SEQUENCE: 26
atggctgctg ctcccagtgt gaggacgttt actcgggccg agattttgaa tgccgaggcc     60
ctgaatgagg gcaagaagga tgccgaggca ccctttctga tgatcattga caacaaggtg    120
tacgatgtcc gcgagtttgt ccctgatcat cccggtggaa gtgtgattct cacgcacgtt    180
ggcaaggacg gcactgacgt ctttgacact ttccacccccg aggctgcttg ggagactctt    240 gccaacttt acgttggtga tattgatgag agcgatcgtg ccatcaagaa tgatgacttt    300
gcggccgagg ttcgcaagct gcgcaccttg ttccagtccc ttggctacta cgactcgtcc    360
aaggcatact atgccttcaa ggtctcgttc aacctctgca tctggggctt gtcgactttc    420
attgttgcca gtggggcca gacctcgacc ctcgccaacg tgctctcggc tgcgctcttg    480
ggtctcttct ggcagcagtg cggatggttg gcgcacgact ttttgcacca ccaggtcttc    540
caggaccgtt tctgggtga tctttttcggc gccttcttgg gaggtgtctg ccagggtttc    600
tcgtcctcct ggtggaagga caagcacaac actcaccacg ctgctcccaa cgtccacggc    660
gaggatcccg acattgacac tcaccctctg ttgacctgga gtgagcatgc tctggagatg    720
ttctcggatg ttcctgacga ggagctgacc cgtatgtggt cgcgcttcat ggtcctcaac    780 cagaccggt tctacttccc cattctctcg tttgcccgtc tgtcctggtg cctccagtcc    840
attatgcttg ttctgcccaa cggtcaggcc cacaagccct ctggagcgcg tgtgcccatt    900
tcgttggtcg agcagctgtc tctggctatg cactggacct ggtacctcgc caccatgttc    960
ctgttcatta aggatcccgt caacatgatt gtgtacttt tggtgtcgca ggctgtttgc   1020
ggcaacttgt tggcgattgt gttctcgctc aaccacaacg gcatgcctgt gatctccaag   1080
gaggaagcgg tcgatatgga cttcttcacc aagcagatca tcacgggtcg tgatgttcac   1140
cctggtctgt ttgccaactg gttcacgggg ggattgaact accagattga gcaccacttg   1200
ttcccttcga tgccccgcca caacttttca agatccagc ctgctgtcga cttttgtgc   1260 aaaaagtacg gtgtccgata ccataccact ggtatgatcg agggaactgc agaggtcttt   1320
agccgtttga cgaggtctc caaggcggcc tccaagatgg gcaaggcaca gtaa          1374

<210> SEQ ID NO 27
```

<211> LENGTH: 957
<212> TYPE: DNA
<213> ORGANISM: Mortierella alpina

<400> SEQUENCE: 27

```
atggagtcga ttgcgcaatt cctcccctca aagatgccgc aagatctgtt tattgacctt    60
gcaagggcca tcggtgtcca ggccgcaccc tatgtcgacc ctctcgaggc agcgcttgtg   120
gcccaggccg agaagttctt ccccacggtc gttcatcaca cgcgcggctt tttggtcgcg   180
gtcgagtcac ccttggcccg tgagctgccc ttgatgaacc ccttccacgt gctgttgatc   240
gcgctcgctt acttggtcac ggtctttgtg gcatgcaga tcatgaagaa ctttgaacgg   300
ttcgaggtca agacgttctc gctcttccac aacttttgtc tggtctcgat cagtgcctac   360
atgtgcggcg ggatcttgta cgaggcttac caggccaact atggactgtt tgagaacgcg   420
gccgatcata ccgtccaggg tcttcctatg ccaagatga tctggctctt ctacttctcc   480
aagatcatgg agtttgtcga caccatgatc atggtcctta agaagaacaa ccgccagatc   540
tcgttcttgc acgtctacca ccacagctcc atcttcacca tctggtggtt ggtcaccttt   600
gttgcaccca atggtgaagc ctacttctcg gctgcgttga actcgttcat ccacgtgatc   660
atgtacggct actacttcct gtccgccttg ggcttcaagc aggtgtcgtt catcaagttc   720
tacatcacgc gttcgcagat gacgcagttc tgcatgatgt cgatccagtc ctcctgggac   780
atgtatgcca tgaaggtgct tggccgcccc ggataccct tcttcatcac cgccctgctt   840
tggttctaca tgtggaccat gctcggactc ttctacaact tctacagaaa gaacgccaag   900
ttggccaagc aggccaagat cgatgctgcc aaggagaagg caaggaagtt gcagtaa     957
```

<210> SEQ ID NO 28
<211> LENGTH: 1341
<212> TYPE: DNA
<213> ORGANISM: Mortierella alpina

<400> SEQUENCE: 28

```
atgggtgcgg acacaggaaa aaccttcacc tggcaagaac tcgcggcgca taacaccgag    60
gacagcctcc ttttggctat ccgtggcaat gtatacgatg tcacaaagtt cttgagccgt   120
catcctggtg aacggatac tctcttgctc ggagctggcc gagatgtcac tccggttttt   180
gagatgtacc acgagtttgg agctgcagag gctatcatga agaagtacta tgttggcaca   240
ctggtctcaa atgagttgcc catcttccca gagccaacgg tgttccataa gaccatcaag   300
ggcagagttg aggcatactt taaggaccgg aacatggatt ccaagaacag accagagatc   360
tggggacgat atgctctcat cttggatcc ttgatcgcct cttactacgc gcagctcttt   420
gtaccgttcg tggtcgaacg tacatggctc caggtggtgt ttgctatcat catgggatt   480
gcgtgcgcgc aagtcggatt gaaccctctt cacgatgcct cccactttc agtgacccac   540
aaccccaccg tttggaagat tctcggagcc acgcacgact ttttcaacgg agcatcgtat   600
ctcgtgtgga tgtaccaaca tatgctcggc catcatccct ataccaacat gctggagct   660
gatcccgatg tgtcgaccct tgagcccgat gttcgtcgta tcaagcccaa ccaaaagtgg   720
ttcgtcaacc acatcaacca gcacatgttt gttccttcc tgtacggact gctggcgttc   780
aaggtgcgca tccaggacat caacatcttg tactttgtca agaccaatga cgccattcgt   840
gtcaacccca tctcgacttg gcacaccgtc atgttctggg cggaaaggc cttctttgtc   900
tggtaccgct tgatcgttcc tatgcagtat ctgcccctga gcaaggtgtt gctcttgttc   960
accgtcgcag acatggtctc ttcttactgg ctggcgctga ccttccaggc gaaccacgtt  1020
```

```
gttgaggagg ttcagtggcc attgcctgat gagaatggaa tcatccaaaa ggattgggca      1080
gccatgcagg tcgagactac tcaggattac gcccacgatt cgcacctctg gaccagcatc      1140
acgggcagct tgaactacca agccgttcat catctgttcc cgaacgtttc ccagcatcac      1200
taccctgata tcctggctat catcaaggac acctgcagcg agtacaaggt gccatacctc      1260
gtcaaggata ccttttggca agcgtttgct tcacatttgg agcacttgcg tgtgcttggt      1320
cttcgtccca aggaagagta a                                                1341

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: synthetic
      adoptor A-1

<400> SEQUENCE: 29
gatccggcgc gccgcggccg ctctagagtc gacggcgcgc ca                         42

<210> SEQ ID NO 30
<211> LENGTH: 42
<212> TYPE: DNA
<213> ORGANISM: Artificial Sequence
<220> FEATURE:
<223> OTHER INFORMATION: Description of Artificial Sequence: synthetic
      adoptor A-2

<400> SEQUENCE: 30
agcttggcgc gccgtcgact ctagagcggc cgcggcgcgc cg                         42

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: synthetic
      primer URA5g-F1

<400> SEQUENCE: 31
gtcgaccatg acaagtttgc                                                  20

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: synthetic
      primer URA5g-R1

<400> SEQUENCE: 32
gtcgactgga agacgagcac g                                                21

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: synthetic
      primer GAPDHp-F1

<400> SEQUENCE: 33
gtcgacgatc acgtcgggtg atgagttg                                         28
```

```
<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: synthetic
      primer GAPDHp-R1

<400> SEQUENCE: 34
tctagagatg ttgaatgtgt ggtgtgtg                                       28

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: synthetic
      primer GAPDHt-F1

<400> SEQUENCE: 35
gcggccgcta agaaaaggga gtgaatcgc                                      29

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: synthetic
      primer GAPDHt-R1

<400> SEQUENCE: 36
ggatccggcg cgccgatcca tgcacgggtc cttctc                              36

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: synthetic
      primer XbaI-LPLAT6-F1

<400> SEQUENCE: 37
tctagaatgg aggcactctt gcaccagg                                       28

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: synthetic
      primer NotI-LPLAT6-R1

<400> SEQUENCE: 38
gcggccgctt actcagtctt gacagacttg                                     30

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: synthetic
      primer EcoRV-LPLAT6-F2

<400> SEQUENCE: 39
gatatcgggt aaagccttcc tggaacg                                        27

<210> SEQ ID NO 40
```

```
<211> LENGTH: 33
<212> TYPE: DNA
<213> ORGANISM: Artificial Sequence
<220> FEATURE:
<223> OTHER INFORMATION: Description of Artificial Sequence: synthetic
      primer XbaI-LALAT6-R2

<400> SEQUENCE: 40
tctagattac tcagtcttga cagacttgga tcg                              33

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence: synthetic
      primer XbaI-delta5DS-F1

<400> SEQUENCE: 41
tctagaatgg gtgcggacac aggaaaaac                                   29

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence: synthetic
      primer NotI-delta5DS-R1

<400> SEQUENCE: 42
gcggccgctt actcttcctt gggacgaag                                   29

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: synthetic
      primer NdeI-delta5DS-R2

<400> SEQUENCE: 43
tctagattac tcttccttgg gacgaag                                     27

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: synthetic
      primer XbaI-delta5DS-F2

<400> SEQUENCE: 44
catatgcatc caggacatca acatcttg                                    28

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tttttttttt tttttttttt tttttttttt                                  30
```